US012644107B2

(12) United States Patent
Kim et al.

(10) Patent No.: US 12,644,107 B2
(45) Date of Patent: *Jun. 2, 2026

(54) TARGET-SPECIFIC CRISPR MUTANT

(71) Applicant: TOOLGEN INCORPORATED, Seoul (KR)

(72) Inventors: Young-Hoon Kim, Seoul (KR); Min Hee Jung, Seoul (KR); Joonsun Lee, Gangwon-Do (KR); Eunji Shin, Gyeonggi-do (KR); Kang In Lee, Seoul (KR); Seokjoong Kim, Seoul (KR); Jeongjoon Lee, Gyeonggi-do (KR)

(73) Assignee: TOOLGEN INCORPORATED, Seoul (KR)

( * ) Notice: Subject to any disclaimer, the term of this patent is extended or adjusted under 35 U.S.C. 154(b) by 422 days.

This patent is subject to a terminal disclaimer.

(21) Appl. No.: 17/880,160

(22) Filed: Aug. 3, 2022

(65) Prior Publication Data

US 2023/0130858 A1 Apr. 27, 2023

Related U.S. Application Data

(63) Continuation of application No. 16/628,199, filed as application No. PCT/KR2018/007731 on Jul. 6, 2018, now Pat. No. 11,441,135.

(60) Provisional application No. 62/608,722, filed on Dec. 21, 2017, provisional application No. 62/529,601, filed on Jul. 7, 2017.

(51) Int. Cl.
| | |
|---|---|
| *C12N 9/22* | (2006.01) |
| *C12N 9/78* | (2006.01) |
| *C12N 15/86* | (2006.01) |

(52) U.S. Cl.
CPC ................. *C12N 9/22* (2013.01); *C12N 9/78* (2013.01); *C12N 15/86* (2013.01)

(58) Field of Classification Search
CPC . C12N 9/22; C12N 9/78; C12N 15/86; C12N 15/102; C12N 2310/20; C07K 2319/00; C07K 2319/01; C07K 2319/09
See application file for complete search history.

(56) References Cited

U.S. PATENT DOCUMENTS

| | | | |
|---|---|---|---|
| 10,494,620 | B2 | 12/2019 | Doudna et al. |
| 11,008,555 | B2 | 5/2021 | Oakes et al. |
| 2016/0312280 | A1 * | 10/2016 | May ..................... C12Q 1/6818 |
| 2016/0319260 | A1 | 11/2016 | Joung et al. |
| 2018/0080051 | A1 | 3/2018 | Sheikh et al. |
| 2018/0237771 | A1 | 8/2018 | Kim et al. |
| 2018/0296603 | A1 | 10/2018 | Gori et al. |
| 2019/0185860 | A1 | 6/2019 | Kim et al. |

FOREIGN PATENT DOCUMENTS

| | | |
|---|---|---|
| CN | 105899657 A | 8/2016 |
| EP | 3 498 846 A1 | 6/2019 |
| JP | 2020-530279 A | 10/2020 |
| KR | 10-2018-0031671 A | 3/2018 |
| WO | WO-2015-052231 A2 | 4/2015 |
| WO | WO-2015/089277 A1 | 6/2015 |
| WO | WO-2016-115355 A1 | 7/2016 |
| WO | WO-2016/161207 A1 | 10/2016 |
| WO | WO 2016/196655 * | 12/2016 |
| WO | WO-2016-205613 A1 | 12/2016 |
| WO | WO-2017-040348 A1 | 3/2017 |
| WO | WO-2017/048969 A1 | 3/2017 |
| WO | WO 2017/070633 * | 4/2017 |
| WO | WO-2018-034554 A1 | 2/2018 |
| WO | WO-2019/092042 A1 | 5/2019 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Goeker, M., GenBank accession No. PXW91788, Jun. 7, 2018.*
Sabharwal et al., GenBank accession No. KJQ69483, Mar. 23, 2015.*
Nishiki et al., GenBank accession No. BBE40087, Jul. 7, 2018.*
Dridi, B., GenBank accession No. SLM84820, Apr. 28, 2017.*
Office Action from corresponding European Patent Applcation No. 18829020.9, dated Apr. 13, 2023.
NCBI, NCBI Reference Sequence: WP_010922251.1, Oct. 7, 2015.
International Search Report from corresponding PCT Application No. PCT/KR2018/007731, dated Feb. 8, 2019.
Kim, D. et al. Nat Methods 12, 237-243, 231 p following 243 (2015).
Tsai, S.Q. et al. Nat Biotechnol 33, 187-197 (2015).
Kim, S., Kim, D., Cho, S.W., Kim, J. & Kim, U.S. Genome Res 24, 1012-1019 (2014).
Cho, S.W. et al. Genome Res 24, 132-141 (2014).
Mali, P. et al. Nat Biotechnol 31, 833-838 (2013).
Ran, F.A. et al. Cell 154, 1380-1389 (2013).
Fu, Y., Sander, J.D., Reyon, D., Cascio, V.M. & Joung, J.K. Nat Biotechnol 32, 279-284 (2014).
Nishimasu, H. et al. Cell 156, 935-949 (2014).
Kleinstiver, B.P. et al. Nature 529, 490-495 (2016).
Slaymaker, I.M. et al. Science 351, 84-88 (2016).
Chen, J.S. et al. Nature (2017).

(Continued)

*Primary Examiner* — Delia M Ramirez
(74) *Attorney, Agent, or Firm* — Harness, Dickey & Pierce, P.L.C.

(57) ABSTRACT

The present invention relates to an artificially engineered CRISPR/Cas9 system. More particularly, the present invention relates to an artificially engineered CRISPR enzyme having enhanced target specificity and a use of an artificially engineered CRISPR/Cas9 system including the same enzyme in genome and/or epigenome manipulation or modification, genome targeting, genome editing, and in vitro diagnosis, etc.

8 Claims, 23 Drawing Sheets
Specification includes a Sequence Listing.

(56)                  References Cited

OTHER PUBLICATIONS

Kleinstiver, B.P. et al. Nat Biotechnol 33, 1293-1298 (2015).
Kleinstiver, B.P. et al. Nature 523, 481-485 (2015).
Chen, Z. & Zhao, H. Nucleic Acids Res 33, e154 (2005).
Hsu, P.D. et al. Nat Biotechnol 31, 827-832 (2013).
McKenzie, G.J. & Craig, N.L. BMC Microbiol 6, 39 (2006).
Kulcsar, P.I. et al. Genome Biol 18, 190 (2017).
Zhang, D. et al. Genome Biol 18, 191 (2017).
Komor, A.C., Kim, Y.B., Packer, M.S., Zuris, J.A. & Liu, D.R. Nature 533, 420-424 (2016).
Kim, D., Kim, S., Park, J. & Kim, U.S. Genome Res 26, 406-415 (2016).
Geissmann, Q. PLoS One 8, e54072.
International Search Report from corresponding PCT Application No. PCT/KR2018/005110, dated Jan. 23, 2020.
Tycko, J., et al.; "Methods for Optimizing CRISPR-Cas9 Genome Editing Specificity", Mol Cell. Aug. 4, 2016; 63(3): 355-370.
Vakulskas, C. A., et al.; "A high-fidelity Cas9 mutant delivered as a ribonucleoprotein complex enables efficient gene editing in human haematopoietic stem and progenitor cells", Nat Med. Aug. 2018 ; 24(8): 1216-1224.
Written Opinion of the International Searching Authority from corresponding PCT Application No. PCT/KR2019/005110, dated Jan. 23, 2020.
Lee, J. K., et al.; "Directed evolution of CRISPR-Cas9 to increase its specificity", Nature Communications (2018) 9:3048, p. 1-11.
EESR from corresponding European Patent Application No. 18829020.9, dated Feb. 26, 2021.
Office Action from corresponding Australian Patent Application No. 2018295992, dated Apr. 7, 2021.
Office Action from corresponding Japanese Patent Application No. 2020-500033, dated May 11, 2021.

Written Opinion of the International Searching Authority from corresponding PCT Application No. PCT/KR2018/007731, dated Feb. 8, 2019.
Office Action from corresponding Australian Patent Application No. 2018295992, issued Apr. 7, 2021.
Notice of Allowance from corresponding Australian Patent Application No. 2018295992, issued Oct. 9, 2021.
Office Action from corresponding Japanese Patent Application No. 2020-500033, dated Jan. 26, 2022.
Lee, J. K., et al.; "Directed evolution of CRISPR-Cas9 to increase its specificity", Nat. Commun., 2018, vol. 9, No. 3048, pp. 1-10.
Liu, H.., et al.; "Blossom of CRISPR technologies and applications in disease treatment", Synth. Syst. Biotechnol., 2018, vol. 3, pp. 217-228.
Office Action from corresponding Japanese Patent Application No. 2020-500033, dated Apr. 26, 2021.
Extended European Search Report from corresponding European Patent Application No. 18829020.9, issued Feb. 26, 2021.
Office Action (Non-Final) from corresponding U.S. Appl. No. 16/628,199, dated Jun. 24, 2021.
Office Action (Final) from corresponding U.S. Appl. No. 16/628,199, dated Dec. 17, 2021.
Notice of Reasons for Refusal from corresponding Japanese Patent Application No. 2022-181946, dated Dec. 4, 2023.
Office Action from corresponding Chinese Patent Application No. 201880058272.3 dated Feb. 3, 2023.
Cho, S. W., et al.; "Targeted genome engineering in human cells with the Cas9 RNA-guided endonuclease", Nature Biotechnology, p. 1-3, dated Jan. 29, 2016.
Zhang, X., et al.; "Off-target Effects in CRISPR/Cas9-mediated Genome Engineering", Molecular Therapy-Nucleic Acids, p. 1-8, dated Dec. 14, 2016.
Li Shiyu, Research on CRISPRCas9 Technology in Pichia Pastoris and Bacillus Subtilis dated Jun. 15, 2017.

* cited by examiner

TARGET-SPECIFIC CRISPR MUTANT

CROSS REFERENCE TO RELATED APPLICATIONS

This application is a continuation of U.S. patent application Ser. No. 16/628,199, now U.S. Pat. No. 11,441,135, filed on Jan. 2, 2020, which is a national phase application of PCT Application No. PCT/KR2018/007731, filed on Jul. 6, 2018, which claims priority to U.S. Patent Application Nos. 62/529,601, filed on Jul. 7, 2017 and 62/608,722, filed on Dec. 21, 2017. The entire disclosures of the applications identified in this paragraph are incorporated herein by references.

FIELD

The present invention relates to an artificially engineered CRISPR/Cas9 system. More particularly, the present invention relates to an artificially engineered CRISPR enzyme having improved target specificity, and a use for genome and/or epigenome manipulation or modification, genome targeting, genome editing and in vitro diagnostics, etc. using an artificially engineered CRISPR/Cas9 system including the CRISPR enzyme.

BACKGROUND

The CRISPR-Cas system consists of a guide RNA (gRNA) having a complementary sequence to a target gene or nucleic acid and a CRISPR enzyme which is a nuclease that can cleave a target gene or nucleic acid, wherein the gRNA and the CRISPR enzyme form a CRISPR complex, and the target gene or nucleic acid is cleaved or modified by the formed CRISPR complex.

However, as well as the effect of modifying a target gene or nucleic acid, the modification of an undesired non-target gene or nucleic acid has not been solved yet. The non-target gene or nucleic acid is a gene site having a partially complementary sequence with gRNA and can form partially complementary bonds with the gRNA, wherein due to the partial complementary binding, the CRISPR complex can cleave or modify a corresponding gene site, which is a non-target gene or nucleic acid which is not subjected to modification.

Therefore, to increase efficiency of specifically modifying a target gene or nucleic acid using the CRISPR-Cas system, or to solve a problem such as genetic binding which can cause the modification of a non-target gene or nucleic acid, it is important to increase the target specificity of the CRISPR-Cas system. To increase the target specificity of the CRISPR-Cas system, a variety of research on selection of gRNA with a low amount of non-target gene candidates and adjustment of activity and/or specificity of the CRISPR enzyme has been tried.

PRIOR ART DOCUMENT

Non-Patent Document (Non-patent document 0001) Kim, D. et al. Nat Methods 12, 237-243, 231 p following 243 (2015)

(Non-patent document 0002) Tsai, S. Q. et al. Nat Biotechnol 33, 187-197 (2015)

(Non-patent document 0003) Kim, S., Kim, D., Cho, S. W., Kim, J. & Kim, J. S. Genome Res 24, 1012-1019 (2014)

(Non-patent document 0004) Cho, S. W. et al. Genome Res 24, 132-141 (2014)

(Non-patent document 0005) Mali, P. et al. Nat Biotechnol 31, 833-838 (2013)

(Non-patent document 0006) Ran, F. A. et al. Cell 154, 1380-1389 (2013)

(Non-patent document 0007) Fu, Y., Sander, J. D., Reyon, D., Cascio, V. M. & Joung, J. K. Nat Biotechnol 32, 279-284 (2014)

(Non-patent document 0008) Nishimasu, H. et al. Cell 156, 935-949 (2014)

(Non-patent document 0009) Kleinstiver, B. P. et al. Nature 529, 490-495 (2016)

(Non-patent document 0010) Slaymaker, I. M. et al. Science 351, 84-88 (2016)

(Non-patent document 0011) Chen, J. S. et al. Nature (2017)

(Non-patent document 0012) Kleinstiver, B. P. et al. Nat Biotechnol 33, 1293-1298 (2015)

(Non-patent document 0013) Kleinstiver, B. P. et al. Nature 523, 481-485 (2015)

(Non-patent document 0014) Chen, Z. & Zhao, H. Nucleic Acids Res 33, e154 (2005)

(Non-patent document 0015) Hsu, P. D. et al. Nat Biotechnol 31, 827-832 (2013)

(Non-patent document 0016) McKenzie, G. J. & Craig, N. L. BMC Microbiol 6, 39 (2006)

(Non-patent document 0017) Kulcsar, P. I. et al. Genome Biol 18, 190 (2017)

(Non-patent document 0018) Zhang, D. et al. Genome Biol 18, 191 (2017)

(Non-patent document 0019) Komor, A. C., Kim, Y. B., Packer, M. S., Zuris, J. A. & Liu, D. R. Nature 533, 420-424 (2016)

(Non-patent document 0020) Kim, D., Kim, S., Park, J. & Kim, J. S. Genome Res 26, 406-415 (2016)

(Non-patent document 0021) Geissmann, Q. PLoS One 8, e54072

SUMMARY

Technical Problem

In one aspect, the present invention is directed to providing an artificially engineered CRISPR enzyme having improved target specificity.

Technical Solution

To solve the problem, the present invention relates to an artificially engineered CRISPR enzyme. More particularly, the present invention relates to a Cas9 having improved target specificity for a target gene or nucleic acid and a CRISPR/Cas9 system using the same.

The present invention provides an artificially engineered CRISPR enzyme for a specific purpose.

In one aspect, the artificially engineered CRISPR enzyme may be a SpCas9 variant (mutant) with improved target specificity comprising an artificial manipulation, wherein the artificial manipulation may comprise an artificial manipulation (modification) of one or more amino acids present in one or more regions selected from a first region, a second region, a third region and a fourth region of a wild-type *Streptococcus pyogenes* Cas9 (SpCas9).

The first region of the wild-type SpCas9 may be one or more parts selected from the group consisting of a part of the wild-type SpCas9 interacting with a gRNA, a part of the wild-type SpCas9 interacting with a target sequence, a part of the wild-type SpCas9 interacting with a gRNA-target sequence heteroduplex, and a part of the wild-type SpCas9 interacting with PAM (Protospacer adjacent motif) distal end of the gRNA-target sequence heteroduplex.

Here, the PAM distal end of the gRNA-target sequence heteroduplex may be 6 to 10 base pairs at the end of the gRNA-target sequence heteroduplex far from the PAM location.

Here, the PAM may be 5'-NGG-3'.

The second region of the wild-type SpCas9 may be a part of the wild-type SpCas9 performing a function of cleaving a nucleic acid.

The third region of the wild-type SpCas9 may be a part of the wild-type SpCas9 performing a function of cleaving a nucleic acid.

The fourth region of the wild-type SpCas9 may be one or more parts selected from the group consisting of a part of the wild-type SpCas9 recognizing or interacting with a PAM sequence in a target gene or nucleic acid, and a part of the wild-type SpCas9 interacting with a part of a nucleotide sequence of a gRNA.

The first region of the wild-type SpCas9 may be one or more regions selected from the group consisting of a region located in a REC lobe of the wild-type SpCas9, a whole REC domain of the wild-type SpCas9, and a part of a REC domain of the wild-type SpCas9.

The second region of the wild-type SpCas9 may be one or more regions selected from the group consisting of a region located in a NUC lobe of the wild-type SpCas9, a whole RuvC domain of the wild-type SpCas9, a part of a RuvC domain of the wild-type SpCas9, and a part including a metal dependent nucleic acid cleaving region of a RuvC domain of the wild-type SpCas9.

Here, the metal dependent nucleic acid cleaving region of the RuvC domain may be a region capable of cleaving a binding between nucleic acids at target location by interacting with a metal in the RuvC domain.

The third region of the wild-type SpCas9 may be one or more regions selected from the group consisting of a region located in a NUC lobe of the wild-type SpCas9, a whole HNH domain of the wild-type SpCas9, a part of a HNH domain of the wild-type SpCas9, and a part including a metal dependent nucleic acid cleaving region of a HNH domain of the wild-type SpCas9.

Here, the metal dependent nucleic acid cleaving region of the HNH domain may be a region capable of cleaving a binding between nucleic acids at target location by interacting with a metal in the HNH domain.

The fourth region of the wild-type SpCas9 may be one or more regions selected from the group consisting of a region located in a NUC lobe of the wild-type SpCas9, a whole PI domain of the wild-type SpCas9, and a part of a PI domain of the wild-type SpCas9.

The first region may comprise one or more regions selected from the group consisting of a region 1-1 composed of an amino acid sequence from phenylalanine at $196^{th}$ position (F196) to isoleucine at $282^{th}$ position (I282) of the wild-type SpCas9, a region 1-2 composed of an amino acid sequence from proline at $316^{th}$ position (P316) to asparagine at $394^{th}$ position (N394) of the wild-type SpCas9, a region 1-3 composed of an amino acid sequence from lysine at $510^{th}$ position (K510) to asparagine at $612^{th}$ position (N612) of the wild-type SpCas9, and a region 1-4 composed of an amino acid sequence from threonine at $678^{th}$ position (T678) to histidine at $698^{th}$ position (H698) of the wild-type SpCas9.

The first region may comprise N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9.

Here, the second region may comprise one or more regions selected from the group consisting of a region 2-1 composed of an amino acid sequence from methionine at $1^{st}$ position (M1) to threonine at $22^{th}$ position (T22) of the wild-type SpCas9, a region 2-2 composed of an amino acid sequence from proline at $731^{th}$ position (P731) to threonine at $770^{th}$ position (T770) of the wild-type SpCas9, and a region 2-3 composed of an amino acid sequence from glutamine at $926^{th}$ position (Q926) to serine at $1040^{th}$ position (S1040) of the wild-type SpCas9.

The second region may comprise I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 of the wild-type SpCas9.

Here, the third region may comprise a region 3-1 composed of an amino acid sequence from lysine at $775^{th}$ position (K775) to leucine at $900^{th}$ position (L900) of the wild-type SpCas9.

The third region may comprise K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 of the wild-type SpCas9.

Here, the fourth region may comprise a region 4-1 composed of an amino acid sequence from glutamic acid at $1099^{th}$ position (E1099) to valine at $1139^{th}$ position (V1139) of the wild-type SpCas9.

The fourth region may comprise T1102, S1106, E1108, S1116, D1117, D1125, D1127, D1135, S1136 and T1138 of the wild-type SpCas9.

In an exemplary embodiment, the one or more amino acids present in one or more regions selected from the first region, the second region, the third region and the fourth region of the wild-type SpCas9 may be one or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9.

In one exemplary embodiment, the one or more amino acids present in one or more regions selected from the first region, the second region, the third region and the fourth region of the wild-type SpCas9 may be one or more amino acids selected from the group consisting of A203, N277, G366, F539, I601, M763, K890, D965, F1038, T1102 and D1127 of the wild-type SpCas9.

The artificial manipulation may be a deletion of the one or more amino acids present in one or more regions selected from the first region, the second region, the third region and the fourth region of the wild-type SpCas9.

The artificial manipulation may be a substitution of the one or more amino acids present in one or more regions selected from the first region, the second region, the third region and the fourth region of the wild-type SpCas9 with a different amino acid.

Here, the different amino acid may be an amino acid having a smaller functional group than the one or more amino acids present in one or more regions selected from the first region, the second region, the third region and the fourth region of the wild-type SpCas9.

Here, the different amino acid may be an amino acid having a larger functional group than the one or more amino acids present in one or more regions selected from the first region, the second region, the third region and the fourth region of the wild-type SpCas9.

Here, the different amino acid may be an amino acid having a higher hydropathy index than the one or more amino acids present in one or more regions selected from the first region, the second region, the third region and the fourth region of the wild-type SpCas9.

Here, the different amino acid may be an amino acid having a lower hydropathy index than the one or more amino acids present in one or more regions selected from the first region, the second region, the third region and the fourth region of the wild-type SpCas9.

In one aspect, the SpCas9 variant may be a target specific SpCas9 (TS-SpCas9) variant comprising an artificial manipulation of one or more amino acids selected from the group consisting of A203, N277, G366, F539, I601, M763, K890, D965, F1038, T1102 and D1127 of the wild-type SpCas9.

The artificial manipulation may be a deletion or a substitution of one or more amino acids selected from the group consisting of A203, N277, G366, F539, I601, M763, K890, D965, F1038, T1102 and D1127 of the wild-type SpCas9 with a different amino acid.

Here, the different amino acid may be an amino acid having a larger or smaller functional group than the one or more amino acids selected from the group consisting of A203, N277, G366, F539, I601, M763, K890, D965, F1038, T1102 and D1127 of the wild-type SpCas9.

Here, the different amino acid may be an amino acid having a higher or lower hydropathy index than the one or more amino acids selected from the group consisting of A203, N277, G366, F539, I601, M763, K890, D965, F1038, T1102 and D1127 of the wild-type SpCas9.

The TS-SpCas9 variant may comprise an artificial manipulation of F539 of the wild-type SpCas9.

The TS-SpCas9 variant may comprise an artificial manipulation of M763 of the wild-type SpCas9.

The TS-SpCas9 variant may comprise an artificial manipulation of K890 of the wild-type SpCas9.

The TS-SpCas9 variant may comprise an artificial manipulation of F539/M763(F539 and M763), F539/K890 or M763/K890 of the wild-type SpCas9.

The TS-SpCas9 variant may comprise an artificial manipulation of F539, M763 and K890 of the wild-type SpCas9.

In one aspect, the artificially engineered CRISPR enzyme may be a fusion protein comprising the TS-SpCas9 variant.

The fusion protein may comprise one or more functional domains.

Here, the functional domain may be one or more domains selected from the group consisting of a domain having methylase activity, demethylase activity, transcription activation activity, transcription repression activity, transcription release factor activity, histone modification activity, RNA cleavage activity or nucleic acid binding activity, a tag for isolation and purification of a protein (including a peptide), a report gene, a NLS (nuclear localization sequence or signal), a NES (nuclear export sequence or signal), and a deaminase.

In one aspect, the artificially engineered CRISPR enzyme may be a form of a nucleic acid encoding the SpCas9 variant, the TS-SpCas9 variant and/or the fusion protein.

In one aspect, the nucleic acid may be included in a vector.

In one aspect, the nucleic acid encoding the SpCas9 variant, the TS-SpCas9 variant and/or the fusion protein; and/or the vector may be introduced in a cell.

In one aspect, a genome of a cell may be artificially manipulated using the SpCas9 variant, the TS-SpCas9 variant, and/or the fusion protein, with a gRNA.

The gRNA may be a nucleic acid comprising a nucleotide sequence complementary binding to a target sequence of a target gene present in the genome of the cell.

Advantageous Effects

According to the present invention, a CRISPR-Cas system having improved target specificity using an artificially manipulated CRISPR enzyme can be used in genome and/or epigenome manipulation or modification, genome targeting, genome editing and in vitro diagnostics.

DETAILED DESCRIPTION

Figure 1:
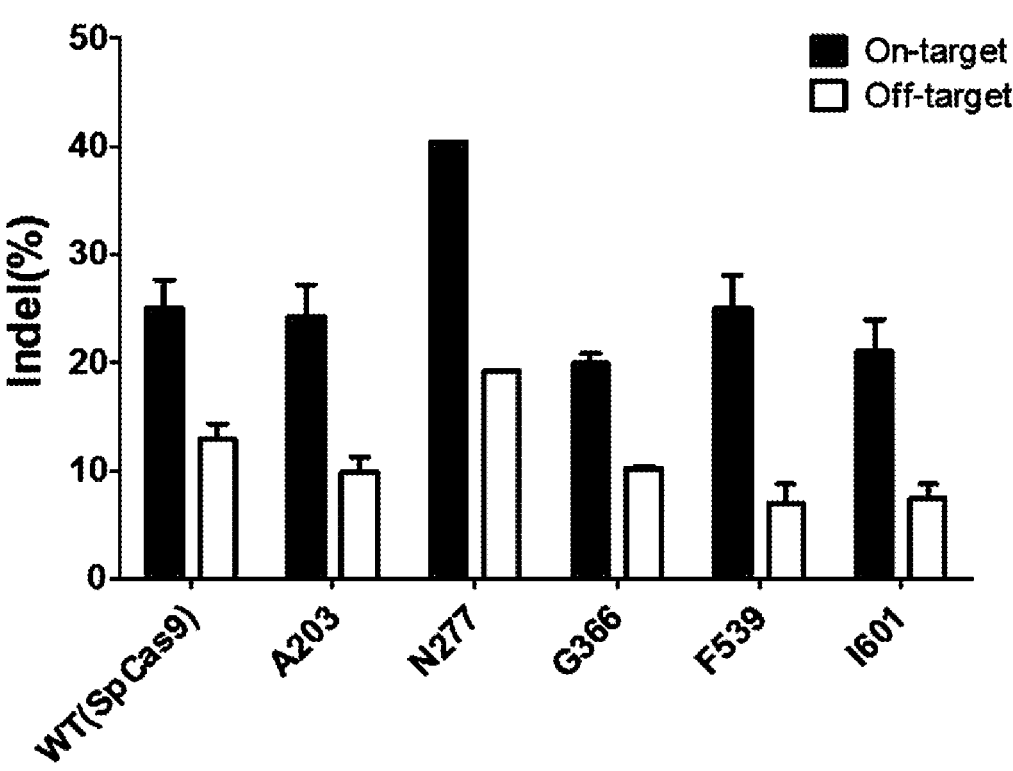
FIG. 1 is a graph showing indel (insertion and deletion) frequencies (%), which represents the manipulation effect of a target gene (DMD gene) by first region variants of SpCas9.

Unless defined otherwise, all technical and scientific terms used in the specification have the same meanings as conventionally understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, the materials, methods and examples are merely illustrative, but are not intended to be limited.

One aspect of the disclosure disclosed herein relates to a CRISPR enzyme.

The "CRISPR enzyme" is a major protein component of a clustered regularly interspaced short palindromic repeats (CRISPR)-CRISPR-associated protein (Cas) system, and forms a complex with a guide RNA (gRNA), thereby forming a CRISPR-Cas system.

The "gRNA" refers to an RNA capable of specifically targeting a CRISPR complex, that is, a gRNA-CRISPR enzyme complex, with respect to a target gene or nucleic acid. The gRNA is specific RNA for a target sequence, which may bind to the CRISPR enzyme, and guide the CRISPR enzyme to the target gene or nucleic acid. Here, the "target sequence" is a nucleotide sequence present in a target gene or nucleic acid, and specifically, a partial nucleotide sequence of a target region in the target gene or nucleic acid. The "target region" used herein is a site that can be modified by a guide nucleic acid-editor protein in the target gene or nucleic acid.

The gRNA may include multiple domains. Due to each domain, interactions may occur in a strand or between strands of a three-dimensional structure or an active form of the gRNA.

The gRNA may be called single-stranded gRNA (single RNA molecule; single gRNA; sgRNA); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or nucleic acid; a first complementary domain; a linker domain; a second complementary domain which has a complementary sequence to the first complementary domain sequence and may form with the first complementary domain sequence; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or nucleic acid, and a first complementary domain; and a second strand which includes a second complementary domain, which has a complementary sequence to the first complementary domain sequence and may form with the first complementary domain sequence, a proximal domain, and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a target gene or nucleic acid; a first complementary domain; and a second complementary domain, which has a complementary sequence to the first complementary domain sequence and may form with the first complementary domain sequence, in the 5' to 3' direction.

The CRISPR enzyme is a nucleic acid or polypeptide (or a protein) having a sequence encoding the CRISPR enzyme, and representatively, a Type II CRISPR enzyme or Type V CRISPR enzyme is widely used.

The CRISPR enzyme may be a Type II CRISPR enzyme.

The Type II CRISPR enzyme may be a Cas9.

Here, the Cas9 may be derived from various microorganisms such as *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus* and *Acaryochloris marina,* etc.

Here, the Cas9 may be isolated from a naturally-occurring microorganism, or produced unnaturally by a recombinant method or synthetic method.

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 domain and REC2 domain play an important role in recognizing a double strand formed in gRNA, for example, single-stranded gRNA, double-stranded gRNA or tracrRNA.

The NUC lobe includes an RuvC domain, an HNH domain and a PAM-interaction (PI) domain. Here, the RuvC domain encompasses RuvC-like domains, and the HNH domain encompasses HNH-like domains.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as an RuvCI domain, RuvCII domain or RuvCIII domain in the art, and generally called an RuvC I, RuvCII or RuvCIII.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II motif and RuvC III motif.

The PI domain recognizes a specific nucleotide sequence in a target gene or nucleic acid, that is, a protospacer adjacent motif (PAM) or interacts with PAM. Here, the PAM may vary according to the origin of the type II CRISPR enzyme. For example, when the CRISPR enzyme is SpCas9, the PAM may be 5'-NGG-3', when the CRISPR enzyme is *Streptococcus thermophilus* Cas9 (StCas9), the PAM may be 5'-NNAGAAW-3' (W=A or T), when the CRISPR enzyme is *Staphylococcus aureus* Cas9 (SaCas9), the PAM may be 5'-NNGRR-3' (R=A or G), when the CRISPR enzyme is *Neisseria meningitides* Cas9 (NmCas9), the PAM may be 5'-NNNNGATT-3', and when the CRISPR enzyme is *Campylobacter jejuni* Cas9 (CjCas9), the PAM may be 5'-NNNVRYAC-3' (V=G, C or A, R=A or G, Y=C or T), where the N may be A, T, G or C; or A, U, G or C. While it is generally understood that PAM is determined according to the origin of the above-described enzyme, according to the progression of research on mutants of the enzyme derived from the above-described origins, the PAM may vary.

The CRISPR enzyme may be a nuclease or restriction enzyme which has a function of cleaving the double strands of a target gene or nucleic acid.

The CRISPR enzyme may be a fully active CRISPR enzyme.

The "fully active" refers to having the same function as the function of a wild-type CRISPR enzyme, and the CRISPR enzyme in such a state is called a fully active CRISPR enzyme. Here, the "function of a wild-type CRISPR enzyme" refers to the state of a wild-type CRISPR enzyme having functions of cleaving the double strands of DNA, that is, a first function of cleaving the first strand of the double strands of DNA and a second function of cleaving the second strand thereof.

The fully active CRISPR enzyme may be a wild-type CRISPR enzyme that cleaves the double strands of DNA.

The fully active CRISPR enzyme may be a CRISPR enzyme variant formed by modifying or manipulating a wild-type CRISPR enzyme that cleaves the double strands of DNA.

The CRISPR enzyme variant may be an enzyme formed by substituting one or more amino acids with different amino acids, or removing one or more amino acids in the amino acid sequence of the wild-type CRISPR enzyme.

The CRISPR enzyme variant may be an enzyme produced by adding one or more amino acids to the amino acid sequence of the wild-type CRISPR enzyme. Here, the added amino acid may be located at the N-terminus or C-terminus of the wild-type enzyme, or in the amino acid sequence thereof.

The CRISPR enzyme variant may be a fully active enzyme having an improved function compared to the wild-type CRISPR enzyme.

For example, a specifically modified or engineered form of the wild-type CRISPR enzyme, that is, a CRISPR enzyme variant may cleave a double-stranded DNA in a state which does not bind to the double-stranded DNA to be cleaved or keep a constant distance thereto. In this case, the modified or engineered form may be a fully active CRISPR enzyme having an improved functional activity, compared to the wild-type CRISPR enzyme.

The CRISPR enzyme variant may be a fully active CRISPR enzyme having a reduced function compared to the wild-type CRISPR enzyme.

For example, a specifically modified or engineered form of the wild-type CRISPR enzyme, that is, a CRISPR enzyme variant may cleave a double-stranded DNA in a state which is closing to a certain distance from or is forming a specific binding to the double-stranded DNA to be cleaved. Here, the specific binding may be, for example, a bond between an amino acid at a specific site of the CRISPR enzyme variant and a DNA nucleotide sequence at a cleavage site. In this case, the modified or engineered form may be a fully active CRISPR enzyme having a reduced functional activity, compared to the wild-type CRISPR enzyme.

The CRISPR enzyme may be an incomplete or partially-active CRISPR enzyme.

The "incomplete or partially active" means a state having one selected from functions of the wild-type CRISPR enzyme, that is, a first function of cleaving the first strand of the double strands of DNA and a second function of cleaving the second strand of the double strands of DNA. The CRISPR enzyme in such a state is referred to as an incomplete or partially-active CRISPR enzyme. In addition, the incomplete or partially-active CRISPR enzyme may be referred to as a nickase.

The term "nickase" refers to a CRISPR enzyme engineered or modified to cleave only one strand of the double strand of the target gene or nucleic acid, and the nickase has nuclease activity of cleaving a single strand, for example, a strand that is non-complementary or complementary to gRNA of the target gene or nucleic acid. Therefore, to cleave the double strand, nuclease activity of the two nickases is needed.

The nickase may have a nuclease activity caused by a RuvC domain of the CRISPR enzyme. That is, the nickase may not include a nuclease activity caused by an HNH domain of the CRISPR enzyme, and to this end, the HNH domain may be manipulated or modified.

In one example, when the CRISPR enzyme is a Type II CRISPR enzyme, the nickase may be a Type II CRISPR enzyme including a modified HNH domain.

For example, when the Type II CRISPR enzyme is wild-type SpCas9, the nickase may be a SpCas9 variant having an inactivated nuclease activity of the HNH domain due to a mutation of histidine to alanine at position 840 in the amino acid sequence of the wild-type SpCas9. Since the nickase produced thereby, that is, the SpCas9 variant has a nuclease activity caused by a RuvC domain, a non-complementary strand of a target gene or nucleic acid, that is, a strand that does not complementarily bind with gRNA may be cleaved.

For another example, when the Type II CRISPR enzyme is wild-type CjCas9, the nickase may be a CjCas9 variant having an inactivated nuclease activity of a HNH domain due to a mutation of histidine to alanine at position 559 in the amino acid sequence of the wild-type CjCas9. Since the nickase produced thereby, that is, the CjCas9 variant has a nuclease activity caused by a RuvC domain, a non-complementary strand of a target gene or nucleic acid, that is, a strand that does not complementarily bind with gRNA may be cleaved.

In addition, the nickase may have a nuclease activity caused by the HNH domain of the CRISPR enzyme. That is, the nickase may not include a nuclease activity caused by the RuvC domain of the CRISPR enzyme, and to this end, the RuvC domain may be manipulated or modified.

In one example, when the CRISPR enzyme is a Type II CRISPR enzyme, the nickase may be a Type II CRISPR enzyme including the modified RuvC domain.

For example, when the Type II CRISPR enzyme is wild-type SpCas9, the nickase may be a SpCas9 variant having an inactivated nuclease activity of the RuvC domain due to a mutation of aspartic acid to alanine at position 10 in the amino acid sequence of the wild-type SpCas9. Since the nickase produced thereby, that is, the SpCas9 variant has a nuclease activity caused by an HNH domain, a complementary strand of a target gene or nucleic acid, that is, a strand complementarily binding to gRNA may be cleaved.

For another example, when the Type II CRISPR enzyme is wild-type CjCas9, the nickase may be a CjCas9 variant having an inactivated nuclease activity of the RuvC domain due to a mutation of aspartic acid to alanine at position 8 in the amino acid sequence of the wild-type CjCas9. Since the nickase produced thereby, that is, the CjCas9 variant has a nuclease activity caused by an HNH domain, a complementary strand of a target gene or nucleic acid, that is, a strand complementarily binding to gRNA may be cleaved.

The CRISPR enzyme may be an inactive CRISPR enzyme.

The "inactive" may mean a state of losing functions of the wild-type CRISPR enzyme, that is, both of a first function of cleaving the first strand of the double-stranded DNA and a second function of cleaving the second strand of the double-stranded DNA. The CRISPR enzyme in such a state is referred to as an inactive CRISPR enzyme.

The inactive CRISPR enzyme may have nuclease inactivity due to a mutation in a domain having a nuclease activity of the wild-type CRISPR enzyme.

The inactive CRISPR enzyme may have nuclease inactivity due to mutations in the RuvC domain and the HNH domain. That is, the inactive CRISPR enzyme may not include a nuclease activity caused by the RuvC domain and the HNH domain of the CRISPR enzyme, and to this end, the RuvC domain and the HNH domain may be manipulated or modified.

In one example, when the CRISPR enzyme is a Type II CRISPR enzyme, the inactive CRISPR enzyme may be a Type II CRISPR enzyme including the modified RuvC domain and the modified HNH domain.

For example, when the Type II CRISPR enzyme is a wild-type SpCas9, the inactive CRISPR enzyme may be a SpCas9 variant having an inactivated nuclease activity of the RuvC domain and the HNH domain by alanine mutations of both of aspartic acid at position 10 and histidine at position 840 in the amino acid sequence of the wild-type SpCas9. Since the inactive CRISPR enzyme produced thereby, that is, the SpCas9 variant has an inactivated nuclease activity of the RuvC domain and the HNH domain, none of the double strands of the target gene or nucleic acid may be cleaved.

For another example, when the Type II CRISPR enzyme is wild-type CjCas9, the inactive CRISPR enzyme may be a CjCas9 variant having an inactivated nuclease activity of the RuvC domain and the HNH domain by alanine mutations of both of aspartic acid at position 8 and histidine at position 559 in the amino acid sequence of the wild-type CjCas9. Since the inactive CRISPR enzyme produced thereby, that is, the CjCas9 variant has an inactivated nuclease activity of the RuvC domain and the HNH domain, none of the double strands of the target gene or nucleic acid may be cleaved.

The CRISPR enzyme may have a helicase activity, that is, a function of unwinding the helical structure of a double-stranded nucleic acid, in addition to the above-described nuclease activity.

In addition, the CRISPR enzyme may be modified to have a fully active, incomplete or partially-active, or inactive helicase activity.

According to an exemplary embodiment of the disclosure of the specification, the CRISPR enzyme may be an artificially engineered CRISPR enzyme.

The term "artificially engineered (artificially modified or manipulated)" means a state formed by artificial modification, not a naturally-occurring state. Here, the artificial modification may occur in a nucleic acid encoding the CRISPR enzyme, and/or protein thereof. In addition, the artificial modification includes all modifications which are possible artificial manipulations occurring in a process of producing a protein from a nucleic acid encoding the CRISPR enzyme, that is, the entire process including transcription, post-transcriptional modification, translation and post-translational modification. Hereinafter, an unnatural, artificially engineered or modified CRISPR enzyme may be used interchangeably with an artificial CRISPR enzyme or CRISPR enzyme variant (CRISPR enzyme mutant).

The artificially engineered CRISPR enzyme may be a CRISPR enzyme variant having modified functions of the wild-type CRISPR enzyme, that is, a first function of cleaving a first strand of the double-stranded DNA and/or a second function of cleaving a second strand of the double-stranded DNA.

For example, the CRISPR enzyme variant may be in a form in which the first function of the functions of the wild-type CRISPR enzyme is lost.

Alternatively, the CRISPR enzyme variant may be in a form in which the first function of the functions of the wild-type CRISPR enzyme is improved.

For example, the CRISPR enzyme variant may be in a form in which the second function of the functions of the wild-type CRISPR enzyme is lost.

Alternatively, the CRISPR enzyme variant may be in a form in which the second function of the functions of the wild-type CRISPR enzyme is improved.

For example, the CRISPR enzyme variant may be in a form in which all of the functions, that is, the first and second functions, of the wild-type CRISPR enzyme are lost.

Alternatively, the CRISPR enzyme variant may be in a form in which all of the functions, that is, the first and second functions, of the wild-type CRISPR enzyme are improved.

Alternatively, the CRISPR enzyme variant may be in a form in which, among the functions of the wild-type CRISPR enzyme, the first function is lost and the second function is improved.

Alternatively, the CRISPR enzyme variant may be in a form in which, among the functions of the wild-type CRISPR enzyme, the first function is improved and the second function is lost.

The artificially engineered CRISPR enzyme may form a gRNA-CRISPR enzyme complex by an interaction with gRNA.

Here, the artificially engineered CRISPR enzyme may be a CRISPR enzyme variant modified a function of interacting with gRNA of the wild-type CRISPR enzyme.

For example, the CRISPR enzyme variant may be in a form with reduced interaction with gRNA, compared to the wild-type CRISPR enzyme.

Alternatively, the CRISPR enzyme variant may be in a form with increased interaction with gRNA, compared to the wild-type CRISPR enzyme.

For example, the CRISPR enzyme variant may be in a form with reduced interaction with gRNA while having a first function of the wild-type CRISPR enzyme.

Alternatively, the CRISPR enzyme variant may be in a form with increased interaction with gRNA while having a first function of the wild-type CRISPR enzyme.

For example, the CRISPR enzyme variant may be in a form with reduced interaction with gRNA while having second function of the wild-type CRISPR enzyme.

Alternatively, the CRISPR enzyme variant may be in a form with increased interaction with gRNA while having second function of the wild-type CRISPR enzyme.

For example, the CRISPR enzyme variant may be in a form with reduced interaction with gRNA while not having a first function and a second function of the wild-type CRISPR enzyme.

Alternatively, the CRISPR enzyme variant may be in a form with increased interaction with gRNA while not having a first function and a second function of the wild-type CRISPR enzyme.

Here, various gRNA-CRISPR enzyme complexes may be formed according to the interaction strength between gRNA and a CRISPR enzyme variant, and have a difference in function of accessing or cleaving a target sequence according to the CRISPR enzyme variant.

For example, only when the gRNA-CRISPR enzyme complex formed by the CRISPR enzyme variant having a reduced interaction with gRNA becomes very close or localized to a target sequence completely complementary binding to gRNA, the double or single strand(s) of the target sequence may be cleaved.

The artificially engineered CRISPR enzyme disclosed herein may be a CRISPR enzyme variant formed by modifying at least one amino acid of the amino acid sequence of the wild-type CRISPR enzyme.

The CRISPR enzyme variant may be in a form in which at least one amino acid is removed from the amino acid sequence of the wild-type CRISPR enzyme.

In one example, the CRISPR enzyme variant may be in a form in which one or more amino acids are removed from positively-charged amino acids of the wild-type CRISPR enzyme.

In another example, the CRISPR enzyme variant may be in a form in which one or more amino acids are removed from negatively-charged amino acids of the wild-type CRISPR enzyme.

In still another example, the CRISPR enzyme variant may be in a form in which one or more amino acids are removed from uncharged amino acids (or non-charged amino acids) of the wild-type CRISPR enzyme.

In yet another example, the CRISPR enzyme variant may be in a form in which one or more amino acids are removed from the positively charged amino acids, the negatively charged amino acids, and non-charged amino acids of the wild-type CRISPR enzyme.

The CRISPR enzyme variant may be in a form in which at least one amino acid selected from the amino acid sequence of the wild-type CRISPR enzyme is substituted with a different amino acid.

Here, the different amino acid, that is, the substituted amino acid may be one amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Here, the alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine may be used as itself or as chemically modified forms thereof including methylation, acetylation, and phosphorylation.

In one example, the CRISPR enzyme variant may be in a form in which one or more amino acid selected from the positively charged amino acids of the wild-type CRISPR enzyme are substituted with a different amino acid. Here, the different amino acid may be one or more amino acids selected from stereoisomers of the selected one or more amino acids, other positively charged amino acids, negatively charged amino acids and non-charged amino acids.

In another example, the CRISPR enzyme variant may be in a form in which one or more amino acids of the negatively charged amino acids of the wild-type CRISPR enzyme are substituted with a different amino acid. Here, the different amino acid may be one or more amino acids selected from stereoisomers of the selected one or more amino acids, positively charged amino acids, other negatively charged amino acids and non-charged amino acids.

In still another example, the CRISPR enzyme variant may be in a form in which one or more amino acids of the non-charged amino acids of the wild-type CRISPR enzyme are substituted with a different amino acid. Here, the different amino acid may be one or more amino acids selected from stereoisomers of the selected one or more amino acids, other non-charged amino acids, positively charged amino acids and negatively charged amino acids.

In yet another example, the CRISPR enzyme variant may be in a form in which one or more amino acids of the positively charged, negatively charged and non-charged amino acids of the wild-type CRISPR enzyme are substituted with a different amino acid. Here, the different amino acid may be one or more amino acids selected from stereoisomers of the selected one or more amino acids, positively charged amino acids, negatively charged amino acids and non-charged amino acids.

The CRISPR enzyme variant may be in a form in which at least one amino acid is substituted or removed from the amino acid sequence of the wild-type CRISPR enzyme.

The artificially engineered CRISPR enzyme disclosed herein may be a CRISPR enzyme variant formed by adding at least one amino acid to the amino acid sequence of the wild-type CRISPR enzyme.

The CRISPR enzyme variant may be in a form in which at least one amino acid is added, compared to the amino acid sequence of the wild-type CRISPR enzyme.

Alternatively, the CRISPR enzyme variant may be in a form in which at least one functional domain is added to the amino acid sequence of the wild-type CRISPR enzyme.

Here, the functional domain may consist of one or more amino acids, and may be a peptide or polypeptide.

Here, the functional domain may be a domain having an additional function, in addition to the original functions of the wild-type CRISPR enzyme, such as the first function of cleaving the first strand of the double-stranded DNA and the second function of cleaving the second strand thereof.

Alternatively, the functional domain may be a domain having a function similar to the original functions of the wild-type CRISPR enzyme, such as the first function of cleaving the first strand of the double-stranded DNA and the second function of cleaving the second strand thereof.

In one example, the functional domain may be a domain having methylase activity, demethylase activity, transcription activation activity, transcription repression activity, transcription release factor activity, histone modification activity, RNA cleavage activity or nucleic acid binding activity.

In another example, the functional domain may be a tag or reporter gene for isolation and purification of a protein (including a peptide). Here, the tag includes a histidine (His) tag, a V5 tag, a FLAG tag, an influenza hemagglutinin (HA) tag, a Myc tag, a VSV-G tag and a thioredoxin (Trx) tag, etc., and the reporter gene includes glutathione-S-transferase (GST), horseradish peroxidase (HRP), chloramphenicol acetyltransferase (CAT), β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In still another example, the functional domain may be a deaminase.

For example, an incomplete or partial CRISPR enzyme may additionally include a cytidine deaminase as a functional domain. Alternatively, an incomplete or partial CRISPR enzyme may additionally include an adenine deaminase as a functional domain.

In yet another example, the functional domain may be a nuclear localization sequence or signal (NLS) or a nuclear export sequence or signal (NES).

For example, the CRISPR enzyme may include one or more NLSs. Here, one or more NLSs may be included at an N-terminus of the CRISPR enzyme or the proximity thereof; a C-terminus of the CRISPR enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 12); NLS from nucleoplasmin (e.g., nucleoplasmin bipartite NLS having the sequence KRPAATKK-AGQAKKKK (SEQ ID NO: 13)); c-myc NLS having the amino acid sequence PAAKRVKLD (SEQ ID NO: 14) or RQRRNELKRSP (SEQ ID NO: 15); hRNPA1 M9 NLS having the sequence NQSSNFGPMKGGNFG-GRSSGPYGGGGQYFAKPRNQGGY (SEQ ID NO: 16); the sequence RMRIZFKNKGKDTAELRRRRVEVS-VELRKAKKDEQILKRRNV (SEQ ID NO: 17) of the IBB domain from importin-α; the sequences VSRKRPRP (SEQ ID NO: 18) and PPKKARED (SEQ ID NO: 19) of a myoma T protein; the sequence PQPKKKPL (SEQ ID NO: 20) of human p53; the sequence SALIKKKKKMAP (SEQ ID NO: 21) of mouse c-abl IV; the sequences DRLRR (SEQ ID NO: 22) and PKQKKRK (SEQ ID NO: 23) of influenza virus NS1; the sequence RKLKKKIKKL (SEQ ID NO: 24) of a hepatitis delta virus antigen; the sequence REKKKFLKRR (SEQ ID NO: 25) of a mouse Mx1 protein; the sequence KRKGDEVDGVDEVAKKKSKK (SEQ ID NO: 26) of a human poly (ADP-ribose) polymerase; or the sequence RKCLQAGMNLEARKTKK (SEQ ID NO: 27) of a steroid hormone receptor (human) glucocorticoid.

The artificially engineered CRISPR enzyme may be a CRISPR enzyme variant formed by modifying at least one amino acid in the amino acid sequence of a specific region of the wild-type CRISPR enzyme.

The artificially engineered CRISPR enzyme may be a CRISPR enzyme variant formed by adding one or more amino acids to a specific region of the wild-type CRISPR enzyme.

Here, the specific region of the wild-type CRISPR enzyme may be one or more regions selected from a first region, a second region, a third region and a fourth region.

The first region may be a part of the wild-type CRISPR enzyme interacting with a gRNA.

The first region may be a part of the wild-type CRISPR enzyme interacting with a target sequence.

The first region may be a part of the wild-type CRISPR enzyme interacting with a gRNA-target sequence heteroduplex.

The first region may be a part of the wild-type CRISPR enzyme interacting with a PAM distal end of the gRNA-target sequence heteroduplex.

Here, the PAM distal end of the gRNA-target sequence heteroduplex may mean 6 to 10 base pairs at the end of the gRNA-target sequence heteroduplex far from the PAM location, which is a sequence of 6 to 10 bases of the gRNA and a 6 to 10 bases sequence of the target sequence complementarily binding thereto.

The first region may be a region located in a REC lobe of the wild-type CRISPR enzyme.

The first region may be all or a part of a REC domain of the wild-type CRISPR enzyme.

The second region may be a part of the wild-type CRISPR enzyme having the first function or the second function of the wild-type CRISPR enzyme.

The second region may be a region located in an NUC lobe of the wild-type CRISPR enzyme.

The second region may be all or a part of a wild-type RuvC domain of the CRISPR enzyme.

The second region may be a part of a RuvC domain including a metal dependent nucleic acid cleaving region of the wild-type RuvC domain of the CRISPR enzyme.

Here, the metal dependent nucleic acid cleaving region of the RuvC domain may mean a region capable of cleaving the binding between nucleic acids at a target location by interacting with the metal in the RuvC domain.

The metal dependent nucleic acid cleaving region may consist of a part interacting with a metal and a part capable of cleaving the binding between nucleic acids at a target location.

The third region may be a part of the wild-type CRISPR enzyme having the first function or the second function of the wild-type CRISPR enzyme.

The third region may be a region located in an NUC lobe of the wild-type CRISPR enzyme.

The third region may be all or a part of an HNH domain of the wild-type CRISPR enzyme.

The third region may be a part of an HNH domain including a metal dependent nucleic acid cleaving region of the HNH domain of the wild-type CRISPR enzyme.

Here, the metal dependent nucleic acid cleaving region of the HNH domain may mean a region capable of cleaving the binding between nucleic acids at a target location by interacting with a metal in the HNH domain.

The fourth region may be a part of the wild-type CRISPR enzyme that can recognize a specific nucleotide sequence, that is, a protospacer adjacent motif (PAM), in a target gene or nucleic acid.

The fourth region may be a part of the wild-type CRISPR enzyme, which interacts with a specific nucleotide sequence, that is, PAM, in a target gene or nucleic acid.

The fourth region may be a part of the wild-type CRISPR enzyme, which interacts with a part of the nucleotide sequence of gRNA.

The fourth region may be a region located in a NUC lobe of the wild-type CRISPR enzyme.

The fourth region may be all or a part of a PI domain of the wild-type CRISPR enzyme.

The artificially engineered CRISPR enzyme may be a CRISPR enzyme variant formed by modifying at least one amino acid in the amino acid sequence of one or more regions selected from the first region, the second region, the third region and the fourth region of the wild-type CRISPR enzyme.

The CRISPR enzyme variant may be in a form in which at least one amino acid in the amino acid sequence of the first region of the wild-type CRISPR enzyme is modified.

The CRISPR enzyme variant may be in a form in which at least one amino acid in the amino acid sequence of the second region of the wild-type CRISPR enzyme is modified.

The CRISPR enzyme variant may be in a form in which at least one amino acid in the amino acid sequence of the third region of the wild-type CRISPR enzyme is modified.

The CRISPR enzyme variant may be in a form in which at least one amino acid in the amino acid sequence of the fourth region of the wild-type CRISPR enzyme is modified.

The CRISPR enzyme variant may be in a form in which at least two amino acids in the amino acid sequences of the first region and the second region of the wild-type CRISPR enzyme are modified. Here, two or more amino acids may be present in different regions, respectively.

The CRISPR enzyme variant may be in a form in which at least two amino acids in the amino acid sequences of the first region and the third region of the wild-type CRISPR enzyme are modified. Here, two or more amino acids may be present in different regions, respectively.

The CRISPR enzyme variant may be in a form in which at least two amino acids in the amino acid sequences of the first region and the fourth region of the wild-type CRISPR enzyme are modified. Here, two or more amino acids may be present in different regions, respectively The CRISPR enzyme variant may be in a form in which at least two amino acids in the amino acid sequences of the second region and the third region of the wild-type CRISPR enzyme are modified. Here, two or more amino acids may be present in different regions, respectively.

The CRISPR enzyme variant may be in a form in which at least two amino acids in the amino acid sequences of the second region and the fourth region of the wild-type CRISPR enzyme. Here, the two or more amino acids may be present in different regions, respectively.

The CRISPR enzyme variant may be in a form in which at least two amino acids in the amino acid sequences of the third region and the fourth region of the wild-type CRISPR enzyme are modified. Here, the two or more amino acids may be present in different regions, respectively.

The CRISPR enzyme variant may be in a form in which at least three amino acids in the amino acid sequences of the first region, the second region and the third region of the wild-type CRISPR enzyme are modified. Here, the three or more amino acids may be present in different regions, respectively.

The CRISPR enzyme variant may be in a form in which at least three amino acids in the amino acid sequences of the first region, the second region and the fourth region of the wild-type CRISPR enzyme are modified. Here, the three or more amino acids may be present in different regions, respectively.

The CRISPR enzyme variant may be in a form in which at least three amino acids in the amino acid sequences of the first region, the third region and the fourth region of the wild-type CRISPR enzyme are modified. Here, the three or more amino acids may be present in different regions, respectively.

The CRISPR enzyme variant may be in a form in which at least three amino acids in the amino acid sequences of the second region, the third region and the fourth region of the wild-type CRISPR enzyme are modified. Here, the three or more amino acids may be present in different regions, respectively.

The CRISPR enzyme variant may be in a form in which at least four amino acids in the amino acid sequences of the first region, the second region, the third region and the fourth region of the wild-type CRISPR enzyme are modified. Here, the four or more amino acids may be present in different regions, respectively.

The CRISPR enzyme variant may include the modification of at least one amino acid selected from the one or more regions.

Here, the modification may be a deletion of the selected one or more amino acid.

Here, the modification may be a substitution of the selected one or more amino acids with different amino acids.

In one example, the different amino acid may be a stereoisomer of the selected amino acid.

For example, the modification may be a substitution of L-glutamine located in the first region of the wild-type CRISPR enzyme, with D-glutamine.

In another example, the different amino acid may be an amino acid having a lower hydropathy index than that of the selected amino acid.

For example, the modification may be a substitution of phenylalanine (hydropathy index: 2.8) located in the second region of the wild-type CRISPR enzyme, with glycine having a lower hydropathy index (−0.4).

In still another example, the different amino acid may be an amino acid having a higher hydropathy index than that of the selected amino acid.

For example, the modification may be a substitution of serine (hydropathy index: −0.8) located in the first region of the wild-type CRISPR enzyme, with leucine having a higher hydropathy index (3.8).

In one example, the different amino acid may be an amino acid having a smaller functional group than that of the selected amino acid.

For example, the modification may be a substitution of valine located in the third region of the wild-type CRISPR enzyme, with alanine having a smaller functional group than that of the valine.

In another example, the different amino acid may be an amino acid having a larger functional group than that of the selected amino acid.

For example, the modification may be a substitution of glycine located in the second region of the wild-type CRISPR enzyme, with histidine having a larger functional group than that of the glycine.

In one example, the different amino acid may be an amino acid having higher hydrophobicity than that of the selected amino acid.

For example, the modification may be a substitution of asparagine (Kyte-Doolittle hydrophobicity: −3.5) located in the first region of the wild-type CRISPR enzyme, with threonine (Kyte-Doolittle hydrophobicity: −0.7).

In another example, the different amino acid may be an amino acid having lower hydrophobicity than that of the selected amino acid.

For example, the modification may be a substitution of cysteine (Kyte-Doolittle hydrophobicity: 2.5) located in the fourth region of the wild-type CRISPR enzyme, with proline (Kyte-Doolittle hydrophobicity: −1.6).

In one example, the different amino acid may be an amino acid larger than the selected amino acid.

For example, the modification may be a substitution of lysine (molecular weight (m.w.): 146.189) located in the third region of the wild-type CRISPR enzyme, with tryptophan (m.w.: 204.228).

In another example, the different amino acid may be an amino acid smaller than the selected amino acid.

For example, the modification may be a substitution of phenylalanine (m.w.: 165.192) located in the second region of the wild-type CRISPR enzyme, with glutamic acid (m.w.: 147.131).

The modification may be a substitution of the selected one or more amino acids with the same number of other amino acids.

For example, the modification may be a substitution of one alanine located in the first region of the wild-type CRISPR enzyme, with one glycine. Alternatively, the modification may be a substitution of one arginine located in the first region and one histidine located in the fourth region of the wild-type CRISPR enzyme, with one leucine (the first region) and one serine (the fourth region), respectively. Alternatively, the modification may be a substitution of one arginine and one valine located in the second region and one leucine located in the third region of the wild-type CRISPR enzyme, with respective one phenylalanine, that is, a total of three phenylalanines.

The modification may be a substitution of the selected one or more amino acids with a different number of other amino acids.

For example, the modification may be a substitution of one leucine located in the second region of the wild-type CRISPR enzyme with cysteine-alanine-alanine, that is, a total of three amino acids. Alternatively, the modification may be a substitution of one histidine located in the first region and two contiguous amino acids, alanine-glutamine, located in the third region of the wild-type CRISPR enzyme, with methionine-valine (the first region) and proline (the third region), respectively. Alternatively, the modification may be a substitution of one glutamic acid located in the first region, three contiguous amino acids, alanine-leucine-histidine, located in the second region and two contiguous amino acids, tryptophan-serine, located in the third region of the wild-type CRISPR enzyme, with alanine (the first region), methionine-proline (the second region) and cysteine-alanine-threonine-valine (the third region), respectively.

The artificially engineered CRISPR enzyme may be a CRISPR enzyme variant formed by adding at least one amino acid into one or more regions selected from the first region, the second region, the third region and the fourth region of the wild-type CRISPR enzyme.

Here, the addition may be an addition of one or more amino acids to the N-terminal and/or C-terminal position(s) of one or more amino acids present in the selected one or more regions.

In one example, the addition may be an addition of one or more amino acids having a positively charge to the N-terminal and/or C-terminal position(s) of one or more amino acids present in the selected one or more regions.

For example, the addition may be to add one arginine to the C-terminus of the selected one alanine located in the first region. Alternatively, the addition may be to add two amino acids, histidine-lysine, to the N-terminus of the selected glutamic acid located in the third region.

In another example, the addition may be an addition of one or more amino acids having a negative charge to the N-terminal and/or C-terminal position(s) of one or more amino acids present in the selected one or more regions.

For example, the addition may be to add one aspartic acid to the N-terminus of the selected one threonine located in the second region. Alternatively, the addition may be to add three amino acids, glutamic acid-aspartic acid-glutamic acid, to the C-terminus of the selected histidine located in the fourth region.

In still another example, the addition may be an addition of one or more amino acids having no charge to the N-terminal and/or C-terminal position(s) of the one or more amino acids present in selected one or more regions.

For example, the addition may be to add two amino acids, serine-valine, to the C-terminus of the selected one cysteine located in the second region. Alternatively, the addition may be to add five amino acids, glycine-proline-glutamine-phenylalanine-leucine, to the N-terminus of the selected lysine located in the third region.

In another example, the addition may be an addition of one or more amino acids selected from positively-charged amino acids, negatively-charged amino acids and non-charged amino acids to the N-terminal and/or C-terminal position(s) of the one or more amino acids present in the selected one or more regions.

For example, the addition may be to add six amino acids, histidine-arginine-glycine-serine-alanine-glutamic acid, to the C-terminus of the selected one arginine located in the first region. Alternatively, the addition may be to add ten amino acids, lysine-lysine-alanine-phenylalanine-glutamine-threonine-methionine-cysteine-aspartic acid-serine, to the N-terminus of the selected one glycine located in the fourth region.

The addition may be an addition of one or more functional domains to the N-terminal and/or C-terminal position(s) of one or more amino acids present in the selected one or more regions.

Here, the functional domain may be a domain having an additional function, in addition to the original functions of the wild-type CRISPR enzyme, which are the first function of cleaving the first strand of the double-stranded DNA and the second function of cleaving the second strand thereof.

Alternatively, the functional domain may be a domain having a function similar to the original functions of the wild-type CRISPR enzyme, such as the first function of cleaving the first strand of the double-stranded DNA and the second function of cleaving the second strand thereof.

In one example, the functional domain may be a domain having methylase activity, demethylase activity, transcription activation activity, transcription repression activity, transcription release factor activity, histone modification activity, RNA cleavage activity or nucleic acid binding activity.

In another example, the functional domain may be a tag or a reporter gene for isolation and purification of a protein (including a peptide). Here, the tag includes a histidine (His) tag, a V5 tag, a FLAG tag, an influenza hemagglutinin (HA) tag, a Myc tag, a VSV-G tag and a thioredoxin (Trx) tag, etc., and the reporter gene includes glutathione-S-transferase (GST), horseradish peroxidase (HRP), chloramphenicol acetyltransferase (CAT), beta-galactosidase, beta-glucuronidase, luciferase, and autofluorescent proteins including a green fluorescent protein (GFP), HcRed, DsRed, a cyan fluorescent protein (CFP), a yellow fluorescent protein (YFP) and a blue fluorescent protein (BFP), but the present invention is not limited thereto.

In still another example, the functional domain may be a deaminase. Here, the deaminase may be a adenine deaminase and/or a cytidine deaminase.

In another example, the functional domain may be a nuclear localization sequence or signal (NLS) or a nuclear export sequence or signal (NES).

In one exemplary embodiment of the disclosure disclosed herein, the artificially engineered CRISPR enzyme may be an artificially engineered Cas9.

The artificially engineered Cas9 may be a Cas9 variant formed by modifying at least one amino acid in the amino acid sequence of a specific region of wild-type Cas9.

The artificially engineered Cas9 may be a Cas9 variant formed by adding at least one amino acid into a specific region of the wild-type Cas9.

Here, the specific region of the wild-type Cas9 may be one or more regions selected from a first region, a second region, a third region and a fourth region.

The first region may be a part of the wild-type Cas9 interacting with a gRNA.

The first region may be a part of the wild-type Cas9 interacting with a target sequence.

The first region may be a part of the wild-type Cas9 interacting with a gRNA-target sequence heteroduplex.

The first region may be a part of the wild-type Cas9 interacting with a PAM distal end of the gRNA-target sequence heteroduplex.

Here, the PAM distal end of the gRNA-target sequence heteroduplex may mean 6 to 10 base pairs at the end of the gRNA-target sequence heteroduplex far from the PAM location, which is a sequence of 6 to 10 bases of the gRNA and a 6 to 10 bases sequence of a target sequence complementarily binding thereto.

The first region may be a region located in a REC lobe of the wild-type Cas9.

The first region may be all or a part of a REC domain of the wild-type Cas9.

The first region may be a region consisting of 300 amino acids at the C-terminus of the REC domain of the wild-type Cas9.

The first region may be a region consisting of 220 amino acids at the N-terminus of the REC domain of the wild-type Cas9.

In one example, when the wild-type Cas9 is wild-type SpCas9 (SEQ ID NO: 1), the first region may be all or a part of the amino acid sequence from aspartic acid at $94^{th}$ position (D94) to glycine at $717^{th}$ position (G717) of the wild-type SpCas9.

In one exemplary embodiment, the first region may be the amino acid sequence (region 1-1, SEQ ID NO: 2) from phenylalanine at $196^{th}$ position (F196) to isoleucine at $282^{th}$ position (I282) of the wild-type SpCas9.

In another exemplary embodiment, the first region may be the amino acid sequence (region 1-2, SEQ ID NO: 3) from proline at $316^{th}$ position (P316) to asparagine at $394^{th}$ position (N394) of the wild-type SpCas9.

In still another exemplary embodiment, the first region may be the amino acid sequence (region 1-3, SEQ ID NO: 4) from lysine at $510^{th}$ position (K510) to asparagine at $612^{th}$ position (N612) of the wild-type SpCas9.

In yet another exemplary embodiment, the first region may be the amino acid sequence (region 1-4, SEQ ID NO: 5) from threonine at $678^{th}$ position (T678) to histidine at $698^{th}$ position (H698) of the wild-type SpCas9.

In one exemplary embodiment, the first region may be two regions selected from the amino acid sequence from phenylalanine at $196^{th}$ position (F196) to isoleucine at $282^{th}$ position (I282) of the wild-type SpCas9 (region 1-1), the amino acid sequence from proline at $316^{th}$ position (P316) to asparagine at $394^{th}$ position (N394) of the wild-type SpCas9 (region 1-2), the amino acid sequence from lysine at $510^{th}$ position (K510) to asparagine at $612^{th}$ position (N612) of the wild-type SpCas9 (region 1-3), and the amino acid sequence from threonine at $678^{th}$ position (T678) to histidine at $698^{th}$ position (H698) of the wild-type SpCas9 (region 1-4).

In another exemplary embodiment, the first region may be three regions selected from the amino acid sequence from phenylalanine at $196^{th}$ position (F196) to isoleucine at $282^{th}$ position (I282) of the wild-type SpCas9 (region 1-1), the amino acid sequence from proline at $316^{th}$ position (P316) to asparagine at $394^{th}$ position (N394) of the wild-type SpCas9 (region 1-2), the amino acid sequence from lysine at $510^{th}$ position (K510) to asparagine at $612^{th}$ position (N612) of the wild-type SpCas9 (region 1-3), and the amino acid sequence from threonine at $678^{th}$ position (T678) to histidine at $698^{th}$ position (H698) of the wild-type SpCas9 (region 1-4).

In still another exemplary embodiment, the first region may be the amino acid sequence from phenylalanine at $196^{th}$ position (F196) to isoleucine at $282^{th}$ position (I282) of the wild-type SpCas9 (region 1-1), the amino acid sequence from proline at $316^{th}$ position (P316) to asparagine at $394^{th}$ position (N394) of the wild-type SpCas9 (region 1-2), the amino acid sequence from lysine at $510^{th}$ position (K510) to asparagine at $612^{th}$ position (N612) of the wild-type SpCas9 (region 1-3), and the amino acid sequence from threonine at $678^{th}$ position (T678) to histidine at $698^{th}$ position (H698) of the wild-type SpCas9 (region 1-4).

In another example, when the wild-type Cas9 is wild-type SaCas9, the first region may be all or a part of the amino acid sequence from asparagine at $75^{th}$ position (N75) to lysine at $426^{th}$ position (K426) of the wild type SaCas9.

In one exemplary embodiment, the first region may be the amino acid sequence from threonine at $207^{th}$ position (T207) to lysine at $426^{th}$ position (K426) of the wild-type SaCas9.

The second region may be a part of the wild-type Cas9 having the first function or the second function of the wild-type Cas9.

The second region may be a region located in an NUC lobe of the wild-type Cas9.

The second region may be all or a part of a RuvC domain of the wild-type Cas9.

The second region may be a part of the RuvC domain including a metal dependent nucleic acid cleaving region of the wild-type Cas9.

Here, the metal dependent nucleic acid cleaving region of the RuvC domain may mean a region capable of cleaving the binding between nucleic acids at a target location by interacting with a metal in the RuvC domain.

The metal dependent nucleic acid cleaving region may consist of a part interacting with a metal and a part of cleaving the binding between nucleic acids at a target location.

In one example, when the wild-type Cas9 is wild-type SpCas9, the second region may be all or a part of the amino acid sequence (RuvC I region) from methionine at $1^{st}$ position (M1) to alanine at $59^{th}$ position (A59) of the wild-type SpCas9.

The second region may be all or a part of the amino acid sequence (RuvC II region) from aspartic acid at $718^{th}$ position (D718) to glutamine at $774^{th}$ position (Q774) of the wild-type SpCas9.

The second region may be all or a part of the amino acid sequence (RuvC III region) from serine at $909^{th}$ position (S909) to threonine at $1098^{th}$ position (T1098) of the wild-type SpCas9.

The second region may be the RuvC I region, the RuvC II region and/or the RuvC III region of the wild-type SpCas9.

In one exemplary embodiment, the second region may be the amino acid sequence (region 2-1, SEQ ID NO: 6) from methionine at $1^{st}$ position (M1) to threonine at $22^{th}$ position (T22) of the wild-type SpCas9.

In another exemplary embodiment, the second region may be the amino acid sequence (region 2-2, SEQ ID NO: 7) from proline at $731^{th}$ position (P731) to threonine at $770^{th}$ position (T770) of the wild-type SpCas9.

In still another exemplary embodiment, the second region may be the amino acid sequence (region 2-3, SEQ ID NO: 8) from glutamine at $926^{th}$ position (Q926) to serine at $1040^{th}$ position (S1040) of the wild-type SpCas9.

In exemplary embodiment, the second region may be the amino acid sequence from methionine at $1^{st}$ position (M1) to threonine at $22^{th}$ position (T22) of the wild-type SpCas9 (region 2-1) and the amino acid sequence from proline at $731^{th}$ position (P731) to threonine at $770^{th}$ position (T770) of the wild-type SpCas9 (region 2-2).

In another exemplary embodiment, the second region may be the amino acid sequence from methionine at $1^{st}$ position (M1) to threonine at $22^{th}$ position (T22) of the wild-type SpCas9 (region 2-1) and the amino acid sequence from glutamine at $926^{th}$ position (Q926) to serine at $1040^{th}$ position (S1040) of the wild-type SpCas9 (region 2-3).

In still another exemplary embodiment, the second region may be the amino acid sequence from proline at $731^{th}$ position (P731) to threonine at $770^{th}$ position (T770) of the wild-type SpCas9 (region 2-2) and the amino acid sequence from glutamine at $926^{th}$ position (Q926) to serine at $1040^{th}$ position (S1040) of the wild-type SpCas9 (region 2-3).

In yet another exemplary embodiment, the second region may be the amino acid sequence from methionine at $1^{st}$ position (M1) to threonine at $22^{th}$ position (T22) of the wild-type SpCas9 (region 2-1), the amino acid sequence from proline at $731^{th}$ position (P731) to threonine at $770^{th}$ position (T770) of the wild-type SpCas9 (region 2-2), and the amino acid sequence from glutamine at $926^{th}$ position (Q926) to serine at $1040^{th}$ position (S1040) of the wild-type SpCas9 (region 2-3).

In another example, when the wild-type Cas9 is a wild-type SaCas9, the second region may be all or a part of the amino acid sequence (RuvC I region) from methionine at $1^{st}$ position (M1) to valine at $41^{th}$ position (V41) of the wild type SaCas9.

The second region may be all or a part of the amino acid sequence (RuvC II region) from isoleucine at $436^{th}$ position (I436) to glutamic acid at $481^{th}$ position (E481) of the wild-type SaCas9.

The second region may be all or a part of the amino acid sequence (RuvC III region) from tyrosine at $651^{th}$ position (Y651) to valine at $775^{th}$ position (V775) of the wild type SaCas9.

The second region may be the RuvC I region, the RuvC II region and/or the RuvC III region of the wild-type SaCas9.

In one exemplary embodiment, the second region may be the amino acid sequence (region 2-1) from methionine at $1^{st}$ position (M1) to threonine at $25^{th}$ position (T25) of the wild type SaCas9.

In another exemplary embodiment, the second region may be the amino acid sequence (region 2-2) from proline at $471^{th}$ position (P471) to glutamic acid at $481^{th}$ position (E481) of the amino acid sequence of the wild-type SaCas9.

In still another exemplary embodiment, the second region may be the amino acid sequence (region 2-3) from asparagine at $667^{th}$ position (N667) to serine at $740^{th}$ position (S740) of the wild-type SaCas9.

The third region may be a part of the wild-type Cas9 having the first function or the second function thereof.

The third region may be a region located in an NUC lobe of the wild-type Cas9.

The third region may be all or a part of an HNH domain of the wild-type Cas9.

The third region may be all or a part of an HNH domain including a metal dependent nucleic acid cleaving region of the wild-type Cas9.

Here, the metal dependent nucleic acid cleaving region of the HNH domain may mean a region that can cleave nucleic acids at a target location by interacting with a metal in the HNH domain.

In one example, when the wild-type Cas9 is a wild-type SpCas9, the third region may be all or a part of the amino acid sequence from lysine at $775^{th}$ position (K775) to leucine at $908^{th}$ position (L908) of the wild-type SpCas9.

In one exemplary embodiment, the third region may be the amino acid sequence (region 3-1, SEQ ID NO: 9) from lysine at $775^{th}$ position (K775) to leucine at $900^{th}$ position (L900) of the wild-type SpCas9.

In another example, when the wild-type Cas9 is a wild-type SaCas9, the third region may be all or a part of the amino acid sequence from isoleucine at $521^{th}$ position (I521) to glutamic acid at $629^{th}$ position (E629) of the wild-type SaCas9.

In one exemplary embodiment, the third region may be the amino acid sequence (region 3-1) from lysine at $523^{th}$ position (K523) to leucine at $627^{th}$ position (L627) of the wild type SaCas9.

The fourth region may be a part of the wild-type Cas9 which can recognize a specific nucleotide sequence, that is, PAM, in a target gene or nucleic acid.

The fourth region may be a part of the wild-type Cas9 interacting with a specific nucleotide sequence, that is, PAM, in a target gene or nucleic acid.

The fourth region may be a part of the wild-type Cas9 interacting with a part of the nucleotide sequence of gRNA.

The fourth region may be a region located in an NUC lobe of the wild-type Cas9.

The fourth region may be all or a part of a PI domain of the wild-type Cas9.

In one example, when the wild-type Cas9 is a wild-type SpCas9, the fourth region may be all or a part of the amino acid sequence from glutamic acid at $1099^{th}$ position (E1099) to aspartic acid at $1368^{th}$ position (D1368) of the wild-type SpCas9.

In one exemplary embodiment, the fourth region may be the amino acid sequence (region 4-1, SEQ ID NO: 10) from glutamic acid at $1099^{th}$ position (E1099) to valine at $1139^{th}$ position (V1139) of the wild-type SpCas9.

In another example, when the wild-type Cas9 is a wild-type SaCas9, the fourth region may be all or a part of the amino acid sequence from lysine at $910^{th}$ position (K910) to glycine at $1053^{th}$ position (G1053) of the wild type SaCas9.

In one exemplary embodiment, the fourth region may be the amino acid sequence (region 4-1) from lysine at $910^{th}$ position (K910) to aspartic acid at $970^{th}$ position (D970) of the wild type SaCas9.

The artificially engineered Cas9 may be a Cas9 variant formed by modifying at least one amino acid in the amino acid sequence of one or more regions selected from the first region, the second region, the third region and the fourth region of the wild-type Cas9.

The Cas9 variant may be in a form in which one or more amino acids selected from the amino acid sequence of the first region of the wild-type Cas9 are modified.

In one example, when the wild-type Cas9 is a wild-type SpCas9, a SpCas9 variant may be in a form in which one or more amino acids selected from the amino acid sequence of the first region of the wild-type SpCas9 is modified.

In one exemplary embodiment, the SpCas9 variant may be in a form in which one or more amino acids selected from the amino acid sequence of the region 1-1 of the wild-type SpCas9 are modified.

For example, the SpCas9 variant may be a form with a modification of one or more amino acids selected from N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281 and I282 which are amino acids having an aliphatic or amide-based functional group of the region 1-1 of the wild-type SpCas9.

In another exemplary embodiment, the SpCas9 variant may be in a form in which one or more amino acids selected from the amino acid sequence of the region 1-2 of the wild-type SpCas9 are modified.

For example, the SpCas9 variant may be a form with a modification of one or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 which are non-polar amino acids of the region 1-2 of the wild-type SpCas9.

In one exemplary embodiment, the SpCas9 variant may be in a form in which one or more amino acids selected from the amino acid sequence of the region 1-3 of the wild-type SpCas9 are modified.

For example, the SpCas9 variant may be a form with a modification of one or more amino acids selected from the group consisting of K510, Y515, F539, G582, V583, E584, D585, N588 and I601 of the region 1-3 of the wild-type SpCas9.

For example, the SpCas9 variant may be a form with a modification of one or more amino acids selected from the group consisting of L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 which are non-polar amino acids of the region 1-3 of the wild-type SpCas9.

In another exemplary embodiment, the SpCas9 variant may be in a form in which one or more amino acids selected from the amino acid sequence of the region 1-4 of the wild-type SpCas9 are modified.

For example, the SpCas9 variant may be a form with a modification of one or more amino acids selected from the group consisting of N692, M694, Q695 and H698 of the region 1-4 of the wild-type SpCas9.

For example, the SpCas9 variant may be a form with a modification of one or more amino acids selected from the group consisting of non-polar amino acids, that is, I679, L680, F682, L683, G687, F688, A689, F693, M694, L696 and I697 of the region 1-4 of the wild-type SpCas9.

In still another exemplary embodiment, the SpCas9 variant may be in a form in which two or more amino acids selected from the amino acid sequences of the region 1-1, the region 1-2, the region 1-3 and the region 1-4 of the wild-type SpCas9 are modified. Here, the selected two or more amino acids may be located in different regions, respectively. Alternatively, the selected two or more amino acids may be located in the same region.

For example, the SpCas9 variant may be a form with a modification of two or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the region 1-1, the region 1-2, the region 1-3 and the region 1-4 of the wild-type SpCas9.

For example, the SpCas9 variant may be a form with a modification of two or more amino acids selected from the group consisting of A203, N277, G366, K510, Y515, F539, G582, V583, E584, D585, N588, I601, N692, M694, Q695 and H698 of the region 1-1, the region 1-2, the region 1-3 and the region 1-4 of the wild-type SpCas9.

For example, the SpCas9 variant may be a form with a modification of two or more amino acids selected from the group consisting of K510, Y515, F539, G582, V583, E584, D585, N588, I601, N692, M694, Q695 and H698 of the region 1-3 and the region 1-4 of the wild-type SpCas9.

For example, the SpCas9 variant may be a form with a modification of two or more amino acids selected from the group consisting of non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the region 1-3 and the region 1-4 of the wild-type SpCas9.

In another exemplary embodiment, the SpCas9 variant may be in a form in which three or more amino acids selected from the amino acid sequences of the region 1-1, the region 1-2, the region 1-3 and the region 1-4 of the wild-type SpCas9 are modified. Here, the selected three or more amino acids may be located in different regions, respectively. Alternatively, the selected three or more amino acids may be located in the same region. Alternatively, the selected three or more amino acids may be located in the same or different regions, respectively.

For example, the SpCas9 variant may be a form with a modification of three or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9.

For example, the SpCas9 variant may be a form with a modification of three or more amino acids selected from the group consisting of A203, N277, G366, K510, Y515, F539, G582, V583, E584, D585, N588, I601, N692, M694, Q695 and H698 of the region 1-1, the region 1-2, the region 1-3 and the region 1-4 of the wild-type SpCas9.

For example, the SpCas9 variant may be a form with a modification of three or more amino acids selected from the group consisting of A203, N277, K510, Y515, F539, G582, V583, E584, D585, N588, I601, N692, M694, Q695 and H698 of the region 1-1, the region 1-3 and the region 1-4 of the wild-type SpCas9.

For example, the SpCas9 variant may be a form with a modification of three or more amino acids selected from the group consisting of G366, K510, Y515, F539, G582, V583, E584, D585, N588, I601, N692, M694, Q695 and H698 of the region 1-2, the region 1-3 and the region 1-4 of the wild-type SpCas9.

The Cas9 variant may be in a form in which one or more amino acids selected from the amino acid sequence of the second region of the wild-type Cas9 are modified.

In one example, when the wild-type Cas9 is a wild-type SpCas9, a SpCas9 variant may be in a form in which one or more amino acids selected from the amino acid sequence of the second region of the wild-type SpCas9 are modified.

In one exemplary embodiment, the SpCas9 variant may be in a form in which one or more amino acids selected from the amino acid sequence of the region 2-1 of the wild-type SpCas9 are modified.

For example, the SpCas9 variant may be a form with a modification of one or more amino acids selected from the group consisting of I7, G8, L9, D10, I11 and G12 of the region 2-1 of the wild-type SpCas9.

For example, the SpCas9 variant may be a form with a modification of one or more amino acids selected from the group consisting of the non-polar amino acids, that is, I7, G8, L9, I11, G12, V16, G17, W18, A19, V20 and I21 of the region 2-1 of the wild-type SpCas9.

In another exemplary embodiment, the SpCas9 variant may be in a form in which one or more amino acids selected from the amino acid sequence of the region 2-2 of the wild-type SpCas9 are modified.

For example, the SpCas9 variant may be a form with a modification of one or more amino acids selected from the group consisting of I761, E762, M763, R765, E766 and N767 of the region 2-2 of the wild-type SpCas9.

For example, the SpCas9 variant may be a form with a modification of one or more amino acids selected from the group consisting of the non-polar amino acids, that is, P731, A732, I733, G736, I737, L738, V741, V743, V744, L747, V748, V750, M751, G752, P756, I759, V760, I761, M763 and A764 in the region 2-2 of the wild-type SpCas9.

In still another exemplary embodiment, the SpCas9 variant may be in a form in which one or more amino acids selected from the amino acid sequence of the region 2-3 of the wild-type SpCas9 are modified.

For example, the SpCas9 variant may be a form with a modification of one or more amino acids selected from the group consisting of D965, Y981, H982, H983, A984, H985, D986, A987, Y988, Y1036, F1037, F1038 and Y1039 of the region 2-3 of the wild-type SpCas9.

For example, the SpCas9 variant may be a form with a modification of one or more amino acids selected from the group consisting of the non-polar amino acids, that is, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-3 of the wild-type SpCas9.

In one exemplary embodiment, the SpCas9 variant may be in a form in which two or more amino acids selected from the amino acid sequences of the region 2-1 and the region 2-2 of the wild-type SpCas9 are modified. Here, the selected two or more amino acids may be located in the region 2-1 and the region 2-2, respectively.

For example, the SpCas9 variant may be a form with modifications of two or more amino acids selected from the group consisting of I7, G8, L9, D10, I11, G12, I761, E762, M763, R765, E766 and N767 of the region 2-1 and the region 2-2 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20, I21, P731, A732, I733, G736, I737, L738, V741, V743, V744, L747, V748, V750, M751, G752, P756, I759, V760, I761, M763 and A764 of the region 2-1 and the region 2-2 of the wild-type SpCas9.

In another exemplary embodiment, the SpCas9 variant may be in a form in which two or more amino acids selected from the amino acid sequence of the region 2-1 and the region 2-3 of the wild-type SpCas9 are modified. Here, the selected two or more amino acids may be located in the region 2-1 and the region 2-3, respectively.

For example, the SpCas9 variant may be a form including modifications of two or more amino acids selected from the group consisting of I7, G8, L9, D10, I11, G12, D965, Y981, H982, H983, A984, H985, D986, A987, Y988, Y1036, F1037, F1038 and Y1039 of the region 2-1 and the region 2-3 of the wild-type SpCas9.

For example, the SpCas9 variant may be a form with modifications of two or more amino acids selected from the group consisting of non-polar amino acids, that is, I7, G8, L9, I11, G12, V16, G17, W18, A19, V20, I21, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-1 and the region 2-3 of the wild-type SpCas9.

In still another exemplary embodiment, the SpCas9 variant may be in a form in which two or more amino acids selected from the amino acid sequences of the regions 2-2 and 2-3 of the wild-type SpCas9 are modified. Here, the selected two or more amino acids may be located in the region 2-2 and the region 2-3, respectively.

For example, the SpCas9 variant may be a form with modifications of two or more amino acids selected from the group consisting of I761, E762, M763, R765, E766, N767, D965, Y981, H982, H983, A984, H985, D986, A987, Y988, Y1036, F1037, F1038 and Y1039 of the region 2-2 and the region 2-3 of the wild-type SpCas9.

For example, the SpCas9 variant may be a form including modifications of two or more amino acids selected from the group consisting of the non-polar amino acids, that is, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-2 and the region 2-3 of the wild-type SpCas9.

In another exemplary embodiment, the SpCas9 variant may be in a form in which three or more amino acids selected from the amino acid sequences of the region 2-1, the region 2-2 and the region 2-3 of the wild-type SpCas9 are modified. Here, the selected three or more amino acids may be located in the region 2-1, the region 2-2 and the region 2-3 of the wild-type SpCas9, respectively.

For example, the SpCas9 variant may be a form with modifications of three or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the region 2-1, the region 2-2 and the region 2-3 of the wild-type SpCas9.

For example, the SpCas9 variant may be a form including modifications of three or more amino acids selected from the group consisting of the non-polar amino acids, that is, I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-1, the region 2-2 and the region 2-3 of the wild-type SpCas9.

The Cas9 variant may be in a form in which at least one amino acid of the amino acid sequence of the third region of the wild-type Cas9 is modified.

In one example, when the wild-type Cas9 is a wild-type SpCas9, a SpCas9 variant may be in a form in which one or more amino acids selected from the amino acid sequence in the third region of the wild-type SpCas9 are modified.

In one exemplary embodiment, the SpCas9 variant may be in a form in which one or more amino acids selected from the amino acid sequence of the region 3-1 of the wild-type SpCas9 are modified.

For example, the SpCas9 variant may be a form including a modification of one or more amino acids selected from the group consisting of V838, D839, H840, D853, N854, K855, K862, N863, R864, A889, K890 and L891 of the region 3-1 of the wild-type SpCas9.

For example, the SpCas9 variant may be a form with a modification of one or more amino acids selected from the group consisting of charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1 of the wild-type SpCas9.

The Cas9 variant may be in a form in which one or more amino acids selected from the amino acid sequence of the fourth region of the wild-type Cas9 are modified.

In one example, when the wild-type Cas9 is a wild-type SpCas9, a SpCas9 variant may be in a form in which one or more amino acids selected from the amino acid sequence of the fourth region of the wild-type SpCas9 are modified.

In one exemplary embodiment, the SpCas9 variant may be in a form in which one or more amino acids selected from the amino acid sequence in the region 4-1 of the wild-type SpCas9 are modified.

For example, the SpCas9 variant may be a form with a modification of one or more amino acids selected from the group consisting of T1102, S1106, E1108, S1116, D1117, D1125, D1127, D1135, S1136 and T1138 of the region 4-1 of the wild-type SpCas9.

The Cas9 variant may be in a form in which two or more amino acids selected from the amino acid sequence in the first region and the second region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence in the first region and the second region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 1-1 and the region 2-1 of the wild-type SpCas9 are modified.

For example, the SpCas9 variant may be a form with modifications of two or more amino acids selected from the group consisting of I7, G8, L9, D10, I11, G12, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281 and I282 of the region 1-1 and the region 2-1 of the wild-type SpCas9.

In another exemplary embodiment, the SpCas9 variant may be in a form in which two or more amino acids selected from the amino acid sequence of the region 1-1 and the region 2-2 of the wild-type SpCas9 are modified.

For example, the SpCas9 variant may be a form including modifications of two or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, I761, E762, M763, R765, E766 and N767 of the region 1-1 and the region 2-2 of the wild-type SpCas9.

In still another exemplary embodiment, the SpCas9 variant may be in a form in which two or more amino acids selected from the amino acid sequence of the region 1-1 and the region 2-3 of the wild-type SpCas9 are modified.

For example, the SpCas9 variant may be a form with modifications of two or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, D965, Y981, H982, H983, A984, H985, D986, A987, Y988, Y1036, F1037, F1038 and Y1039 of the region 1-1 and the region 2-3 of the wild-type SpCas9.

In one exemplary embodiment, the SpCas9 variant may be in a form in which two or more amino acids selected from the amino acid sequence of the region 1-2 and the region 2-1 of the wild-type SpCas9 are modified.

For example, the SpCas9 variant may be a form with modifications of two or more amino acids selected from the group consisting of I7, G8, L9, D10, I11, G12, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 of the region 1-2 and the region 2-1 of the wild-type SpCas9.

For example, the SpCas9 variant may be a form including modifications of two or more amino acids selected from the group consisting of the non-polar amino acids, that is, I7, G8, L9, I11, G12, V16, G17, W18, A19, V20, I21, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 of the region 1-2 and the region 2-1 of the wild-type SpCas9.

In another exemplary embodiment, the SpCas9 variant may be in a form in which two or more amino acids selected from the amino acid sequence of the region 1-2 and the region 2-2 of the wild-type SpCas9 are modified.

For example, the SpCas9 variant may be a form with modifications of two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, I761, E762, M763, R765, E766 and N767 of the region 1-2 and the region 2-2 of the wild-type SpCas9.

In still another exemplary embodiment, the SpCas9 variant may be in a form in which two or more amino acids selected from the amino acid sequence of the region 1-2 and the region 2-3 of the wild-type SpCas9 are modified.

For example, the SpCas9 variant may be a form with modifications of two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, D965, Y981, H982, H983, A984, H985, D986, A987, Y988, Y1036, F1037, F1038 and Y1039 of the region 1-2 and the region 2-3 of the wild-type SpCas9.

In one exemplary embodiment, the SpCas9 variant may be in a form in which two or more amino acids selected from the amino acid sequence of the region 1-3 and the region 2-1 of the wild-type SpCas9 are modified.

For example, the SpCas9 variant may be a form including modifications of two or more amino acids selected from the group consisting of I7, G8, L9, D10, I11, G12, K510, Y515, F539, G582, V583, E584, D585, N588 and I601 of the region 1-3 and the region 2-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20, I21, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 of the region 1-3 and the region 2-1 of the wild-type SpCas9.

In another exemplary embodiment, the SpCas9 variant may be in a form in which two or more amino acids selected from the amino acid sequence of the region 1-3 and the region 2-2 of the wild-type SpCas9 are modified.

For example, the SpCas9 variant may be a form with modifications of two or more amino acids selected from the group consisting of K510, Y515, F539, G582, V583, E584, D585, N588, I601, I761, E762, M763, R765, E766 and N767 of the region 1-3 and the region 2-2 of the wild-type SpCas9.

For example, the SpCas9 variant may be a form including modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, P731, A732, I733, G736, I737, L738, V741, V743, V744, L747, V748, V750, M751, G752, P756, I759, V760, I761, M763 and A764 of the region 1-3 and the region 2-2 of the wild-type SpCas9.

In still another exemplary embodiment, the SpCas9 variant may be in a form in which two or more amino acids selected from the amino acid sequence of the region 1-3 and the region 2-3 of the wild-type SpCas9 are modified.

For example, the SpCas9 variant may be a form with modifications of two or more amino acids selected from the group consisting of K510, Y515, F539, G582, V583, E584, D585, N588, I601, D965, Y981, H982, H983, A984, H985, D986, A987, Y988, Y1036, F1037, F1038 and Y1039 of the region 1-3 and the region 2-3 of the wild-type SpCas9.

For example, the SpCas9 variant may be a form including modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 1-3 and the region 2-3 of the wild-type SpCas9.

In one exemplary embodiment, the SpCas9 variant may be in a form in which two or more amino acids selected from the amino acid sequence of the region 1-4 and the region 2-1 of the wild-type SpCas9 are modified.

For example, the SpCas9 variant may be a form including modifications of two or more amino acids selected from the group consisting of I7, G8, L9, D10, I11, G12, N692, M694, Q695 and H698 of the region 1-4 and the region 2-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20, I21, I679, L680, F682, L683, G687, F688, A689, F693, M694, L696 and I697 of the region 1-4 and the region 2-1 of the wild-type SpCas9.

In another exemplary embodiment, the SpCas9 variant may be in a form in which two or more amino acids selected from the amino acid sequence of the region 1-4 and the region 2-2 of the wild-type SpCas9 are modified.

For example, the SpCas9 variant may be a form including modifications of two or more amino acids selected from the group consisting of N692, M694, Q695, H698, I761, E762, M763, R765, E766 and N767 of the region 1-4 and the region 2-2 of the wild-type SpCas9.

For example, the SpCas9 variant may be a form with modifications of two or more amino acids selected from the group consisting of the non-polar amino acids, that is, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763 and A764 of the region 1-4 and the region 2-2 of the wild-type SpCas9.

In still another exemplary embodiment, the SpCas9 variant may be in a form in which two or more amino acids selected from the amino acid sequence of the region 1-4 and the region 2-3 of the wild-type SpCas9 are modified.

For example, the SpCas9 variant may be a form including modifications of two or more amino acids selected from the group consisting of N692, M694, Q695, H698, D965, Y981, H982, H983, A984, H985, D986, A987, Y988, Y1036, F1037, F1038 and Y1039 of the region 1-4 and the region 2-3 of the wild-type SpCas9.

For example, the SpCas9 variant may be a form with modifications of two or more amino acids selected from the group consisting of the non-polar amino acids, that is, I679, L680, F682, L683, G687, F688, A689, F693, M694, L696, I697, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 1-4 and the region 2-3 of the wild-type SpCas9.

In one exemplary embodiment, the SpCas9 variant may be in a form in which two or more amino acids selected from the amino acid sequence of the first region and the second region of the wild-type SpCas9 are modified.

Here, the first region may be the region 1-1, the region 1-2, the region 1-3 and the region 1-4.

Here, the second region may be the region 2-1, the region 2-2 and the region 2-3.

For example, the SpCas9 variant may be a form with modifications of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, D965, Y981, H982, H983, A984, H985, D986, A987, Y988, Y1036, F1037, F1038 and Y1039 of the first region and the second region of the wild-type SpCas9.

For example, the SpCas9 variant may be a form with modifications of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the first region and the second region of the wild-type SpCas9.

The Cas9 variant may be in a form in which two or more amino acids selected from the amino acid sequence of the first region and the third region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the first region and the third region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 1-1 and the region 3-1 of the wild-type SpCas9 are modified.

For example, the SpCas9 variant may be a form with modifications of two or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, V838, D839, H840, D853, N854, K855, K862, N863, R864, A889, K890 and L891 of the region 1-1 and the region 3-1 of the wild-type SpCas9.

In one exemplary embodiment, the SpCas9 variant may be in a form in which two or more amino acids selected from the amino acid sequence of the region 1-2 and the region 3-1 of the wild-type SpCas9 are modified.

For example, the SpCas9 variant may be a form with modifications of two or more amino acids selected from the group consisting of the non-polar amino acids, that is, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 of the region 1-2 of the wild-type SpCas9; and charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In one exemplary embodiment, the SpCas9 variant may be in a form in which two or more amino acids selected from the amino acid sequence of the region 1-3 and the region 3-1 of the wild-type SpCas9 are modified.

For example, the SpCas9 variant may be a form with modifications of two or more amino acids selected from the group consisting of K510, Y515, F539, G582, V583, E584, D585, N588, I601, V838, D839, H840, D853, N854, K855, K862, N863, R864, A889, K890 and L891 of the region 1-3 and the region 3-1 of the wild-type SpCas9.

For example, the SpCas9 variant may be a form with modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 of the region 1-3 of the wild-type SpCas9; and the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In another exemplary embodiment, the SpCas9 variant may be in a form in which two or more amino acids selected from the amino acid sequence of the region 1-4 and the region 3-1 of the wild-type SpCas9 are modified.

For example, the SpCas9 variant may be a form with modifications of two or more amino acids selected from the group consisting of N692, M694, Q695, H698, V838, D839, H840, D853, N854, K855, K862, N863, R864, A889, K890 and L891 of the region 1-4 and the region 3-1 of the wild-type SpCas9.

For example, the SpCas9 variant may be a form with modifications of two or more amino acids selected from the group consisting of the non-polar amino acids, that is, I679, L680, F682, L683, G687, F688, A689, F693, M694, L696 and I697 of the region 1-4 of the wild-type SpCas9; and the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In one exemplary embodiment, the SpCas9 variant may be in a form in which two or more amino acids selected from the amino acid sequence of the first region and the third region of the wild-type SpCas9 are modified.

Here, the first region may be the region 1-1, the region 1-2, the region 1-3 and the region 1-4.

Here, the third region may be the region 3-1.

For example, the SpCas9 variant may be a form with modifications of two or more amino acids selected from the group consisting of A203, N277, G366, K510, Y515, F539, G582, V583, E584, D585, N588, I601, N692, M694, Q695, H698, V838, D839, H840, D853, N854, K855, K862, N863, R864, A889, K890 and L891 of the first region and the third region of the wild-type SpCas9.

For example, the SpCas9 variant may be a form with modifications of two or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the first region and the third region of the wild-type SpCas9.

The Cas9 variant may be in a form in which two or more amino acids selected from the amino acid sequence of the first region and the fourth region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the first region and the fourth region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 1-1 and the region 4-1 of the wild-type SpCas9 are modified.

For example, the SpCas9 variant may be a form with modifications of two or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, T1102, S1106, E1108, S1116, D1117, D1125, D1127, D1135, S1136 and T1138 of the region 1-1 and the region 4-1 of the wild-type SpCas9.

In one exemplary embodiment, the SpCas9 variant may be in a form in which two or more amino acids selected from the amino acid sequence of the region 1-2 and the region 4-1 of the wild-type SpCas9 are modified.

For example, the SpCas9 variant may be a form with modifications of two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, T1102, S1106, E1108, S1116, D1117, D1125, D1127, D1135, S1136 and T1138 of the region 1-2 and the region 4-1 of the wild-type SpCas9.

In one exemplary embodiment, the SpCas9 variant may be in a form in which two or more amino acids selected from the amino acid sequence of the region 1-3 and the region 4-1 of the wild-type SpCas9 are modified.

For example, the SpCas9 variant may be a form with modifications of two or more amino acids selected from the group consisting of K510, Y515, F539, G582, V583, E584, D585, N588, I601, T1102, S1106, E1108, S1116, D1117, D1125, D1127, D1135, S1136 and T1138 of the region 1-3 and the region 4-1 of the wild-type SpCas9.

For example, the SpCas9 variant may be a form with modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 of the region 1-3 of the wild-type SpCas9; and T1102, S1106, E1108, S1116, D1117, D1125, D1127, D1135, S1136 and T1138 of the region 4-1 of the wild-type SpCas9.

In another exemplary embodiment, the SpCas9 variant may be in a form in which two or more amino acids selected from the amino acid sequence of the region 1-4 and the region 4-1 of the wild-type SpCas9 are modified.

For example, the SpCas9 variant may be a form with modifications of two or more amino acids selected from the group consisting of N692, M694, Q695, H698, T1102, S1106, E1108, S1116, D1117, D1125, D1127, D1135, S1136 and T1138 of the region 1-4 and the region 4-1 of the wild-type SpCas9.

For example, the SpCas9 variant may be a form with modifications of two or more amino acids selected from the group consisting of the non-polar amino acids, that is, I679, L680, F682, L683, G687, F688, A689, F693, M694, L696 and I697 of the regions 1-4 of the wild-type SpCas9; and T1102, S1106, E1108, S1116, D1117, D1125, D1127, D1135, S1136 and T1138 of the region 4-1 of the wild-type SpCas9.

In one exemplary embodiment, the SpCas9 variant may be in a form in which two or more amino acids selected from the amino acid sequence of the first region and the fourth region of the wild-type SpCas9 are modified.

Here, the first region may be the region 1-1, the region 1-2, the region 1-3 and the region 1-4.

Here, the fourth region may be the region 4-1.

For example, the SpCas9 variant may be a form with modifications of two or more amino acids selected from the group consisting of A203, N277, G366, K510, Y515, F539, G582, V583, E584, D585, N588, I601, N692, M694, Q695, H698, T1102, S1106, E1108, S1116, D1117, D1125, D1127, D1135, S1136 and T1138 of the first region and the fourth region of the wild-type SpCas9.

For example, the SpCas9 variant may be a form with modifications of two or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, T1102, S1106, E1108, S1116, D1117, D1125, D1127, D1135, S1136 and T1138 of the first region and the fourth region of the wild-type SpCas9.

The Cas9 variant may be in a form in which two or more amino acids selected from the amino acid sequence of the second region and the third region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the second region and the third region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 2-1 and the region 3-1 of the wild-type SpCas9 are modified.

For example, the SpCas9 variant may be a form with modifications of two or more amino acids selected from the group consisting of I7, G8, L9, D10, I11, G12, V838, D839, H840, D853, N854, K855, K862, N863, R864, A889, K890 and L891 of the region 2-1 and the region 3-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20 and I21 of the region 2-1 of the wild-type SpCas9; and charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In another exemplary embodiment, the SpCas9 variant may be in a form in which two or more amino acids selected from the amino acid sequence of the region 2-2 and the region 3-1 of the wild-type SpCas9 are modified.

For example, the SpCas9 variant may be a form with modifications of two or more amino acids selected from the group consisting of I761, E762, M763, R765, E766, N767, V838, D839, H840, D853, N854, K855, K862, N863, R864, A889, K890 and L891 of the region 2-2 and the region 3-1 of the wild-type SpCas9.

For example, the SpCas9 variant may be a form with modifications of two or more amino acids selected from the group consisting of the non-polar amino acids, that is, P731, A732, I733, G736, I737, L738, V741, V743, V744, L747, V748, V750, M751, G752, P756, I759, V760, I761, M763 and A764 of the region 2-2 of the wild-type SpCas9; and the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In still another exemplary embodiment, the SpCas9 variant may be in a form in which two or more amino acids selected from the amino acid sequence of the region 2-3 and the region 3-1 of the wild-type SpCas9 are modified.

For example, the SpCas9 variant may be a form with modifications of two or more amino acids selected from the group consisting of V838, D839, H840, D853, N854, K855, K862, N863, R864, A889, K890, L891, D965, Y981, H982, H983, A984, H985, D986, A987, Y988, Y1036, F1037, F1038 and Y1039 of the region 2-3 and the region 3-1 of the wild-type SpCas9.

For example, the SpCas9 variant may be a form with modifications of two or more amino acids selected from the group consisting of the non-polar amino acids, that is, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-3 of the wild-type SpCas9; and charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In one exemplary embodiment, the SpCas9 variant may be in a form in which two or more amino acids selected from the amino acid sequence of the second region and the third region of the wild-type SpCas9 are modified.

Here, the second region may be the region 2-1, the region 2-2 and the region 2-3.

Here, the third region may be the region 3-1.

For example, the SpCas9 variant may be a form with modifications of two or more amino acids selected from the group consisting of I7, G8, L9, D10, I11, G12, I761, E762, M763, R765, E766, N767, V838, D839, H840, D853, N854, K855, K862, N863, R864, A889, K890, L891, Y981, H982, H983, A984, H985, D965, D986, A987, Y988, Y1036, F1037, F1038 and Y1039 of the second region and the third region of the wild-type SpCas9.

For example, the SpCas9 variant may be a form with modifications of two or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the second region and the third region of the wild-type SpCas9.

The Cas9 variant may be in a form in which two or more amino acids selected from the amino acid sequence of the second region and the fourth region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the second region and the fourth region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 2-1 and the region 4-1 of the wild-type SpCas9 are modified.

For example, the SpCas9 variant may be a form with modifications of two or more amino acids selected from the group consisting of I7, G8, L9, D10, I11, G12, T1102, S1106, E1108, S1116, D1117, D1125, D1127, D1135, S1136 and T1138 of the region 2-1 and the region 4-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20 and I21 of the region 2-1 of the wild-type SpCas9; and T1102, S1106, E1108, S1116, D1117, D1125, D1127, D1135, S1136 and T1138 of the region 4-1 of the wild-type SpCas9.

In another exemplary embodiment, the SpCas9 variant may be in a form in which two or more amino acids selected from the amino acid sequence of the region 2-2 and the region 4-1 of the wild-type SpCas9 are modified.

For example, the SpCas9 variant may be a form with modifications of two or more amino acids selected from the group consisting of I761, E762, M763, R765, E766, N767, T1102, S1106, E1108, S1116, D1117, D1125, D1127, D1135, S1136 and T1138 of the region 2-2 and the region 4-1 of the wild-type SpCas9.

For example, the SpCas9 variant may be a form with modifications of two or more amino acids selected from the group consisting of the non-polar amino acids, that is, P731, A732, I733, G736, I737, L738, V741, V743, V744, L747, V748, V750, M751, G752, P756, I759, V760, I761, M763 and A764 of the region 2-2 of the wild-type SpCas9; and T1102, S1106, E1108, S1116, D1117, D1125, D1127, D1135, S1136 and T1138 of the region 4-1 of the wild-type SpCas9.

In still another exemplary embodiment, the SpCas9 variant may be in a form in which two or more amino acids selected from the amino acid sequence of the region 2-3 and the region 4-1 of the wild-type SpCas9 are modified.

For example, the SpCas9 variant may be a form with modifications of two or more amino acids selected from the group consisting of D965, Y981, H982, H983, A984, H985, D986, A987, Y988, Y1036, F1037, F1038, Y1039, T1102, S1106, E1108, S1116, D1117, D1125, D1127, D1135, S1136 and T1138 of the region 2-3 and the region 4-1 of the wild-type SpCas9.

For example, the SpCas9 variant may be a form with modifications of two or more amino acids selected from the group consisting of the non-polar amino acids, that is, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-3 of the wild-type SpCas9; and T1102, S1106, E1108, S1116, D1117, D1125, D1127, D1135, S1136 and T1138 of the region 4-1 of the wild-type SpCas9.

In one exemplary embodiment, the SpCas9 variant may be in a form in which two or more amino acids selected from the amino acid sequence of the second region and the fourth region of the wild-type SpCas9 are modified.

Here, the second region may be the region 2-1, the region 2-2 and the region 2-3.

Here, the fourth region may be the region 4-1.

For example, the SpCas9 variant may be a form with modifications of two or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038, Y1039, T1102, S1106, E1108, S1116, D1117, D1125, D1127, D1135, S1136 and T1138 of the second region and the fourth region of the wild-type SpCas9.

For example, the SpCas9 variant may be a form with modifications of two or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1038, Y1039, T1102, S1106, E1108, S1116, D1117, D1125, D1127, D1135, S1136 and T1138 of the second region and the fourth region of the wild-type SpCas9.

The Cas9 variant may be in a form in which two or more amino acids selected from the amino acid sequence of the third region and the fourth region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the third region and the fourth region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 3-1 and the region 4-1 of the wild-type SpCas9 are modified.

For example, the SpCas9 variant may be a form with modifications of two or more amino acids selected from the group consisting of V838, D839, H840, D853, N854, K855, K862, N863, R864, A889, K890, L891, T1102, S1106, E1108, S1116, D1117, D1125, D1127, D1135, S1136 and T1138 in the region 3-1 and the region 4-1 of the wild-type SpCas9.

For example, the SpCas9 variant may be a form with modifications of two or more amino acids selected from the group consisting of the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1 of the wild-type SpCas9; and T1102, S1106, E1108, S1116, D1117, D1125, D1127, D1135, S1136 and T1138 of the region 4-1 of the wild-type SpCas9.

The Cas9 variant may be in a form in which three or more amino acids selected from the amino acid sequence(s) of the first region, the second region, the third region and/or the fourth region of the wild-type Cas9 are modified. Here, the three or more amino acids may be present in different regions, respectively.

In one example, when the wild-type Cas9 is a wild-type SpCas9, a SpCas9 variant may be in a form in which three or more amino acids selected from the amino acid sequence(s) of the first region, the second region, the third region and/or the fourth region of the wild-type Cas9 are modified. Here, the three or more amino acids may be present in different regions, respectively.

In one exemplary embodiment, the SpCas9 variant may be in a form in which three or more amino acids selected from the amino acid sequence(s) of the first region, the second region and the third region of the wild-type SpCas9 are modified.

Here, the first region may be the region 1-1, the region 1-2, the region 1-3 and the region 1-4.

Here, the second region may be the region 2-1, the region 2-2 and the region 2-3.

Here, the third region may be the region 3-1.

For example, the SpCas9 variant may be a form with modifications of three or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038 and Y1039 of the first region, the second region and third region of the wild-type SpCas9.

For example, the SpCas9 variant may be a form with modifications of three or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the first region, the second region and the third region of the wild-type SpCas9.

In another exemplary embodiment, the SpCas9 variant may be in a form in which three or more amino acids selected from the amino acid sequence(s) of the first region, the second region and the fourth region of the wild-type SpCas9 are modified.

Here, the first region may be the region 1-1, the region 1-2, the region 1-3 and the region 1-4.

Here, the second region may be the region 2-1, the region 2-2 and the region 2-3.

Here, the fourth region may be the region 4-1.

For example, the SpCas9 variant may be a form with modifications of three or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, D965, Y981, H982, H983, A984, H985, D986, A987, Y988, Y1036, F1037, F1038, Y1039, T1102 and D1127 of the first region, the second region and the fourth region of the wild-type SpCas9.

For example, the SpCas9 variant may be a form with modifications of three or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the first region, the second region and the fourth region of the wild-type SpCas9.

In still another exemplary embodiment, the SpCas9 variant may be in a form in which three or more amino acids selected from the amino acid sequence(s) of the first region, the third region and the fourth region of the wild-type SpCas9 are modified.

Here, the first region may be the region 1-1, the region 1-2, the region 1-3 and the region 1-4.

Here, the third region may be the region 3-1.

Here, the fourth region may be the region 4-1.

For example, the SpCas9 variant may be a form with modifications of three or more amino acids selected from the group consisting of A203, N277, G366, K510, Y515, F539, G582, V583, E584, D585, N588, I601, N692, M694, Q695, H698, V838, D839, H840, D853, N854, K855, K862, N863, R864, A889, K890, L891, T1102 and D1127 of the first region, the third region and the fourth region of the wild-type SpCas9.

For example, the SpCas9 variant may be a form with modifications of three or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, T1102, S1106, E1108, S1116, D1117, D1125, D1127, D1135, S1136 and T1138 of the first region, the third region and the fourth region of the wild-type SpCas9.

In another exemplary embodiment, the SpCas9 variant may be in a form in which three or more amino acids selected from the amino acid sequence(s) of the second region, the third region and the fourth region of the wild-type SpCas9 are modified.

Here, the second region may be the region 2-1, the region 2-2 and the region 2-3.

Here, the third region may be the region 3-1.

Here, the fourth region may be the region 4-1.

For example, the SpCas9 variant may be a form with modifications of three or more amino acids selected from the group consisting of I7, G8, L9, D10, I11, G12, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the second region, the third region and the fourth region of the wild-type SpCas9.

For example, the SpCas9 variant may be a form with modifications of three or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the second region, the third region and the fourth region of the wild-type SpCas9.

The Cas9 variant may be in a form in which four or more amino acids selected from the amino acid sequences of the first region, the second region, the third region and the fourth region of the wild-type Cas9 are modified. Here, the four or more amino acids may be present in different regions, respectively.

In one example, when the wild-type Cas9 is a wild-type SpCas9, a SpCas9 variant may be in a form in which four or more amino acids selected from the amino acid sequences of the first region, the second region, the third region and the fourth region of the wild-type SpCas9 are modified. Here, the four or more amino acids may be present in different regions, respectively.

In one exemplary embodiment, the SpCas9 variant may be in a form in which three or more amino acids selected from the amino acid sequences of the first region, the second region, the third region and the fourth region of the wild-type SpCas9 are modified.

Here, the first region may be the region 1-1, the region 1-2, the region 1-3 and the region 1-4.

Here, the second region may be the region 2-1, the region 2-2 and the region 2-3.

Here, the third region may be the region 3-1.

Here, the fourth region may be the region 4-1.

For example, the SpCas9 variant may be a form with modifications of three or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the first region, the second region, the third region and the fourth region of the wild-type SpCas9.

For example, the SpCas9 variant may be a form with modifications of three or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the first region, the second region, the third region and the fourth region of the wild-type SpCas9.

The Cas9 variant may include a modification of at least one amino acid selected from the one or more regions.

Here, the modification may be a deletion of the selected one or more amino acids.

In one example, when the wild-type Cas9 is a wild-type SpCas9, the modification may be a deletion of one or more amino acids selected from the amino acid sequence of the first region of the wild-type SpCas9.

In one exemplary embodiment, the modification may be a deletion of one or more amino acids selected from the amino acid sequence(s) of the region 1-1, the region 1-2, the region 1-3 and/or the region 1-4 of the wild-type SpCas9.

For example, the modification may be a deletion of one or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9.

The modification may be a deletion of one or more amino acids selected from the amino acid sequence of the second region of the wild-type SpCas9.

In one exemplary embodiment, the modification may be a deletion of one or more amino acids selected from the amino acid sequence(s) in the region 2-1, the region 2-2 and/or the region 2-3 of the wild-type SpCas9.

For example, the modification may be a deletion of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9.

The modification may be a deletion of one or more amino acids selected from the amino acid sequence of the third region of the wild-type SpCas9.

In one exemplary embodiment, the modification may be a deletion of one or more amino acids selected from the amino acid sequence of the region 3-1 of the wild-type SpCas9.

For example, the modification may be a deletion of one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the wild-type SpCas9.

The modification may be a deletion of one or more amino acids selected from the amino acid sequence of the fourth region of the wild-type SpCas9.

In one exemplary embodiment, the modification may be a deletion of one or more amino acids selected from the amino acid sequence of the region 4-1 of the wild-type SpCas9.

For example, the modification may be a deletion of one or more amino acids selected from the group consisting of T1102, S1106, E1108, S1116, D1117, D1125, D1127, D1135, S1136 and T1138 of the region 4-1 of the wild-type SpCas9.

The modification may be a deletion of two or more amino acids selected from the amino acid sequence(s) of the first region, the second region, the third region and/or the fourth region of the wild-type SpCas9.

In one exemplary embodiment, the modification may be a deletion of two or more amino acids selected from the amino acid sequence in the region 1-1, the region 1-2, the region 1-3, the region 1-4, the region 2-1, the region 2-2, the region 2-3, the region 3-1 and/or the region 4-1 of the wild-type SpCas9.

For example, the modification may be a deletion of two or more amino acids selected from the group consisting of I7, G8, L9, D10, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9.

Here, the modification may be a substitution of the selected one or more amino acids with different amino acid(s).

In one example, when the wild-type Cas9 is a wild-type SpCas9, the modification may be a substitution of one or more amino acids selected from the amino acid sequence of the first region of the wild-type SpCas9 with different amino acid(s).

In one exemplary embodiment, the modification may be a substitution of one or more amino acids selected from the amino acid sequence(s) of the region 1-1, the region 1-2, the region 1-3 and/or the region 1-4 of the wild-type SpCas9 with stereoisomer(s).

For example, the modification may be a substitution of one or more amino acids selected from the group consisting of A203, N277, G366, K510, Y515, F539, G582, V583, E584, D585, N588, I601, N692, M694, Q695 and H698 of the wild-type SpCas9 with stereoisomer(s). For example, when lysine at $510^{th}$ position (K510) of the wild-type SpCas9 is L-lysine, the modification may be to substitute the lysine at $510^{th}$ position (K510) of the wild-type SpCas9 with D-lysine.

In one exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having a relatively low hydropathy index.

For example, the modification may be a substitution of one or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with amino acid(s) having a relatively low hydropathy index. For example, the modification may be to substitute phenylalanine at $539^{th}$ position (F539, hydropathy index: 2.8) of the wild-type SpCas9 with serine (hydropathy index: −0.8) having a relatively low hydropathy index. Alternatively, the modification may be to substitute isoleucine at $601^{th}$ position (I601, hydropathy index: 4.5) of the wild-type SpCas9 with asparagine (hydropathy index: −3.5) having a relatively low hydropathy index.

In another exemplary embodiment, the modification may be a substitution of one or more amino acids selected from the amino acid sequence of the region 1-1, the region 1-2, the region 1-3 and/or the region 1-4 of the wild-type SpCas9 with amino acid(s) having a relatively high hydropathy index.

For example, the modification may be a substitution of one or more amino acids selected from the group consisting of A203, N277, G366, K510, Y515, F539, G582, V583, E584, D585, N588, I601, N692, M694, Q695 and H698 of the wild-type SpCas9 with an amino acid having a relatively high hydropathy index. For example, the modification may be to substitute asparagine at $277^{th}$ position (N277, hydropathy index: −3.5) of the wild-type SpCas9 with histidine (hydropathy index: −3.2) having a relatively high hydropathy index.

In still another exemplary embodiment, the modification may be a substitution of one or more amino acids selected from the amino acid sequence of the region 1-1, the region 1-2, the region 1-3 and/or the region 1-4 of the wild-type SpCas9 with amino acid(s) having a relatively high or low hydropathy index.

In one exemplary embodiment, the modification may be a substitution of one or more amino acids selected from the amino acid sequence of the region 1-1, the region 1-2, the region 1-3 and/or the region 1-4 of the wild-type SpCas9 with amino acid(s) having a relatively small functional group.

For example, the modification may be a substitution of one or more amino acids selected from the group consisting of A203, N277, G366, K510, Y515, F539, G582, V583, E584, D585, N588, I601, N692, M694, Q695 and H698 of the wild-type SpCas9 with an amino acid having a relatively small functional group. For example, the modification may be to substitute phenylalanine at $539^{th}$ position (F539) of the wild-type SpCas9 with serine having a relatively small functional group.

In another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having a relatively large functional group.

For example, the modification may be a substitution of one or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with an amino acid having a relatively large functional group. For example, the modification may be to substitute alanine at $203^{th}$ position (A203) of the wild-type SpCas9 with aspartic acid having a relatively large functional group. For example, the modification may be to substitute glycine at $366^{th}$ position (G366) of the wild-type SpCas9 with serine having a relatively large functional group.

In still another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having a relatively large or small functional group.

In one exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having relatively low hydrophobicity.

For example, the modification may be a substitution of one or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with an amino acid having relatively low hydrophobicity. For example, the modification may be to substitute phenylalanine at $539^{th}$ position (F539, Kyte-Doolittle hydrophobicity: 2.8) and isoleucine at $601^{th}$ position (I601, Kyte-Doolittle hydrophobicity: 4.5) of the wild-type SpCas9 with serine (Kyte-Doolittle hydrophobicity: −0.8) and asparagine (Kyte-Doolittle hydrophobicity: −3.5), which have relatively further low hydrophobicity, respectively.

In another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having relatively high hydrophobicity.

For example, the modification may be a substitution of one or more amino acids selected from the group consisting of N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with an amino acid having relatively high hydrophobicity. For example, the modification may be to substitute asparagine at 277$^{th}$ position (N277, Kyte-Doolittle hydrophobicity: −3.5) and phenylalanine at 682$^{th}$ position (F682, Kyte-Doolittle hydrophobicity: 2.8) of the wild-type SpCas9 with histidine (Kyte-Doolittle hydrophobicity: −3.2) and valine (Kyte-Doolittle hydrophobicity: 4.2), which have relatively high hydrophobicity, respectively.

In still another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having relatively low or high hydrophobicity.

The modification may be a substitution of one or more amino acids selected from the amino acid sequence(s) of the second region of the wild-type SpCas9 with different amino acid(s).

In one exemplary embodiment, the modification may be a substitution of one or more amino acids selected from the amino acid sequence(s) of the region 2-1, the region 2-2 and/or the region 2-3 of the wild-type SpCas9 with stereoisomer(s).

For example, the modification may be a substitution of one or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the wild-type SpCas9 with stereoisomer(s). For example, when glycine at 12$^{th}$ position (G12) of the wild-type SpCas9 is L-glycine, the modification may be to substitute glycine at 12$^{th}$ position (G12) of the wild-type SpCas9 with D-glycine.

In one exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively low hydropathy index.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having a relatively low hydropathy index. For example, the modification may be to substitute phenylalanine at 1038$^{th}$ position (F1038, hydropathy index: 2.8) of the wild-type SpCas9 with tyrosine (hydropathy index: −1.3) having a relatively low hydropathy index.

In another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively high hydropathy index.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having a relatively high hydropathy index. For example, the modification may be to substitute methionine at 763$^{th}$ position (M763, hydropathy index: 1.9) of the wild-type SpCas9 with isoleucine (hydropathy index: 4.5) having a relatively high hydropathy index. For example, the modification may be to substitute aspartic acid at 965$^{th}$ position (D965, hydropathy index: −3.5) of the wild-type SpCas9 with tyrosine (hydropathy index: −1.3) having a relatively high hydropathy index.

In still another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively high or low hydropathy index.

In one exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively small functional group.

For example, the modification may be a substitution of one or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the wild-type SpCas9 with an amino acid having a relatively small functional group. For example, the modification may be to substitute methionine at 763$^{th}$ position (M763) of the wild-type SpCas9 with isoleucine having a relatively small functional group.

In another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively large functional group.

For example, the modification may be a substitution of one or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the wild-type SpCas9 with an amino acid having a relatively large functional group. For example, the modification may be to substitute phenylalanine at 1038$^{th}$ position (F1038) of the wild-type SpCas9 with tyrosine having a relatively large functional group.

In still another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively large or small functional group.

In one exemplary embodiment, the modification may be a substitution of one or more amino acids selected from the amino acid sequence(s) of the region 2-1, the region 2-2 and/or the region 2-3 of the wild-type SpCas9 with amino acid(s) having relatively low hydrophobicity.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having relatively low hydrophobicity. For example, the modification may be to substitute isoleucine at $761^{th}$ position (I761, Kyte-Doolittle hydrophobicity: 4.5) and phenylalanine at $1038^{th}$ position (F1038, Kyte-Doolittle hydrophobicity: 2.8) of the wild-type SpCas9 with methionine (Kyte-Doolittle hydrophobicity: 1.9) and tyrosine (Kyte-Doolittle hydrophobicity: −1.3), which have relatively low hydrophobicity, respectively.

In another exemplary embodiment, the modification may be a substitution of one or more amino acids selected from the amino acid sequence(s) of the region 2-1, the region 2-2 and/or the region 2-3 of the wild-type SpCas9 with amino acid(s) having relatively high hydrophobicity.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having relatively high hydrophobicity. For example, the modification may be to substitute methionine at $763^{th}$ position (M763, Kyte-Doolittle hydrophobicity: 1.9) and alanine at $932^{th}$ position (A932, Kyte-Doolittle hydrophobicity: 1.8) of the wild-type SpCas9 with isoleucine (Kyte-Doolittle hydrophobicity: 4.5) and cysteine (Kyte-Doolittle hydrophobicity: 2.5), which have relatively high hydrophobicity, respectively.

In still another exemplary embodiment, the modification may be a substitution of one or more amino acids selected from the amino acid sequence(s) of the region 2-1, the region 2-2 and/or the region 2-3 of the wild-type SpCas9 with amino acid(s) having relatively low or high hydrophobicity.

The modification may be a substitution of one or more amino acids selected from the amino acid sequence of the third region of the wild-type SpCas9 with a different amino acid.

In one exemplary embodiment, the modification may be a substitution of one or more amino acids selected from the amino acid sequence of the region 3-1 of the wild-type SpCas9 with stereoisomer(s).

For example, the modification may be a substitution of one or more amino acids selected from the group consisting of V838, D839, H840, D853, N854, K855, K862, N863, R864, A889, K890 and L891 of the wild-type SpCas9 with a stereoisomer. For example, when aspartic acid at $853^{th}$ position (D853) of the wild-type SpCas9 is L-aspartic acid, the modification may be to substitute aspartic acid at $853^{th}$ position (D853) of the wild-type SpCas9 with D-aspartic acid.

In one exemplary embodiment, the modification may be a substitution of one or more amino acids selected from the amino acid sequence of the region 3-1 of the wild-type SpCas9 with an amino acid having a relatively low hydropathy index.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively low hydropathy index. For example, the modification may be to substitute lysine at $862^{th}$ position (K862, hydropathy index: −3.9) of the wild-type SpCas9 with arginine (hydropathy index: −4.5) having a relatively low hydropathy index.

In another exemplary embodiment, the modification may be a substitution of one or more amino acids selected from the amino acid sequence of the region 3-1 of the wild-type SpCas9 with an amino acid having a relatively high hydropathy index.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively high hydropathy index. For example, the modification may be to substitute lysine at $890^{th}$ position (K890, hydropathy index: −3.9) of the wild-type SpCas9 with asparagine (hydropathy index: −3.5) having a relatively high hydropathy index.

In still another exemplary embodiment, the modification may be a substitution of one or more amino acids selected from the amino acid sequence of the region 3-1 of the wild-type SpCas9 with amino acid(s) having a relatively high or low hydropathy index.

In one exemplary embodiment, the modification may be a substitution of one or more amino acids selected from the amino acid sequence of the region 3-1 of the wild-type SpCas9 with amino acid(s) having a relatively small functional group.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively small functional group. For example, the modification may be to substitute lysine at $890^{th}$ position (K890) of the wild-type SpCas9 with asparagine having a relatively small functional group.

In another exemplary embodiment, the modification may be a substitution of one or more amino acids selected from the amino acid sequence of the region 3-1 of the wild-type SpCas9 with amino acid(s) having a relatively large functional group.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively large functional group. For example, the modification may be to substitute asparagine at $863^{th}$ position (N863) of the wild-type SpCas9 with arginine having a relatively large functional group.

In still another exemplary embodiment, the modification may be a substitution of one or more amino acids selected from the amino acid sequence of the region 3-1 of the wild-type SpCas9 with amino acid(s) having a relatively large or small functional group.

In one exemplary embodiment, the modification may be a substitution of one or more amino acids selected from the amino acid sequence of the region 3-1 of the wild-type SpCas9 with amino acid(s) having relatively low hydrophobicity.

For example, the modification may be a substitution of one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the wild-type SpCas9 with an amino acid having relatively low hydrophobicity. For example, the modification may be to substitute glutamic acid at $779^{th}$ position (E779, Kyte-Doolittle hydrophobicity: −3.5) and lysine at $862^{th}$ position (K862, Kyte-Doolittle hydrophobicity: −3.9) of the wild-type SpCas9 with lysine (Kyte-Doolittle hydrophobicity: −3.9) and arginine (Kyte-Doolittle hydrophobicity: −4.5), which have relatively low hydrophobicity, respectively.

In another exemplary embodiment, the modification may be a substitution of one or more amino acids selected from the amino acid sequence of the region 3-1 of the wild-type SpCas9 with amino acid(s) having relatively high hydrophobicity.

For example, the modification may be a substitution of one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the wild-type SpCas9 with an amino acid having relatively high hydrophobicity. For example, the modification may be to substitute glutamic acid at $827^{th}$ position (E827, Kyte-Doolittle hydrophobicity: −3.5) and lysine at $890^{th}$ position (K890, Kyte-Doolittle hydrophobicity: −3.9) of the wild-type SpCas9 with methionine (Kyte-Doolittle hydrophobicity: 1.9) and asparagine (Kyte-Doolittle hydrophobicity: −3.5), which have relatively high hydrophobicity, respectively.

In still another exemplary embodiment, the modification may be a substitution of one or more amino acids selected from the amino acid sequence of the region 3-1 of the wild-type SpCas9 with amino acid(s) having relatively low or high hydrophobicity.

The modification may be a substitution of one or more amino acids selected from the amino acid sequence of the fourth region of the wild-type SpCas9 with a different amino acid.

In one exemplary embodiment, the modification may be a substitution of one or more amino acids selected from the amino acid sequence of the region 4-1 of the wild-type SpCas9 with stereoisomer(s).

For example, the modification may be a substitution of one or more amino acids selected from the group consisting of T1102, S1106, E1108, S1116, D1117, D1125, D1127, D1135, S1136 and T1138 of the wild-type SpCas9 with a stereoisomer. For example, when aspartic acid at $1127^{th}$ position (D1127) of the wild-type SpCas9 is L-aspartic acid, the modification may be to substitute aspartic acid at $1127^{th}$ position (D1127) of the wild-type SpCas9 with D-aspartic acid.

In one exemplary embodiment, the modification may be a substitution of one or more amino acids selected from the amino acid sequence of the region 4-1 of the wild-type SpCas9 with amino acid(s) having a relatively low hydropathy index.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively low hydropathy index. For example, the modification may be to substitute threonine at $1102^{th}$ position (T1102, hydropathy index: −0.7) of the wild-type SpCas9 with proline (hydropathy index: −1.6) having a relatively low hydropathy index.

In another exemplary embodiment, the modification may be a substitution of one or more amino acids selected from the amino acid sequence of the region 4-1 of the wild-type SpCas9 with amino acid(s) having a relatively high hydropathy index.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively high hydropathy index. For example, the modification may be to substitute serine at $1106^{th}$ position (S1106, hydropathy index: −0.8) of the wild-type SpCas9 with glycine (hydropathy index: −0.4) having a relatively high hydropathy index.

In still another exemplary embodiment, the modification may be a substitution of one or more amino acids selected from the amino acid sequence of the region 4-1 of the wild-type SpCas9 with amino acid(s) having a relatively high or low hydropathy index.

In one exemplary embodiment, the modification may be a substitution of one or more amino acids selected from the amino acid sequence of the region 4-1 of the wild-type SpCas9 with amino acid(s) having a relatively small functional group.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively small functional group. For example, the modification may be to substitute threonine at $1102^{th}$ position (T1102) of the wild-type SpCas9 with proline having a relatively small functional group.

In another exemplary embodiment, the modification may be a substitution of one or more amino acids selected from the amino acid sequence of the region 4-1 of the wild-type SpCas9 with amino acid(s) having a relatively large functional group.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively large functional group. For example, the modification may be to substitute aspartic acid at $1127^{th}$ position (D1127) of the wild-type SpCas9 with glutamic acid having a relatively large functional group.

In still another exemplary embodiment, the modification may be a substitution of one or more amino acids selected from the amino acid sequence of the region 4-1 of the wild-type SpCas9 with amino acid(s) having a relatively large or small functional group.

In one exemplary embodiment, the modification may be a substitution of one or more amino acids selected from the amino acid sequence of the region 4-1 of the wild-type SpCas9 with amino acid(s) having relatively low hydrophobicity.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively low hydrophobicity. For example, the modification may be to substitute threonine at $1102^{th}$ position (T1102, Kyte-Doolittle hydrophobicity: −0.7) of the wild-type SpCas9 with proline (Kyte-Doolittle hydrophobicity: −1.6) having relatively low hydrophobicity.

In another exemplary embodiment, the modification may be a substitution of one or more amino acids selected from the amino acid sequence of the region 4-1 of the wild-type SpCas9 with amino acid(s) having relatively high hydrophobicity.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having relatively high hydrophobicity. For example, the modification may be to substitute glutamic acid at $1108^{th}$ position (E1108, Kyte-Doolittle hydrophobicity: −3.5) of the wild-type SpCas9 with methionine (Kyte-Doolittle hydrophobicity: 1.9) having a relatively high hydrophobicity.

In still another exemplary embodiment, the modification may be a substitution of one or more amino acids selected from the amino acid sequence of the region 4-1 of the wild-type SpCas9 with amino acid(s) having relatively low or high hydrophobicity.

The modification may be a substitution of two or more amino acids selected from the amino acid sequence in the first region, the second region, the third region and/or the fourth region of the wild-type SpCas9 with different amino acids.

In one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with stereoisomers, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with stereoisomers, respectively. For example, when glycine at $8^{th}$ position (G8) of the wild-type SpCas9 is L-glycine, and asparagine at $767^{th}$ position (N767) is L-asparagine, the modification may be to substitute glycine at $8^{th}$ position (G8) and asparagine at $767^{th}$ position (N767) of the wild-type SpCas9 with D-glycine and D-asparagine, respectively.

In one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively small hydropathy index, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively small hydropathy index, respectively. For example, the modification may be to substitute alanine at $203^{th}$ position (A203, hydropathy index: 1.8) and phenyl-alanine at $539^{th}$ position (F539, hydropathy index: 2.8) of the wild-type SpCas9 with aspartic acid (hydropathy index:

−3.5) and serine (hydropathy index: −0.8), which have a relatively low hydropathy index, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively small hydropathy index, respectively. For example, the modification may be to sub-stitute isoleucine at $601^{th}$ position (I601, hydropathy index: 4.5) and threonine at $1102^{th}$ position (T1102, hydropathy index: −0.7) of the wild-type SpCas9 with asparagine (hy-dropathy index: −3.5) and proline (hydropathy index: −1.6), which have a relatively low hydropathy index, respectively.

In another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively high hydropathy index, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively high hydropathy index, respectively. For example, the modification may be to substitute asparagine at $277^{th}$ position (N277, hydropathy index: −3.5) and histidine at $840^{th}$ position (H840, hydropathy index: −3.2) of the wild-type SpCas9 with histidine (hydropathy index: −3.2) and alanine (hydropathy index: 1.8), which have a relatively high hydropathy index, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively high hydropathy index, respectively. For example, the modification may be to substitute methionine at $763^{th}$ position (M763, hydropathy index: 1.9) and lysine at $890^{th}$ position (K890, hydropathy index: −3.9) of the wild-type SpCas9 with isoleucine (hydropathy index: 4.5) and asparagine (hydropathy index: −3.5), which have a relatively high hydropathy index, respectively.

In still another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively high or low hydropathy index, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively high or low hydropathy index, respectively. For example, the modification may be to substitute aspartic acid at $10^{th}$ position (D10, hydropathy index: −3.5) and histidine at $840^{th}$ position (H840, hydropathy index: −3.2) of the wild-type SpCas9 with alanine (hydropathy index: 1.8) having a relatively high hydropathy index, respectively, and to substitute phenylalanine at $539^{th}$ position (F539, hydropathy index: 2.8) of the wild-type SpCas9 with serine (hydropathy index: −0.8) having a relatively small hydropathy index.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively high or low hydropathy index, respectively. For example, the modification may be to substitute methionine at $763^{th}$ position (M763, hydropathy index: 1.9) and lysine at $890^{th}$ position (K890, hydropathy index: −3.9) of the wild-type SpCas9 with isoleucine (hydropathy index: 4.5) and asparagine (hydropathy index: −3.5), which have a relatively high hydropathy index, respectively, and to substitute phenylalanine at $539^{th}$ position (F539, hydropathy index: 2.8) of the wild-type SpCas9 with serine (hydropathy index: −0.8) having a relatively low hydropathy index.

In one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively small functional group, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively small functional group, respectively. For example, the modification may be to substitute phenylalanine at $539^{th}$ position (F539), methionine at $763^{th}$ position (M763) and threonine at $1102^{th}$ position (T1102) of wild-type SpCas9 with serine, isoleucine and proline, which have a relatively small functional group, respectively.

In another one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively large functional group, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively large functional group, respectively. For example, the modification may be to substitute isoleucine at 601$^{th}$ position (I601), phenylalanine at 1038$^{th}$ position (F1038) and aspartic acid at 1127$^{th}$ position (D1127) of the wild-type SpCas9 with asparagine, tyrosine and glutamic acid, which have a relatively large functional group, respectively.

In still another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively large or small functional group, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively large or small functional group. For example, the modification may be to substitute phenylalanine at 539$^{th}$ position (F539), methionine at 763th position (M763) and lysine at 890$^{th}$ position (K890) of the wild-type SpCas9 with serine, isoleucine and asparagine having a relatively small functional group, respectively, and to substitute isoleucine at 601$^{th}$ position (I601) and phenylalanine at 1038$^{th}$ position (F1038) with asparagine and tyrosine, which have a relatively large functional group.

In one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having relatively low hydrophobicity, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having relatively low hydrophobicity, respectively. For example, the modification may be to substitute phenylalanine at 539$^{th}$ position (F539, Kyte-Doolittle hydrophobicity: 2.8), isoleucine at 601$^{th}$ position (I601, Kyte-Doolittle hydrophobicity: 4.5) and threonine at 1102$^{th}$ position (T1102, Kyte-Doolittle hydrophobicity: −0.7) of the wild-type SpCas9 with serine (Kyte-Doolittle hydrophobicity: −0.8), asparagine (Kyte-Doolittle hydrophobicity: −3.5) and proline (Kyte-Doolittle hydrophobicity: −1.6), which have relatively low hydrophobicity, respectively.

In another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having relatively high hydrophobicity, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having relatively high hydrophobicity, respectively. For example, the modification may be to substitute aspartic acid at 10$^{th}$ position (D10, Kyte-Doolittle hydrophobicity: −3.5), methionine at 763$^{th}$ position (M763, Kyte-Doolittle hydrophobicity: 1.9), histidine at 840$^{th}$ position (H840, Kyte-Doolittle hydrophobicity: −3.2) and lysine at 890$^{th}$ position (K890, Kyte-Doolittle hydrophobicity: −3.9) of the wild-type SpCas9 with alanine (Kyte-Doolittle hydrophobicity: 1.8), isoleucine (Kyte-Doolittle hydrophobicity: 4.5), alanine (Kyte-Doolittle hydrophobicity: 1.8) and asparagine (Kyte-Doolittle hydrophobicity: −3.5), which have relatively high hydrophobicity, respectively.

In still another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having relatively low or high hydrophobicity, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, 226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having relatively low or high hydrophobicity, respectively. For example, the modification may be to substitute methionine at 763$^{th}$ position (M763, Kyte-Doolittle hydrophobicity: 1.9) and lysine at 890$^{th}$ position (K890, Kyte-Doolittle hydrophobicity: −3.9) of the wild-type SpCas9 with isoleucine (Kyte-Doolittle hydrophobicity: 4.5) and asparagine (Kyte-Doolittle hydrophobicity: −3.5), which have relatively high hydrophobicity, respectively, and to substitute phenylalanine at 539$^{th}$ position (F539, Kyte-Doolittle hydrophobicity: 2.8) of the wild-type SpCas9 with serine (Kyte-Doolittle hydrophobicity: −0.8) having relatively low hydrophobicity.

The modification may be a substitution of the selected one or more amino acids with the same number of other amino acids.

For example, the modification may be to substitute one isoleucine located in the first region of the wild-type SpCas9 with one asparagine. Alternatively, the modification may be to substitute one phenylalanine located in the first region of the wild-type SpCas9 and one lysine located in the third region with one serine (first region) and one asparagine (third region), respectively. Alternatively, the modification may be to substitute one methionine and one phenylalanine, which are located in the second region, and one lysine located in the third region of the wild-type SpCas9, with one isoleucine, one tyrosine (second region) and one asparagine (third region), respectively.

The modification may be a substitution of the selected one or more amino acids with a different number of other amino acids.

For example, the modification may be to substitute one threonine located in the second region of the wild-type SpCas9 with cysteine-alanine-alanine, that is, a total of three amino acids. Alternatively, the modification may be to substitute one glutamine located in the first region and two contiguous amino acids, glycine-serine, located in the third region of the wild-type SpCas9 with methionine-valine (first region) and proline (third region), respectively. Alternatively, the modification may be to substitute one serine located in the first region, three contiguous amino acids, lysine-lysine-tyrosine, located in the second region and two contiguous amino acids, serine-isoleucine, located in the third region of the wild-type SpCas9 with alanine (first region), methionine-proline (second region) and cysteine-alanine-threonine-valine (third region), respectively.

The artificially engineered Cas9 may be a Cas9 variant with an addition of at least one amino acid to one or more regions selected from the first region, the second region, the third region and the fourth region of the wild-type Cas9.

Here, the addition may be the addition of one or more amino acids to the N-terminal and/or C-terminal position(s) of one or more amino acids present in the selected one or more regions.

In one example, when the wild-type Cas9 is a wild-type SpCas9, the addition may be the addition of one or more amino acids to the N-terminal and/or C-terminal position(s) present in the first region, the second region, the third region and/or the fourth region of the wild-type SpCas9.

In one exemplary embodiment, the addition may be the addition of one or more positive charged amino acids to the N-terminal and/or C-terminal position(s) of one or more amino acids present in the first region, the second region, the third region and/or the fourth region of the wild-type SpCas9.

For example, the addition may be to add one arginine to the C-terminus of selected one alanine located in the region 1-1 of the wild-type SpCas9. Alternatively, the addition may be to add two amino acids, arginine-lysine, to the N-terminus of selected glutamic acid located in the region 2-2 of the wild-type SpCas9. Alternatively, the addition may be to add two amino acids, arginine-histidine, to the N-terminus of selected leucine located in the region 3-1 of the wild-type SpCas9. Alternatively, the addition may be to add two amino acids, lysine-histidine, to the C-terminus of selected leucine located in the region 3-1 of the wild-type SpCas9, and to add one lysine to the C-terminus of selected tyrosine located in the region 4-1 of the wild-type SpCas9.

In another exemplary embodiment, the addition may be the addition of one or more negatively-charged amino acids to N-terminal and/or C-terminal position(s) of the one or more amino acids present in the first region, the second region, the third region and/or the fourth region of the wild-type SpCas9.

For example, the addition may be to add one aspartic acid to the N-terminus of selected one glycine located in the region 1-2 of the wild-type SpCas9. Alternatively, the addition may be to add three amino acids, glutamic acid-aspartic acid-glutamic acid, to the C-terminus of selected methionine located in the region 2-3 of the wild-type SpCas9. Alternatively, the addition may be to add two amino acids, glutamic acid-glutamic acid, to the N-terminus of selected isoleucine located in the region 3-1 of the wild-type SpCas9. Alternatively, the addition may be to add two amino acids, glutamic acid-aspartic acid, to the C-terminus of selected phenylalanine located in the region 1-1 of the wild-type SpCas9, and to add one aspartic acid to the N-terminus of selected glutamine located in the region 2-1 of the wild-type SpCas9.

In still another exemplary embodiment, the addition may be the addition of one or more non-charged amino acids to the N-terminal and/or C-terminal position(s) present in the first region, the second region, the third region and/or the fourth region of the wild-type SpCas9.

For example, the addition may be to add two amino acids, serine-valine, to the C-terminus of selected one phenylalanine located in the region 1-1 of the wild-type SpCas9. Alternatively, the addition may be to add five amino acids, glycine-proline-glutamine-phenylalanine-leucine, to the N-terminus of selected histidine located in the region 2-1 of the wild-type SpCas9. Alternatively, the addition may be to add two amino acids, alanine-alanine, to the N-terminus of selected asparagine located in the region 3-1 of the wild-type SpCas9. Alternatively, the addition may be to add two amino acids, phenylalanine-leucine, to the C-terminus of selected aspartic acid located in the region 1-1 of the wild-type SpCas9, and to add one serine to the N-terminus of selected glutamine located in the region 1-2 of the wild-type SpCas9.

In another exemplary embodiment, the addition may be the addition of one or more amino acids selected from positively-charged amino acids, negatively-charged amino acids and non-charged amino acids to the N-terminal and/or C-terminal position(s) of one or more amino acids present in the first region, the second region, the third region and/or the fourth region of the wild-type SpCas9.

For example, the addition may be to add six amino acids, histidine-arginine-glycine-serine-alanine-glutamic acid, to the C-terminus of selected one arginine located in the region 1-2 of the wild-type SpCas9. Alternatively, the addition may be to add ten amino acids, lysine-lysine-alanine-phenylalanine-glutamine-threonine-methionine-cysteine-aspartic acid-serine, to the N-terminus of selected one glycine located in the region 3-1 of the wild-type SpCas9. Alternatively, the addition may be to add two amino acids, phenylalanine-histidine, to the C-terminus of selected methionine located in the region 2-1 of the wild-type SpCas9, and to add one lysine to the N-terminus of selected glutamine located in the region 2-3 of the wild-type SpCas9. Alternatively, the addition may be to add two amino acids, aspartic acid-serine, to the C-terminus of selected lysine located in the region 1-1 of the, to add six amino acids, glutamine-threonine-methionine-cysteine-aspartic acid-lysine, to the N-terminus of selected threonine located in the region 2-2 of the wild-type SpCas9, and to add two amino acids, arginine-glycine, to the C-terminus of selected glutamine located in the region 4-1 of the wild-type SpCas9.

Here, the addition may be the addition of one or more functional domains to the N-terminal and/or C-terminal position(s) of one or more amino acids present in the selected one or more regions.

The functional domain may be a domain having an additional function, in addition to the original functions of the wild-type Cas9, that is, a first function of cleaving a first strand of double-stranded DNA and a second function of cleaving a second strand of the double-stranded DNA.

Alternatively, the functional domain may be a domain having a function similar to the original functions of the wild-type Cas9, that is, a first function of cleaving a first strand of double-stranded DNA and/or a second function of cleaving a second strand of the double-stranded DNA.

Descriptions related to the functional domain are the same as described above.

In one example, when the wild-type Cas9 is a wild-type SpCas9, the addition may be the addition of one or more functional domain to the N-terminal and/or C-terminal position(s) of one or more amino acids present in the first region, the second region, the third region and/or the fourth region of the wild-type SpCas9.

In one exemplary embodiment of the disclosure disclosed herein, the artificially engineered Cas9 may be target-specific Cas9.

The "target-specific Cas9 (TS-Cas9)" refers to a Cas9 variant produced through artificial manipulation to relatively increase target specificity, compared to wild-type Cas9.

Here, the "target specificity" means that Cas9 forms a gRNA-Cas9 complex through the interaction with gRNA such that Cas9 specifically acts on a target sequence complementarily binding to gRNA when the gRNA-Cas9 complex approaches or is localized to a target gene or nucleic acid, that is, a subject (nucleic acid) to be manipulated using Cas9. Here, a target sequence completely complementary binding (100%) with gRNA is called an "on-target," and a target sequence having incomplete complementary binding (less than 100%), that is, one or more non-complementary bonds, with gRNA is called an "off-target."

The target specificity may vary according to the degree of complementary binding between gRNA and the target sequence.

In one example, in the case in which a target sequence complementarily binding to gRNA is an on-target, that is, complementary binding between gRNA and the target sequence are full complementary binding (100%), the target specificity is at the highest level.

In another example, in the case in which the target sequence complementarily binding to gRNA is an off-target, that is, complementary binding between gRNA and the target sequence are less than 100% and include one or more non-complementary bonds between them, the target specificity may be lower than that of the on-target, and the higher the number of the non-complementary bonds, the lower the target specificity.

For example, when complementary binding between gRNA and the target sequence is complete complementary binding (100%), the target specificity may be 100%, and when there is one non-complementary bond between gRNA and the target sequence, that is, complementary binding between gRNA and the target sequence is incomplete complementary binding (95%), the target specificity may be 95%. In addition, when there are four non-complementary bonds between gRNA and the target sequence, that is, complementary binding between gRNA and the target sequence is incomplete complementary binding (80%), the target specificity may be 80%.

In still another example, when the target sequence complementarily binding to gRNA is an off-target, that is, the degree of complementary binding between gRNA and the target sequence is less than 100%, that is, there are one or more non-complementary bonds, the target specificity may vary according to the location of the non-complementary bond.

For example, when there is one non-complementary bond between gRNA and the target sequence, and the non-complementary bond becomes closer to PAM adjacent to the target sequence, the target specificity may be lower than that when the non-complementary bond is spaced far from PAM.

The target specificity may vary according to the degree of interaction of gRNA which complementary binds with the target sequence, and Cas9.

In one example, when the interaction of gRNA which complementary binds with the target sequence, and Cas9 may be reduced, the smaller the number of non-complementary bonds between gRNA and the target sequence, the higher target specificity.

For example, when the interaction of gRNA which complementarily bind to the target sequence, and Cas9 is reduced, the target specificity when there is one non-complementary bond between gRNA and the target sequence may be higher than that when there are three non-complementary bonds between gRNA and the target sequence.

In another example, when the interaction of gRNA which complementarily bind to the target sequence, and Cas9 is reduced, the Cas9 may have target specificity only when the complementary binding between gRNA and the target sequence is complete complementary binding (100%).

For example, in the case in which the interaction of gRNA complementarily binding to the target sequence and Cas9 is reduced, only when the target sequence is an on-target, the Cas9 may have target specificity.

The target specificity may vary according to the degree of interaction between the target sequence complementarily binding to gRNA and Cas9.

In one example, when the interaction between a target sequence complementarily binding to gRNA and Cas9 is reduced, the lower the number of non-complementary bonds between gRNA and the target sequence, the higher the target specificity.

For example, when the interaction between a target sequence complementarily binding to gRNA and Cas9 is reduced, compared to the case in which there are four non-complementary bonds between gRNA and the target sequence, in the case in which there are two non-complementary bonds therebetween, target specificity may relatively increase.

In another example, when the interaction between a target sequence complementarily binding to gRNA and Cas9 is reduced, only in the case in which complementary binding between gRNA and the target sequence is complete complementary binding (100%), the Cas9 may have target specificity.

For example, when the interaction between a target sequence complementarily binding to gRNA and Cas9 is reduced, only when the target sequence is an on-target, the Cas9 may have target specificity.

The target-specific Cas9 may be a Cas9 variant manipulating an on-target.

Here, the manipulation may be to cleave the nucleotide sequence of the on-target using the Cas9 variant, or to modify the nucleotide sequence of an on-target such that one or more nucleotides may be deleted from and/or inserted into the nucleotide sequence of the on-target.

The target-specific Cas9 may be a Cas9 variant which has a target specificity for the on-target, which is the same as or higher than that of the wild-type Cas9.

The target-specific Cas9 may be a Cas9 variant that does not manipulate an off-target.

Here, the manipulation may be to cleave the nucleotide sequence of the off-target using the Cas9 variant, or to modify the nucleotide sequence of the off-target such that one or more nucleotides may be deleted from and/or inserted into the nucleotide sequence of the off-target.

The target-specific Cas9 may be a Cas9 variant which is decreased in target specificity for the on-target, compared to the wild-type Cas9.

The target-specific Cas9 may be a Cas9 variant which has the same target specificity for the on-target and lower target specificity for the off-target, compared to the wild-type Cas9.

The target-specific Cas9 may be a Cas9 variant which has the same target specificity for the off-target and higher target specificity for the on-target, compared to the wild-type Cas9.

The target-specific Cas9 may be a Cas9 variant which has higher target specificity for the on-target and lower target specificity for the off-target, compared to the wild-type Cas9.

The target-specific Cas9 may be a Cas9 variant which has lower target specificity for the on-target and lower target specificity for the off-target, compared to the wild-type Cas9.

In one exemplary embodiment of the disclosure disclosed herein, the target-specific Cas9 may be a target-specific SpCas9.

The "target-specific SpCas9 (TS-SpCas9)" refers to a SpCas9 variant produced by artificial manipulation to relatively increase target specificity, compared to the wild-type SpCas9.

The TS-SpCas9 may be a SpCas9 variant manipulating the on-target.

Here, the manipulation may be to cleave the nucleotide sequence of the on-target using the SpCas9 variant, or to modify the nucleotide sequence of the on-target such that one or more nucleotides may be deleted from and/or inserted into the nucleotide sequence of the on-target.

The TS-SpCas9 may be a SpCas9 variant which has the same or higher target specificity for the on-target, compared to the wild-type SpCas9.

The TS-SpCas9 may be a SpCas9 variant that does not manipulate the off-target.

Here, the manipulation may be to cleave the nucleotide sequence of the off-target using the SpCas9 variant, or to modify the nucleotide sequence of the off-target such that one or more nucleotides may be deleted from and/or inserted into the nucleotide sequence of the off-target.

The TS-SpCas9 may be a SpCas9 variant having reduced target specificity for the off-target, compared to the wild-type SpCas9.

The TS-SpCas9 may be a SpCas9 variant which has the same target specificity for the on-target and lower target specificity for the off-target, compared to the wild-type SpCas9.

The TS-SpCas9 may be a SpCas9 variant which has the same target specificity for the off-target and higher target specificity for the on-target, compared to the wild-type SpCas9.

The TS-SpCas9 may be a SpCas9 variant which has higher target specificity for the on-target and lower target specificity for the off-target, compared to the wild-type SpCas9.

The TS-SpCas9 may be a SpCas9 variant which has lower target specificity for the on-target and lower target specificity for the off-target, compared to the wild-type SpCas9.

The TS-SpCas9 may be a SpCas9 variant in which at least one amino acid in the amino acid sequence of one or more regions selected from the first region, the second region, the third region and the fourth region of the wild-type SpCas9 is modified.

The first region may be the amino acid sequence (region 1-1) from phenylalanine at $196^{th}$ position (F196) to isoleucine at $282^{th}$ position (I282) of the wild-type SpCas9.

The first region may be the amino acid sequence (region 1-2) from proline at $316^{th}$ position (P316) to asparagine at $394^{th}$ position (N394) of the wild-type SpCas9.

The first region may be the amino acid sequence (region 1-3) from lysine at $510^{th}$ position (K510) to asparagine at $612^{th}$ position (N612) of the wild-type SpCas9.

The first region may be the amino acid sequence (region 1-4) from threonine at $678^{th}$ position (T678) to histidine at $698^{th}$ position (H698) of the wild-type SpCas9.

The first region may be two regions selected from the amino acid sequence (region 1-1) from phenylalanine at $196^{th}$ position (F196) to isoleucine at $282^{th}$ position (I282), the amino acid sequence (region 1-2) from proline at $316^{th}$ position (P316) to asparagine at $394^{th}$ position (N394), the amino acid sequence (region 1-3) from lysine at $510^{th}$ position (K510) to asparagine at $612^{th}$ position (N612), and the amino acid sequence (region 1-4) from threonine at $678^{th}$ position (T678) to histidine at $698^{th}$ position (H698) of the wild-type SpCas9.

The first region may be three regions selected from the amino acid sequence (region 1-1) from phenylalanine at $196^{th}$ position (F196) to isoleucine at $282^{th}$ position (I282), the amino acid sequence (region 1-2) from proline at $316^{th}$ position (P316) to asparagine at $394^{th}$ position (N394), the amino acid sequence (region 1-3) from lysine at $510^{th}$ position (K510) to asparagine at $612^{th}$ position (N612), and the amino acid sequence (region 1-4) from threonine at $678^{th}$ position (T678) to histidine at $698^{th}$ position (H698) of the wild-type SpCas9.

The first region may be the amino acid sequence (region 1-1) from phenylalanine at $196^{th}$ position (F196) to isoleucine at $282^{th}$ position (I282), the amino acid sequence (region 1-2) from proline at $316^{th}$ position (P316) to asparagine at $394^{th}$ position (N394), the amino acid sequence (region 1-3) from lysine at $510^{th}$ position (K510) to asparagine at $612^{th}$ position (N612), and the amino acid sequence (region 1-4) from threonine at $678^{th}$ position (T678) to histidine at $698^{th}$ position (H698) of the wild-type SpCas9.

The second region may be the amino acid sequence (region 2-1) from methionine at $1^{st}$ position (M1) to threonine at $22^{th}$ position (T22) of the wild-type SpCas9.

The second region may be the amino acid sequence (region 2-2) from proline at $731^{th}$ position (P731) to threonine at $770^{th}$ position (T770) of the wild-type SpCas9.

The second region may be the amino acid sequence (region 2-3) from glutamine at $926^{th}$ position (Q926) to serine at $1040^{th}$ position (S1040) of the wild-type SpCas9.

The second region may be the amino acid sequence (region 2-1) from methionine at $1^{st}$ position (M1) to threonine at $22^{th}$ position (T22) and the amino acid sequence (region 2-2) from proline at $731^{th}$ position (P731) to threonine at $770^{th}$ position (T770) of the wild-type SpCas9.

The second region may be the amino acid sequence (region 2-1) from methionine at $1^{st}$ position (M1) to threonine at $22^{th}$ position (T22) and the amino acid sequence (region 2-3) from glutamine at $926^{th}$ position (Q926) to serine at $1040^{th}$ position (S1040) of the wild-type SpCas9.

The second region may be the amino acid sequence (region 2-2) from proline at $731^{th}$ position (P731) to threonine at $770^{th}$ position (T770) and the amino acid sequence (region 2-3) from glutamine at $926^{th}$ position (Q926) to serine at $1040^{th}$ position (S1040) of the wild-type SpCas9.

The second region may be the amino acid sequence (region 2-1) from methionine at $1^{st}$ position (M1) to threonine at $22^{th}$ position (T22), the amino acid sequence (region 2-2) from proline at $731^{th}$ position (P731) to threonine at $770^{th}$ position (T770) and the amino acid sequence (region 2-3) from glutamine at $926^{th}$ position (Q926) to serine at $1040^{th}$ position (S1040) of the wild-type SpCas9.

The third region may be the amino acid sequence (region 3-1) from lysine at $775^{th}$ position (K775) to leucine at $900^{th}$ position (L900) of the wild-type SpCas9.

The fourth region may be the amino acid sequence (region 4-1) from glutamic acid at $1099^{th}$ position (E1099) to valine at $1139^{th}$ position (V1139) of the wild-type SpCas9.

The TS-SpCas9 may be a SpCas9 variant formed by modifying one or more amino acids selected from the amino acid sequence of the first region of the wild-type SpCas9.

The TS-SpCas9 may be a SpCas9 variant formed by modifying one or more amino acids selected from the amino acid sequence of the region 1-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281 and I282 in the region 1-1 of the wild-type SpCas9.

The TS-SpCas9 may be a SpCas9 variant formed by modifying one or more amino acids selected from the amino acid sequence of the region 1-2 of the wild-type SpCas9.

The TS-SpCas9 may be a SpCas9 variant formed by modifying one or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 in the region 1-2 of the wild-type SpCas9.

The TS-SpCas9 may be a SpCas9 variant formed by modifying one or more amino acids selected from the amino acid sequence of the region 1-3 of the wild-type SpCas9.

The TS-SpCas9 may be a SpCas9 variant formed by modifying one or more amino acids selected from K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-3 of the wild-type SpCas9.

The TS-SpCas9 may be a SpCas9 variant formed by modifying one or more amino acids selected from the amino acid sequence of the region 1-4 of the wild-type SpCas9.

The TS-SpCas9 may be a SpCas9 variant formed by modifying one or more amino acids selected from the group consisting of I679, L680, F682, L683, G687, F688, A689, N692, F693, M694, Q695, L696, I697 and H698 in the region 1-4 of the wild-type SpCas9.

The TS-SpCas9 may be a SpCas9 variant formed by modifying two or more amino acids selected from the amino acid sequences of the region 1-1 and the region 1-2 of the wild-type SpCas9.

The TS-SpCas9 may be a SpCas9 variant formed by modifying two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 in the region 1-1 and the region 1-2 of the wild-type SpCas9.

The TS-SpCas9 may be a SpCas9 variant formed by modifying two or more amino acids selected from the amino acid sequences of the region 1-1 and the region 1-3 of the wild-type SpCas9.

The TS-SpCas9 may be a SpCas9 variant formed by modifying two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-1 and the region 1-3 of the wild-type SpCas9.

The TS-SpCas9 may be a SpCas9 variant formed by modifying two or more amino acids selected from the amino acid sequences of the region 1-1 and the region 1-4 of the wild-type SpCas9.

The TS-SpCas9 may be a SpCas9 variant formed by modifying two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, I679, L680, F682, L683, G687, F688, A689, N692, F693, M694, Q695, L696, I697 and H698 in the region 1-1 and the region 1-4 of the wild-type SpCas9.

The TS-SpCas9 may be a SpCas9 variant formed by modifying two or more amino acids selected from the amino acid sequences of the region 1-2 and the region 1-3 of the wild-type SpCas9.

The TS-SpCas9 may be a SpCas9 variant formed by modifying two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-2 and the region 1-3 of the wild-type SpCas9.

The TS-SpCas9 may be a SpCas9 variant formed by modifying two or more amino acids selected from the amino acid sequences of the region 1-2 and the region 1-4 of the wild-type SpCas9.

The TS-SpCas9 may be a SpCas9 variant formed by modifying two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, I679, L680, F682, L683, G687, F688, A689, N692, F693, M694, Q695, L696, I697 and H698 in the region 1-2 and the region 1-4 of the wild-type SpCas9.

The TS-SpCas9 may be a SpCas9 variant formed by modifying two or more amino acids selected from the amino acid sequences of the region 1-3 and the region 1-4 of the wild-type SpCas9.

The TS-SpCas9 may be a SpCas9 variant formed by modifying two or more amino acids selected from the group consisting of K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-3 and the region 1-4 of the wild-type SpCas9.

The TS-SpCas9 may be a SpCas9 variant formed by modifying three or more amino acids selected from the amino acid sequences of the region 1-1, the region 1-2 and the region 1-3 of the wild-type SpCas9.

The TS-SpCas9 may be a SpCas9 variant formed by modifying three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-1, the region 1-2 and the region 1-3 of the wild-type SpCas9.

The TS-SpCas9 may be a SpCas9 variant formed by modifying three or more amino acids selected from the amino acid sequences of the region 1-1, the region 1-2 and the region 1-4 of the wild-type SpCas9.

The TS-SpCas9 may be a SpCas9 variant formed by modifying three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, I679, L680, F682, L683, G687, F688, A689, N692, F693, M694, Q695, L696, I697 and H698 in the region 1-1, the region 1-2 and the region 1-4 of the wild-type SpCas9.

The TS-SpCas9 may be a SpCas9 variant formed by modifying three or more amino acids selected from the amino acid sequences of the region 1-1, the region 1-3 and the region 1-4 of the wild-type SpCas9.

The TS-SpCas9 may be a SpCas9 variant formed by modifying three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-1, the region 1-3 and the region 1-4 of the wild-type SpCas9.

The TS-SpCas9 may be a SpCas9 variant formed by modifying three or more amino acids selected from the amino acid sequences of the region 1-2, the region 1-3 and the region 1-4 of the wild-type SpCas9.

The TS-SpCas9 may be a SpCas9 variant formed by modifying three or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-2, the region 1-3 and the region 1-4 of the wild-type SpCas9.

The TS-SpCas9 may be a SpCas9 variant formed by modifying four or more amino acids selected from the amino acid sequences of the region 1-1, the region 1-2, the region 1-3 and the region 1-4 of the wild-type SpCas9.

The TS-SpCas9 may be a SpCas9 variant formed by modifying four or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-1, the region 1-2, the region 1-3 and the region 1-4 of the wild-type SpCas9.

In one exemplary embodiment, the TS-SpCas9 may be a SpCas9 variant formed by modifying A203; N277; G366; F539; or I601 of the wild-type SpCas9.

In another exemplary embodiment, the TS-SpCas9 may be a SpCas9 variant formed by modifying A203/N277 (A203 and N277); A203/G366; A203/F539; or A203/I601 of the wild-type SpCas9.

In still another exemplary embodiment, the TS-SpCas9 may be a SpCas9 variant formed by modifying N277/G366; N277/F539; or N277/I601 of the wild-type SpCas9.

In one exemplary embodiment, the TS-SpCas9 may be a SpCas9 variant formed by modifying G366/F539; G366/I601; or F539/I601 of the wild-type SpCas9.

In another exemplary embodiment, the TS-SpCas9 may be a SpCas9 variant formed by modifying A203/N277/G366; A203/N277/F539; A203/N277/I601; A203/G366/F539; A203/G366/I601; A203/F539/I601; N277/G366/F539; N277/G366/I601; or G366/F539/I601 of the wild-type SpCas9.

In still another exemplary embodiment, the TS-SpCas9 may be a SpCas9 variant formed by modifying A203/N277/G366/F539; A203/N277/G366/I601; A203/N277/F539/I601; A203/G366/F539/I601; or N277/G366/F539/I601 of the wild-type SpCas9.

In yet another exemplary embodiment, the TS-SpCas9 may be a SpCas9 variant formed by modifying A203/N277/G366/F539/I601 of the wild-type SpCas9.

The TS-SpCas9 may be a SpCas9 variant formed by modifying one or more amino acids selected from the amino acid sequence of the second region of the wild-type SpCas9.

The TS-SpCas9 may be a SpCas9 variant formed by modifying one or more amino acids selected from the amino acid sequence of the region 2-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20 and I21 in the region 2-1 of the wild-type SpCas9.

The TS-SpCas9 may be a SpCas9 variant formed by modifying one or more amino acids selected from the amino acid sequence of the region 2-2 of the wild-type SpCas9.

The TS-SpCas9 may be a SpCas9 variant formed by modifying one or more amino acids selected from the group consisting of P731, A732, I733, G736, I737, L738, V741, V743, V744, L747, V748, V750, M751, G752, P756, I759, V760, I761, E762, M763, A764, R765, E766 and N767 in the region 2-2 of the wild-type SpCas9.

The TS-SpCas9 may be a SpCas9 variant formed by modifying one or more amino acids selected from the amino acid sequence of the region 2-3 of the wild-type SpCas9.

The TS-SpCas9 may be a SpCas9 variant formed by modifying one or more amino acids selected from the group consisting of I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-3 of the wild-type SpCas9.

The TS-SpCas9 may be a SpCas9 variant formed by modifying two or more amino acids selected from the amino acid sequences of the region 2-1 and the region 2-2 of the wild-type SpCas9.

The TS-SpCas9 may be a SpCas9 variant formed by modifying two or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766 and N767 in the region 2-1 and the region 2-2 of the wild-type SpCas9.

The TS-SpCas9 may be a SpCas9 variant formed by modifying two or more amino acids selected from the amino acid sequences of the region 2-1 and the region 2-3 of the wild-type SpCas9.

The TS-SpCas9 may be a SpCas9 variant formed by modifying two or more amino acids selected from the group consisting of I7, G8, L9, D10, I11, G12, V16, G17, W18, A19, V20, I21, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1 and the region 2-3 of the wild-type SpCas9.

The TS-SpCas9 may be a SpCas9 variant formed by modifying two or more amino acids selected from the amino acid sequences of the region 2-2 and the region 2-3 of the wild-type SpCas9.

The TS-SpCas9 may be a SpCas9 variant formed by modifying two or more amino acids selected from the group consisting of P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-2 and the region 2-3 of the wild-type SpCas9.

The TS-SpCas9 may be a SpCas9 variant formed by modifying three or more amino acids selected from the amino acid sequences of the region 2-1, the region 2-2 and the region 2-3 of the wild-type SpCas9.

The TS-SpCas9 may be a SpCas9 variant formed by modifying three or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and the region 2-3 of the wild-type SpCas9.

In one exemplary embodiment, the TS-SpCas9 may be a SpCas9 variant formed by modifying M763; D965; or F1038 of the wild-type SpCas9.

In another exemplary embodiment, the TS-SpCas9 may be a SpCas9 variant formed by modifying M763/D965; M763/F1038; or D965/F1038 of the wild-type SpCas9.

In still another exemplary embodiment, the TS-SpCas9 may be a SpCas9 variant formed by modifying M763/D965/F1038 of the wild-type SpCas9.

The TS-SpCas9 may be a SpCas9 variant formed by modifying one or more amino acids selected from the amino acid sequence of the third region of the wild-type SpCas9.

The TS-SpCas9 may be a SpCas9 variant formed by modifying one or more amino acids selected from the amino acid sequence of the region 3-1 of the wild-type SpCas9.

The TS-SpCas9 may be a SpCas9 variant formed by modifying one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying K890 of the wild-type SpCas9.

The TS-SpCas9 may be a SpCas9 variant formed by modifying one or more amino acids selected from the amino acid sequence of the fourth region of the wild-type SpCas9.

The TS-SpCas9 may be a SpCas9 variant formed by modifying one or more amino acids selected from the amino acid sequence of the region 4-1 of the wild-type SpCas9.

The TS-SpCas9 may be a SpCas9 variant formed by modifying one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying T1102 or D1127 of the wild-type SpCas9.

In another exemplary embodiment, the TS-SpCas9 may be a SpCas9 variant formed by modifying T1102/D1127 of the wild-type SpCas9.

The TS-SpCas9 may be a SpCas9 variant formed by modifying two or more amino acids selected from the amino acid sequences of the first region and the second region of the wild-type SpCas9. Here, the two or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; and one or more amino acids selected from the amino acid sequence(s) of the region 2-1, the region 2-2 and/or the region 2-3 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; and one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 or the region 2-3 of the wild-type SpCas9, respectively.

In one exemplary embodiment, the TS-SpCas9 may be a SpCas9 variant formed by modifying A203/M763; A203/D965; A203/F1038; A203/M763/D965; A203/M763/F1038; A203/D965/F1038; A203/M763/D965/F1038; N277/M763; N277/D965; N277/F1038; N277/M763/D965; N277/M763/F1038; N277/D965/F1038; N277/M763/D965/F1038; G366/M763; G366/D965; G366/F1038; G366/M763/D965; G366/M763/F1038; G366/D965/F1038; G366/M763/D965/F1038; F539/M763; F539/D965; F539/F1038; F539/M763/D965; F539/M763/F1038; F539/D965/F1038; F539/M763/D965/F1038; I601/M763; I601/D965; I601/F1038; I601/M763/D965; I601/M763/F1038; I601/D965/F1038; or I601/M763/D965/F1038 of the wild-type SpCas9.

In another exemplary embodiment, the TS-SpCas9 may be a SpCas9 variant formed by modifying A203/N277/M763; A203/N277/D965; A203/N277/F1038; A203/N277/M763/D965; A203/N277/M763/F1038; A203/N277/D965/F1038; A203/N277/M763/D965/F1038; A203/G366/M763;

A203/G366/D965; A203/G366/F1038; A203/G366/M763/D965; A203/G366/M763/F1038; A203/G366/D965/F1038; A203/G366/M763/D965/F1038; A203/F539/M763; A203/F539/D965; A203/F539/F1038; A203/F539/M763/D965; A203/F539/M763/F1038; A203/F539/D965/F1038; A203/F539/M763/D965/F1038; A203/I601/M763; A203/I601/D965; A203/I601/F1038; A203/I601/M763/D965; A203/I601/M763/F1038; A203/I601/D965/F1038; A203/I601/M763/D965/F1038; N277/G366/M763; N277/G366/D965; N277/G366/F1038; N277/G366/M763/D965; N277/G366/M763/F1038; N277/G366/D965/F1038; N277/G366/M763/D965/F1038; N277/F539/M763; N277/F539/D965; N277/F539/F1038; N277/F539/M763/D965; N277/F539/M763/F1038; N277/F539/D965/F1038; N277/F539/M763/D965/F1038; N277/I601/M763; N277/I601/D965; N277/I601/F1038; N277/I601/M763/D965; N277/I601/M763/F1038; N277/I601/D965/F1038; N277/I601/M763/D965/F1038; G366/F539/M763; G366/F539/D965; G366/F539/F1038; G366/F539/M763/D965; G366/F539/M763/F1038; G366/F539/D965/F1038; G366/F539/M763/D965/F1038; G366/I601/M763; G366/I601/D965; G366/I601/F1038; G366/I601/M763/D965; G366/I601/M763/F1038; G366/I601/D965/F1038; G366/I601/M763/D965/F1038; F539/I601/M763; F539/I601/D965; F539/I601/F1038; F539/I601/M763/D965; F539/I601/M763/F1038; F539/I601/D965/F1038; or F539/I601/M763/D965/F1038 of the wild-type SpCas9.

In still another exemplary embodiment, the TS-SpCas9 may be a SpCas9 variant formed by modifying A203/N277/G366/M763; A203/N277/G366/D965; A203/N277/G366/F1038; A203/N277/G366/M763/D965; A203/N277/G366/M763/F1038; A203/N277/G366/D965/F1038; A203/N277/G366/M763/D965/F1038; A203/N277/F539/M763; A203/N277/F539/D965; A203/N277/F539/F1038; A203/N277/F539/M763/D965; A203/N277/F539/M763/F1038; A203/N277/F539/D965/F1038; A203/N277/F539/M763/D965/F1038; A203/N277/I601/M763; A203/N277/I601/D965; A203/N277/I601/F1038; A203/N277/I601/M763/D965; A203/N277/I601/M763/F1038; A203/N277/I601/D965/F1038; A203/N277/I601/M763/D965/F1038; A203/G366/F539/M763; A203/G366/F539/D965; A203/G366/F539/F1038; A203/G366/F539/M763/D965; A203/G366/F539/M763/F1038; A203/G366/F539/D965/F1038; A203/G366/F539/M763/D965/F1038; A203/G366/I601/M763; A203/G366/I601/D965; A203/G366/I601/F1038; A203/G366/I601/M763/D965; A203/G366/I601/M763/F1038; A203/G366/I601/D965/F1038; A203/G366/I601/M763/D965/F1038; A203/F539/I601/M763; A203/F539/I601/D965; A203/F539/I601/F1038; A203/F539/I601/M763/D965; A203/F539/I601/M763/F1038; A203/F539/I601/D965/F1038; A203/F539/I601/M763/D965/F1038; N277/G366/F539/M763; N277/G366/F539/D965; N277/G366/F539/F1038; N277/G366/F539/M763/D965; N277/G366/F539/M763/F1038; N277/G366/F539/D965/F1038; N277/G366/I601/M763; N277/G366/I601/D965; N277/G366/I601/F1038; N277/G366/I601/M763/D965; N277/G366/I601/M763/F1038; N277/G366/I601/D965/F1038; N277/G366/I601/M763/D965/F1038; G366/F539/I601/M763; G366/F539/I601/D965; G366/F539/I601/F1038; G366/F539/I601/M763/D965; G366/F539/I601/M763/F1038; G366/F539/I601/D965/F1038; or G366/F539/I601/M763/D965/F1038 of the wild-type SpCas9.

In one exemplary embodiment, the TS-SpCas9 may be a SpCas9 variant formed by modifying A203/N277/G366/F539/M763; A203/N277/G366/F539/D965; A203/N277/G366/F539/F1038; A203/N277/G366/F539/M763/D965;

A203/N277/G366/F539/M763/F1038; A203/N277/G366/ F539/D965/F1038; A203/N277/G366/F539/M763/D965/ F1038; A203/N277/G366/I601/M763; A203/N277/G366/ I601/D965; A203/N277/G366/I601/F1038; A203/N277/ G366/I601/M763/D965; A203/N277/G366/I601/M763/ F1038; A203/N277/G366/I601/D965/F1038; A203/N277/ G366/I601/M763/D965/F1038; N277/G366/F539/I601/ M763; N277/G366/F539/I601/D965; N277/G366/F539/ I601/F1038; N277/G366/F539/I601/M763/D965; N277/ G366/F539/I601/M763/F1038; N277/G366/F539/I601/ D965/F1038; N277/G366/F539/I601/M763/D965/F1038; A203/N277/G366/F539/I601/M763; A203/N277/G366/ F539/I601/D965; A203/N277/G366/F539/I601/F1038; A203/N277/G366/F539/I601/M763/D965; A203/N277/ G366/F539/I601/M763/F1038; A203/N277/G366/F539/ I601/D965/F1038; or A203/N277/G366/F539/I601/M763/ D965/F1038 of the wild-type SpCas9.

The TS-SpCas9 may be a SpCas9 variant formed by modifying two or more amino acids selected from the amino acid sequences of the first region and the third region of the wild-type SpCas9. Here, the two or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; and one or more amino acids selected from the amino acid sequence of the region 3-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; and one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying A203/K890; N277/ K890; G366/K890; F539/K890; or I601/K890 of the wild-type SpCas9.

In another exemplary embodiment, the TS-SpCas9 may be a SpCas9 variant formed by modifying A203/N277/ K890; A203/G366/K890; A203/F539/K890; A203/I601/ K890; N277/G366/K890; N277/F539/K890; N277/I601/ K890; G366/F539/K890; G366/I601/K890; or F539/I601/ K890 of the wild-type SpCas9.

In still another exemplary embodiment, the TS-SpCas9 may be a SpCas9 variant formed by modifying A203/N277/

G366/K890; A203/N277/F539/K890; A203/N277/I601/ K890; A203/G366/F539/K890; A203/G366/I601/K890; A203/F539/I601/K890; N277/G366/F539/K890; N277/ G366/I601/K890; or G366/F539/I601/K890 of the wild-type SpCas9.

In one exemplary embodiment, the TS-SpCas9 may be a SpCas9 variant formed by modifying A203/N277/G366/ F539/K890; A203/N277/G366/I601/K890; or N277/G366/ F539/I601/K890 of the wild-type SpCas9.

In another exemplary embodiment, the TS-SpCas9 may be a SpCas9 variant formed by modifying A203/N277/ G366/F539/I601/K890 of the wild-type SpCas9.

The TS-SpCas9 may be a SpCas9 variant formed by modifying two or more amino acids selected from the amino acid sequences of the first region and the fourth region of the wild-type SpCas9. Here, the two or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; and one or more amino acids selected from the amino acid sequence of the region 4-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying A203/T1102; N277/ T1102; G366/T1102; F539/T1102; I601/T1102; A203/ D1127; N277/D1127; G366/D1127; F539/D1127; I601/ D1127; A203/T1102/D1127; N277/T1102/D1127; G366/ T1102/D1127; F539/T1102/D1127; or I601/T1102/D1127 of the wild-type SpCas9.

In another exemplary embodiment, the TS-SpCas9 may be a SpCas9 variant formed by modifying A203/N277/ T1102; A203/G366/T1102; A203/F539/T1102; A203/I601/ T1102; N277/G366/T1102; N277/F539/T1102; N277/I601/ T1102; G366/F539/T1102; G366/I601/T1102; F539/I601/ T1102; A203/N277/D1127; A203/G366/D1127; A203/ F539/D1127; A203/I601/D1127; N277/G366/D1127; N277/ F539/D1127; N277/I601/D1127; G366/F539/D1127; G366/ I601/D1127; F539/I601/D1127; A203/N277/T1102/D1127; A203/G366/T1102/D1127; A203/F539/T1102/D1127; A203/I601/T1102/D1127; N277/G366/T1102/D1127; N277/F539/T1102/D1127; N277/I601/T1102/D1127; G366/ F539/T1102/D1127; G366/I601/T1102/D1127; or F539/ I601/T1102/D1127 of the wild-type SpCas9.

In still another exemplary embodiment, the TS-SpCas9 may be a SpCas9 variant formed by modifying A203/N277/ G366/T1102; A203/N277/F539/T1102; A203/N277/I601/ T1102; A203/G366/F539/T1102; A203/G366/I601/T1102; A203/F539/I601/T1102; N277/G366/F539/T1102; N277/ G366/I601/T1102; G366/F539/I601/T1102; A203/N277/ G366/D1127; A203/N277/F539/D1127; A203/N277/I601/ D1127; A203/G366/F539/D1127; A203/G366/I601/D1127; A203/F539/I601/D1127; N277/G366/F539/D1127; N277/ G366/I601/D1127; G366/F539/I601/D1127; A203/N277/ G366/T1102/D1127; A203/N277/F539/T1102/D1127; A203/N277/I601/T1102/D1127; A203/G366/F539/T1102/ D1127; A203/G366/I601/T1102/D1127; A203/F539/I601/ T1102/D1127; N277/G366/F539/T1102/D1127; N277/ G366/I601/T1102/D1127; or G366/F539/I601/T1102/ D1127 of the wild-type SpCas9.

In one exemplary embodiment, the TS-SpCas9 may be a SpCas9 variant formed by modifying A203/N277/G366/ F539/T1102; A203/N277/G366/I601/T1102; N277/G366/ F539/I601/T1102; A203/N277/G366/F539/D1127; A203/ N277/G366/I601/D1127; N277/G366/F539/I601/D1127; A203/N277/G366/F539/T1102/D1127; A203/N277/G366/ I601/T1102/D1127; or N277/G366/F539/I601/T1102/ D1127 of the wild-type SpCas9.

In another exemplary embodiment, the TS-SpCas9 may be a SpCas9 variant formed by modifying A203/N277/ G366/F539/I601/T1102; A203/N277/G366/F539/I601/ D1127; or A203/N277/G366/F539/I601/T1102/D1127 of the wild-type SpCas9.

The TS-SpCas9 may be a SpCas9 variant formed by modifying two or more amino acids selected from the amino acid sequences of the second region and the third region of the wild-type SpCas9. Here, the two or more amino acids may be present in different regions, respectively.

The TS-SpCas9 may be a SpCas9 variant formed by modifying one or more amino acids selected from the amino acid sequences of the region 2-1, the region 2-2 and/or the region 2-3; and one or more amino acids selected from the amino acid sequence of the region 3-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; and one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying M763/K890; K890/ D965; or K890/F1038 of the wild-type SpCas9.

In another exemplary embodiment, the TS-SpCas9 may be a SpCas9 variant formed by modifying M763/K890/ D965; M763/K890/F1038; or K890/D965/F1038 of the wild-type SpCas9.

In still another exemplary embodiment, the TS-SpCas9 may be a SpCas9 variant formed by modifying M763/K890/ D965/F1038 of the wild-type SpCas9.

The TS-SpCas9 may be a SpCas9 variant formed by modifying two or more amino acids selected from the amino acid sequences of the second region and the fourth region of the wild-type SpCas9. Here, the two or more amino acids may be present in different regions, respectively.

The TS-SpCas9 may be a SpCas9 variant formed by modifying one or more amino acids selected from the amino acid sequence(s) of the region 2-1, the region 2-2 and/or the region 2-3; and one or more amino acids selected from the amino acid sequence of the region 4-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying M763/T1102; D965/ T1102; F1038/T1102; M763/D1127; D965/D1127; F1038/ D1127; M763/T1102/D1127; D965/T1102/D1127; or F1038/T1102/D1127 of the wild-type SpCas9.

In another exemplary embodiment, the TS-SpCas9 may be a SpCas9 variant formed by modifying M763/D965/ T1102; M763/F1038/T1102; D965/F1038/T1102; M763/ D965/D1127; M763/F1038/D1127; D965/F1038/D1127; M763/D965/T1102/D1127; M763/F1038/T1102/D1127; or D965/F1038/T1102/D1127 of the wild-type SpCas9.

In still another exemplary embodiment, the TS-SpCas9 may be a SpCas9 variant formed by modifying M763/D965/ F1038/T1102; M763/D965/F1038/D1127; or M763/D965/ F1038/T1102/D1127 of the wild-type SpCas9.

The TS-SpCas9 may be a SpCas9 variant formed by modifying two or more amino acids selected from the amino acid sequences of the third region and the fourth region of the wild-type SpCas9. Here, the two or more amino acids may be present in different regions, respectively.

The TS-SpCas9 may be a SpCas9 variant formed by modifying one or more amino acids selected from the amino acid sequence in the region 3-1; and one or more amino acids selected from the amino acid sequence in the region 4-1 of the wild-type SpCas9.

The TS-SpCas9 may be a SpCas9 variant formed by modifying one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying K890/T1102; K890/D1127; or K890/T1102/D1127 of the wild-type SpCas9.

The TS-SpCas9 may be a SpCas9 variant formed by modifying three or more amino acids selected from the amino acid sequences of the first region, the second region and the third region of the wild-type SpCas9. Here, the three or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; one or more amino acids selected from the amino acid sequences of the region 2-1, the region 2-2 and/or the region 2-3; and one or more amino acids selected from the amino acid sequence of the region 3-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; and one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying A203/M763/K890; A203/K890/D965; A203/K890/F1038; A203/M763/K890/D965; A203/M763/K890/F1038; A203/K890/D965/F1038; A203/M763/K890/D965/F1038; N277/M763/K890; N277/K890/D965; N277/K890/F1038; N277/M763/K890/D965;

N277/M763/K890/F1038; N277/K890/D965/F1038; N277/M763//K890D965/F1038; G366/M763/K890; G366/K890/D965; G366/K890/F1038; G366/M763/K890/D965; G366/M763/K890/F1038; G366/K890/D965/F1038; G366/M763/K890/D965/F1038; F539/M763/K890; F539/K890/D965; F539/K890/F1038; F539/M763/K890/D965; F539/M763/K890/F1038; F539/K890/D965/F1038; F539/M763/K890/D965/F1038; I601/M763/K890; I601/K890/D965; I601/K890/F1038; I601/M763/K890/D965; I601/M763/K890/F1038; I601/K890/D965/F1038; or I601/M763/K890/D965/F1038 of the wild-type SpCas9.

In another exemplary embodiment, the TS-SpCas9 may be a SpCas9 variant formed by modifying A203/N277/M763/K890; A203/N277/K890/D965; A203/N277/K890/F1038; A203/N277/M763/K890/D965; A203/N277/M763/K890/F1038; A203/N277/K890/D965/F1038; A203/N277/M763/K890/D965/F1038; A203/G366/M763/K890; A203/G366/K890/D965; A203/G366/K890/F1038; A203/G366/M763/K890/D965; A203/G366/M763/K890/F1038; A203/G366/K890/D965/F1038; A203/G366/M763/K890/D965/F1038; A203/F539/M763/K890; A203/F539/K890/D965; A203/F539/K890/F1038; A203/F539/M763/K890/D965; A203/F539/M763/K890/F1038; A203/F539/K890/D965/F1038; A203/F539/M763/K890/D965/F1038; A203/I601/M763/K890; A203/I601/K890/D965; A203/I601/K890/F1038; A203/I601/M763/K890/D965; A203/I601/M763/K890/F1038; A203/I601/K890/D965/F1038; A203/I601/M763/K890/D965/F1038; N277/G366/M763/K890; N277/G366/K890/D965; N277/G366/K890/F1038; N277/G366/M763/K890/D965; N277/G366/M763/K890/F1038; N277/G366/K890/D965/F1038; N277/G366/M763/K890/D965/F1038; N277/F539/M763/K890; N277/F539/K890/D965; N277/F539/K890/F1038; N277/F539/M763/K890/D965; N277/F539/M763/K890/F1038; N277/F539/K890/D965/F1038; N277/F539/M763/K890/D965/F1038; N277/I601/M763/K890; N277/I601/K890/D965; N277/I601/K890/F1038; N277/I601/M763/K890/D965; N277/I601/M763/K890/F1038; N277/I601/K890/D965/F1038; N277/I601/M763/K890/D965/F1038; G366/F539/M763/K890; G366/F539/K890/D965; G366/F539/K890/F1038; G366/F539/M763/K890/D965; G366/F539/M763/K890/F1038; G366/F539/K890/D965/F1038; G366/F539/M763/K890/D965; G366/I601/M763/K890; G366/I601/K890/D965; G366/I601/K890/F1038; G366/I601/M763/K890/D965; G366/I601/M763/K890/F1038; G366/I601/M763/K890/D965/F1038; F539/I601/M763/K890; F539/I601/K890/D965; F539/I601/K890/F1038; F539/I601/M763/K890/D965; F539/I601/M763/K890/F1038; F539/I601/K890/D965/F1038; or F539/I601/M763/K890/D965/F1038 of the wild-type SpCas9.

In still another exemplary embodiment, the TS-SpCas9 may be a SpCas9 variant formed by modifying A203/N277/G366/M763/K890; A203/N277/G366/K890/D965; A203/N277/G366/K890/F1038; A203/N277/G366/M763/K890/D965; A203/N277/G366/M763/K890/F1038; A203/N277/G366/K890/D965/F1038; A203/N277/G366/M763/K890/D965/F1038; A203/N277/F539/M763/K890; A203/N277/F539/K890/D965; A203/N277/F539/K890/F1038; A203/N277/F539/M763/K890/D965; A203/N277/F539/M763/K890/F1038; A203/N277/F539/K890/D965/F1038; A203/N277/F539/M763/K890/D965/F1038; A203/N277/I601/M763/K890; A203/N277/I601/K890/D965; A203/N277/I601/K890/F1038; A203/N277/I601/M763/K890/D965; A203/N277/I601/M763/K890/F1038; A203/N277/I601/K890/D965/F1038; A203/N277/I601/M763/K890/D965/F1038; A203/G366/F539/M763/K890; A203/G366/F539/K890/D965; A203/G366/F539/K890/F1038; A203/G366/

F539/M763/K890/D965; A203/G366/F539/M763/K890/
F1038; A203/G366/F539/K890/D965/F1038; A203/G366/
F539/M763/K890/D965/F1038; A203/G366/I601/M763/
K890; A203/G366/I601/K890/D965; A203/G366/I601/
K890/F1038; A203/G366/I601/M763/K890/D965; A203/
G366/I601/M763/K890/F1038; A203/G366/I601/K890/
D965/F1038; A203/G366/I601/M763/K890/D965/F1038;
A203/F539/I601/M763/K890; A203/F539/I601/K890/
D965; A203/F539/I601/K890/F1038; A203/F539/I601/
M763/K890/D965; A203/F539/I601/M763/K890/F1038;
A203/F539/I601/K890/D965/F1038; A203/F539/I601/
M763/K890/D965/F1038; N277/G366/F539/M763/K890;
N277/G366/F539/K890/D965; N277/G366/F539/K890/
F1038; N277/G366/F539/M763/K890/D965; N277/G366/
F539/M763/K890/F1038; N277/G366/F539/K890/D965/
F1038; N277/G366/F539/M763/K890/D965/F1038; N277/
G366/I601/M763/K890; N277/G366/I601/K890/D965;
N277/G366/I601/K890/F1038; N277/G366/I601/M763/
K890/D965; N277/G366/I601/M763/K890/F1038; N277/
G366/I601/K890/D965/F1038; N277/G366/I601/M763/
K890/D965/F1038; G366/F539/I601/M763/K890; G366/
F539/I601/K890/D965; G366/F539/I601/K890/F1038;
G366/F539/I601/M763/K890/D965; G366/F539/I601/
M763/K890/F1038; G366/F539/I601/K890/D965/F1038;
or G366/F539/I601/M763/K890/D965/F1038 of the wild-
type SpCas9.

In one exemplary embodiment, the TS-SpCas9 may be a
SpCas9 variant formed by modifying A203/N277/G366/
F539/M763/K890; A203/N277/G366/F539/K890/D965;
A203/N277/G366/F539/K890/F1038; A203/N277/G366/
F539/M763/K890/D965; A203/N277/G366/F539/M763/
K890/F1038; A203/N277/G366/F539/K890/D965/F1038;
A203/N277/G366/F539/M763/K890/D965/F1038; A203/
N277/G366/I601/M763/K890; A203/N277/G366/I601/
K890/D965; A203/N277/G366/I601/K890/F1038; A203/
N277/G366/I601/M763/K890/D965; A203/N277/G366/
I601/M763/K890/F1038; A203/N277/G366/I601/K890/
D965/F1038; A203/N277/G366/I601/M763/K890/D965/
F1038; N277/G366/F539/I601/M763/K890; N277/G366/
F539/I601/K890/D965; N277/G366/F539/I601/K890/
F1038; N277/G366/F539/I601/M763/K890/D965; N277/
G366/F539/I601/M763/K890/F1038; N277/G366/F539/
I601/K890/D965/F1038; N277/G366/F539/I601/M763/
K890/D965/F1038; A203/N277/G366/F539/I601/M763/
K890; A203/N277/G366/F539/I601/K890/D965; A203/
N277/G366/F539/I601/K890/F1038; A203/N277/G366/
F539/I601/M763/K890/D965; A203/N277/G366/F539/
I601/M763/K890/F1038; A203/N277/G366/F539/I601/
K890/D965/F1038; or A203/N277/G366/F539/I601/M763/
K890/D965/F1038 of the wild-type SpCas9.

The TS-SpCas9 may be a SpCas9 variant formed by
modifying three or more amino acids selected from amino
acid sequences of the first region, the second region and the
fourth region of the wild-type SpCas9. Here, the three or
more amino acids may be present in different regions,
respectively.

The TS-SpCas9 may be a SpCas9 variant formed by
modifying one or more amino acids selected from the amino
acid sequence(s) of the region 1-1, the region 1-2, the region
1-3 and/or the region 1-4; one or more amino acids selected
from the amino acid sequence(s) of the region 2-1, the
region 2-2 and/or the region 2-3; and one or more amino
acids selected from the amino acid sequence of the region
4-1 of the wild-type SpCas9.

The TS-SpCas9 may be a SpCas9 variant formed by
modifying one or more amino acids selected from the group
consisting of N199, I201, N202, A203, G205, V206, A208, A210, I211, L212, A214, L216, L222, N224, L225, I226,
A227, Q228, L229, G231, N235, G236, L237, G239, N240,
L241, I242, A243, L244, L246, G247, L248, N251, N255,
L258, A259, A262, L264, Q265, L266, L275, N277, L278,
L279, A280, Q281, I282, P316, L317, A319, M321, I322,
L332, L334, L335, A337, L338, V339, L343, P344, I350,
F351, F352, G358, A360, G361, I363, G365, G366, A367,
F372, F375, I376, P378, I379, L380, M383, G385, L389,
L390, V391, L393, L513, L514, F518, V520, L524, V527,
V530, G533, M534, P537, A538, F539, L540, G542, A547,
I548, V549, L551, L552, F553, V559, V561, L564, F569,
I572, C574, F575, V578, I580, G582, V583, F587, A589,
L591, G592, L597, L598, I600, I601, F606, L607, I679,
L680, F682, L683, G687, F688, A689, F693, M694, L696
and I697 in the region 1-1, the region 1-2, the region 1-3
and/or the region 1-4; one or more amino acids selected from
the group consisting of I7, G8, L9, D10, I11, G12, V16, G17,
W18, A19, V20, I21, P731, A732, I733, G736, I737, L738,
V741, V743, V744, L747, V748, V750, M751, G752, P756,
I759, V760, I761, E762, M763, A764, R765, E766, N767,
I927, V931, A932, I934, L935, M939, L949, I950, V953,
V955, I956, L958, L962, V963, D965, F966, F970, F972,
V975, U978, Y981, H982, H983, A984, H985, D986, A987,
Y988, L989, A991, V992, V993, G994, A996, L997, I998,
P1002, L1004, F1008, V1009, G1011, V1015, V1018,
M1021, I1022, A1023, I1029, G1030, A1032, A1034,
Y1036, F1037, F1038 and Y1039 in the region 2-1, the
region 2-2 and/or the region 2-3; and one or more amino
acids selected from the group consisting of T1102, S1106,
E1108, S1116, D1117, D1125, D1127, D1135, S1136 and
T1138 in the region 4-1 of the wild-type SpCas9.

In one exemplary embodiment, the TS-SpCas9 may be a
SpCas9 variant formed by modifying A203/M763/T1102;
A203//D965T1102; A203//F1038T1102; A203/M763/D965/
T1102; A203/M763/F1038/T1102; A203/D965/F1038/
T1102; A203/M763/D965/F1038/T1102; N277/M763/
T1102; N277/D965/T1102; N277/F1038/T1102; N277/
M763/D965/T1102; N277/M763/F1038/T1102; N277/
D965/F1038/T1102; N277/M763/D965/F1038/T1102;
G366/M763/T1102; G366/D965/T1102; G366/F1038/
T1102; G366/M763/D965/T1102; G366/M763/F1038/
T1102; G366/D965/F1038/T1102; G366/M763/D965/
F1038/T1102; F539/M763/T1102; F539/D965/T1102;
F539/F1038/T1102; F539/M763/D965/T1102; F539/M763/
F1038/T1102; F539/D965/F1038/T1102; F539/M763/
D965/F1038/T1102; I601/M763/T1102; I601/D965/T1102;
I601/F1038/T1102; I601/M763/D965/T1102; I601/M763/
F1038/T1102; I601/D965/F1038/T1102; I601/M763/D965/
F1038/T1102; A203/M763/D1127; A203/D965/D1127;
A203/F1038/D1127; A203/M763/D965/D1127; A203/
M763/F1038/D1127; A203/D965/F1038/D1127; A203/
M763/D965/F1038/D1127; N277/M763/D1127; N277/
D965/D1127; N277/F1038/D1127; N277/M763/D965/
D1127; N277/M763/F1038/D1127; N277/D965/F1038/
D1127; N277/M763/D965/F1038/D1127; G366/M763/
D1127; G366/D965/D1127; G366/F1038/D1127; G366/
M763/D965/D1127; G366/M763/F1038/D1127; G366/
D965/F1038/D1127; G366/M763/D965/F1038/D1127;
F539/M763/D1127; F539/D965/D1127; F539/F1038/
D1127; F539/M763/D965/D1127; F539/M763/F1038/
D1127; F539/D965/F1038/D1127; F539/M763/D965/
F1038/D1127; I601/M763/D1127; I601/D965/D1127; I601/
F1038/D1127; I601/M763/D965/D1127; I601/M763/
F1038D1127; I601/D965/F1038/D1127; or I601/M763/
D965/F1038/D1127 of the wild-type SpCas9.

In another exemplary embodiment, the TS-SpCas9 may
be a SpCas9 variant formed by modifying A203/M763/

T1102/D1127; A203/D965/T1102/D1127; A203/F1038/ T1102/D1127; A203/M763/D965/T1102/D1127; A203/ M763/F1038/T1102/D1127; A203/D965/F1038/T1102/ D1127; A203/M763/D965/F1038/T1102/D1127; N277/ M763/T1102/D1127; N277/D965/T1102/D1127; N277/ F1038/T1102/D1127; N277/M763/D965/T1102/D1127; N277/M763/F1038/T1102/D1127; N277/D965/F1038/ T1102/D1127; N277/M763/D965/F1038/T1102/D1127; G366/M763/T1102/D1127; G366/D965/T1102/D1127; G366/F1038/T1102/D1127; G366/M763/D965/T1102/ D1127; G366/M763/F1038/T1102/D1127; G366/D965/ F1038/T1102/D1127; G366/M763/D965/F1038/T1102/ D1127; F539/M763/T1102/D1127; F539/D965/T1102/ D1127; F539/F1038/T1102/D1127; F539/M763/D965/ T1102/D1127; F539/M763/F1038/T1102/D1127; F539/ D965/F1038/T1102/D1127; F539/M763/D965/F1038/ T1102/D1127; I601/M763/T1102/D1127; I601/D965/ T1102/D1127; I601/F1038/T1102/D1127; I601/M763/ D965/T1102/D1127; I601/M763/F1038T1102/D1127; I601/ D965/F1038/T1102/D1127; or I601/M763/D965/F1038/ T1102/D1127 of the wild-type SpCas9.

In one exemplary embodiment, the TS-SpCas9 may be a SpCas9 variant formed by modifying A203/N277/M763/ T1102; A203/N277/D965/T1102; A203/N277/F1038/ T1102; A203/N277/M763/D965/T1102; A203/N277/M763/ F1038/T1102; A203/N277/D965/F1038/T1102; A203/ N277/M763/D965/F1038/T1102; A203/G366/M763/ T1102; A203/G366/D965/T1102; A203/G366/F1038/ T1102; A203/G366/M763/D965/T1102; A203/G366/M763/ F1038/T1102; A203/G366/D965/F1038/T1102; A203/ G366/M763/D965/F1038/T1102; A203/F539/M763/T1102; A203/F539/D965/T1102; A203/F539/F1038/T1102; A203/ F539/M763/D965/T1102; A203/F539/M763/F1038/T1102; A203/F539/D965/F1038/T1102; A203/F539/M763/D965/ F1038/T1102; A203/I601/M763/T1102; A203/I601/D965/ T1102; A203/I601/F1038/T1102; A203/I601/M763/D965/ T1102; A203/I601/M763/F1038/T1102; A203/I601/D965/ F1038/T1102; A203/I601/M763/D965/F1038/T1102; N277/ G366/M763/T1102; N277/G366/D965/T1102; N277/G366/ F1038/T1102; N277/G366/M763/D965/T1102; N277/ G366/M763/F1038/T1102; N277/G366/D965/F1038/ T1102; N277/G366/M763/D965/F1038/T1102; N277/F539/ M763/T1102; N277/F539/D965/T1102; N277/F539/F1038/ T1102; N277/F539/M763/D965/T1102; N277/F539/M763/ F1038/T1102; N277/F539/D965/F1038/T1102; N277/F539/ M763/D965/F1038/T1102; N277/I601/M763/T1102; N277/ I601/D965/T1102; N277/I601/F1038/T1102; N277/I601/ M763/D965/T1102; N277/I601/M763/F1038/T1102; N277/ I601/D965/F1038/T1102; N277/I601/M763/D965/F1038/ T1102; G366/F539/M763/T1102; G366/F539/D965/T1102; G366/F539/F1038/T1102; G366/F539/M763/D965/T1102; G366/F539/M763/F1038/T1102; G366/F539/D965/F1038/ T1102; G366/F539/M763/D965/F1038/T1102; G366/I601/ M763/T1102; G366/I601/D965/T1102; G366/I601/F1038/ T1102; G366/I601/M763/D965/T1102; G366/I601/M763/ F1038/T1102; G366/I601/D965/F1038/T1102; G366/I601/ M763/D965/F1038/T1102; F539/I601/M763/T1102; F539/ I601/D965/T1102; F539/I601/F1038/T1102; F539/I601/ M763/D965/T1102; F539/I601/M763/F1038/T1102; F539/ I601/D965/F1038/T1102; F539/I601/M763/D965/F1038/ T1102; A203/N277/M763/D1127; A203/N277/D965/ D1127; A203/N277/F1038/D1127; A203/N277/M763/ D965/D1127; A203/N277/M763/F1038/D1127; A203/ N277/D965/F1038/D1127; A203/N277/M763/D965/F1038/ D1127; A203/G366/M763/D1127; A203/G366/D965/ D1127; A203/G366/F1038/D1127; A203/G366/M763/ D965/D1127; A203/G366/M763/F1038/D1127; A203/

G366/D965/F1038/D1127; A203/G366/M763/D965/F1038/ D1127; A203/F539/M763/D1127; A203/F539/D965/ D1127; A203/F539/F1038/D1127; A203/F539/M763/D965/ D1127; A203/F539/M763/F1038/D1127; A203/F539/D965/ F1038/D1127; A203/F539/M763/D965/F1038/D1127; A203/I601/M763/D1127; A203/I601/D965/D1127; A203/ I601/F1038/D1127; A203/I601/M763/D965/D1127; A203/ I601/M763/F1038/D1127; A203/I601/D965/F1038/D1127; A203/I601/M763/D965/F1038/D1127; N277/G366/M763/ D1127; N277/G366/D965/D1127; N277/G366/F1038/ D1127; N277/G366/M763/D965/D1127; N277/G366/ M763/F1038/D1127; N277/G366/D965/F1038/D1127; N277/G366/M763/D965/F1038/D1127; N277/F539/M763/ D1127; N277/F539/D965/D1127; N277/F539/F1038/ D1127; N277/F539/M763/D965/D1127; N277/F539/M763/ F1038/D1127; N277/F539/D965/F1038/D1127; N277/ F539/M763/D965/F1038/D1127; N277/I601/M763/D1127; N277/I601/D965/D1127; N277/I601/F1038/D1127; N277/ I601/M763/D965/D1127; N277/I601/M763/F1038/D1127; N277/I601/D965/F1038/D1127; N277/I601/M763/D965/ F1038/D1127; G366/F539/M763/D1127; G366/F539/D965/ D1127; G366/F539/F1038/D1127; G366/F539/M763/D965/ D1127; G366/F539/M763/F1038/D1127; G366/F539/D965/ F1038/D1127; G366/F539/M763/D965/F1038/D1127; G366/I601/M763/D1127; G366/I601/D965/D1127; G366/ I601/F1038/D1127; G366/I601/M763/D965/D1127; G366/ I601/M763/F1038/D1127; G366/I601/D965/F1038/D1127; G366/I601/M763/D965/F1038/D1127; F539/I601/M763/ D1127; F539/I601/D965/D1127; F539/I601/F1038/D1127; F539/I601/M763/D965/D1127; F539/I601/M763/F1038/ D1127; F539/I601/D965/F1038/D1127; or F539/I601/ M763/D965/F1038/D1127 of the wild-type SpCas9.

In another exemplary embodiment, the TS-SpCas9 may be a SpCas9 variant formed by modifying A203/N277/ M763/T1102/D1127; A203/N277/D965/T1102/D1127; A203/N277/F1038/T1102/D1127; A203/N277/M763/D965/ T1102/D1127; A203/N277/M763/F1038/T1102/D1127; A203/N277/D965/F1038/T1102/D1127; A203/N277/M763/ D965/F1038/T1102/D1127; A203/G366/M763/T1102/ D1127; A203/G366/D965/T1102/D1127; A203/G366/ F1038/T1102/D1127; A203/G366/M763/D965/T1102/ D1127; A203/G366/M763/F1038/T1102/D1127; A203/ G366/D965/F1038/T1102/D1127; A203/G366/M763/D965/ F1038/T1102/D1127; A203/F539/M763/T1102/D1127; A203/F539/D965/T1102/D1127; A203/F539/F1038/T1102/ D1127; A203/F539/M763/D965/T1102/D1127; A203/F539/ M763/F1038/T1102/D1127; A203/F539/D965/F1038/ T1102/D1127; A203/F539/M763/D965/F1038/T1102/ D1127; A203/I601/M763/T1102/D1127; A203/I601/D965/ T1102/D1127; A203/I601/F1038/T1102/D1127; A203/I601/ M763/D965/T1102/D1127; A203/I601/M763/F1038/ T1102/D1127; A203/I601/D965/F1038/T1102/D1127; A203/I601/M763/D965/F1038/T1102/D1127; N277/G366/ M763/T1102/D1127; N277/G366/D965/T1102/D1127; N277/G366/F1038/T1102/D1127; N277/G366/M763/ D965/T1102/D1127; N277/G366/M763/F1038/T1102/ D1127; N277/G366/D965/F1038/T1102/D1127; N277/ G366/M763/D965/F1038/T1102/D1127; N277/F539/ M763/T1102/D1127; N277/F539/D965/T1102/D1127; N277/F539/F1038/T1102/D1127; N277/F539/M763/D965/ T1102/D1127; N277/F539/M763/F1038/T1102/D1127; N277/F539/D965/F1038/T1102/D1127; N277/F539/M763/ D965/F1038/T1102/D1127; N277/I601/M763/T1102/ D1127; N277/I601/D965/T1102/D1127; N277/I601/F1038/ T1102/D1127; N277/I601/M763/D965/T1102/D1127; N277/I601/M763/F1038/T1102/D1127; N277/I601/D965/ F1038/T1102/D1127; N277/I601/M763/D965/F1038/

T1102/D1127; G366/F539/M763/T1102/D1127; G366/F539/D965/T1102/D1127; G366/F539/F1038/T1102/D1127; G366/F539/M763/D965/T1102/D1127; G366/F539/M763/F1038/T1102/D1127; G366/F539/D965/F1038/T1102/D1127; G366/F539/M763/D965/F1038/T1102/D1127; G366/I601/M763/T1102/D1127; G366/I601/D965/T1102/D1127; G366/I601/F1038/T1102/D1127; G366/I601/M763/D965/T1102/D1127; G366/I601/M763/F1038/T1102/D1127; G366/I601/D965/F1038/T1102/D1127; G366/I601/M763/D965/F1038/T1102/D1127; F539/I601/M763/T1102/D1127; F539/I601/D965/T1102/D1127; F539/I601/F1038/T1102/D1127; F539/I601/M763/D965/T1102/D1127; F539/I601/M763/F1038/T1102/D1127; F539/I601/D965/F1038/T1102/D1127; or F539/I601/M763/D965/F1038/T1102/D1127 of the wild-type SpCas9.

In one exemplary embodiment, the TS-SpCas9 may be a SpCas9 variant formed by modifying A203/N277/G366/M763/T1102; A203/N277/G366/D965/T1102; A203/N277/G366/F1038/T1102; A203/N277/G366/M763/D965/T1102; A203/N277/G366/M763/F1038/T1102; A203/N277/G366/D965/F1038/T1102; A203/N277/G366/M763/D965/F1038/T1102; A203/N277/F539/M763/T1102; A203/N277/F539/D965/T1102; A203/N277/F539/F1038/T1102; A203/N277/F539/M763/D965/T1102; A203/N277/F539/M763/F1038/T1102; A203/N277/F539/D965/F1038/T1102; A203/N277/F539/M763/D965/F1038/T1102; A203/N277/I601/M763/T1102; A203/N277/I601/D965/T1102; A203/N277/I601/F1038/T1102; A203/N277/I601/M763/D965/T1102; A203/N277/I601/M763/F1038/T1102; A203/N277/I601/D965/F1038/T1102; A203/N277/I601/M763/D965/F1038/T1102; A203/G366/F539/M763/T1102; A203/G366/F539/D965/T1102; A203/G366/F539/F1038/T1102; A203/G366/F539/M763/D965/T1102; A203/G366/F539/M763/F1038/T1102; A203/G366/F539/D965/F1038/T1102; A203/G366/F539/M763/D965/F1038/T1102; A203/G366/I601/M763/T1102; A203/G366/I601/D965/T1102; A203/G366/I601/F1038/T1102; A203/G366/I601/M763/D965/T1102; A203/G366/I601/M763/F1038/T1102; A203/G366/I601/D965/F1038/T1102; A203/G366/I601/M763/D965/F1038/T1102; A203/F539/I601/M763/T1102; A203/F539/I601/D965/T1102; A203/F539/I601/F1038/T1102; A203/F539/I601/M763/D965/T1102; A203/F539/I601/M763/F1038/T1102; A203/F539/I601/D965/F1038/T1102; N277/G366/F539/M763/T1102; N277/G366/F539/D965/T1102; N277/G366/F539/F1038/T1102; N277/G366/F539/M763/D965/T1102; N277/G366/F539/M763/F1038/T1102; N277/G366/F539/D965/F1038/T1102; N277/G366/F539/M763/D965/F1038/T1102; N277/G366/I601/M763/T1102; N277/G366/I601/D965/T1102; N277/G366/I601/F1038/T1102; N277/G366/I601/M763/D965/T1102; N277/G366/I601/M763/F1038/T1102; N277/G366/I601/D965/F1038/T1102; N277/G366/I601/M763/D965/F1038/T1102; G366/F539/I601/M763/T1102; G366/F539/I601/D965/T1102; G366/F539/I601/F1038/T1102; G366/F539/I601/M763/D965/T1102; G366/F539/I601/M763/F1038/T1102; G366/F539/I601/D965/F1038/T1102; G366/F539/I601/M763/D965/F1038/T1102; A203/N277/G366/M763/D1127; A203/N277/G366/D965/D1127; A203/N277/G366/F1038/D1127; A203/N277/G366/M763/D965/D1127; A203/N277/G366/M763/F1038/D1127; A203/N277/G366/D965/F1038/D1127; A203/N277/G366/M763/D965/F1038/D1127; A203/N277/F539/M763/D1127; A203/N277/F539/D965/D1127; A203/N277/F539/F1038/D1127; A203/N277/F539/M763/D965/D1127; A203/N277/F539/M763/F1038/D1127; A203/N277/F539/D965/F1038/D1127; A203/N277/F539/M763/D965/F1038/D1127;

A203/N277/I601/M763/D1127; A203/N277/I601/D965/D1127; A203/N277/I601/F1038/D1127; A203/N277/I601/M763/F1038/D1127; A203/N277/I601/M763/D965/F1038/D1127; A203/N277/I601/D965/F1038/D1127; A203/N277/I601/M763/D965/F1038/D1127; A203/G366/F539/M763/D1127; A203/G366/F539/D965/D1127; A203/G366/F539/F1038/D1127; A203/G366/F539/M763/D965/D1127; A203/G366/F539/M763/F1038/D1127; A203/G366/F539/D965/F1038/D1127; A203/G366/F539/M763/D965/F1038/D1127; A203/G366/I601/M763/D1127; A203/G366/I601/D965/D1127; A203/G366/I601/F1038/D1127; A203/G366/I601/M763/D965/D1127; A203/G366/I601/M763/F1038/D1127; A203/G366/I601/D965/F1038/D1127; A203/G366/I601/M763/D965/F1038/D1127; A203/F539/I601/M763/D1127; A203/F539/I601/D965/D1127; A203/F539/I601/F1038/D1127; A203/F539/I601/M763/D965/D1127; A203/F539/I601/M763/F1038/D1127; A203/F539/I601/D965/F1038/D1127; A203/F539/I601/M763/D965/F1038/D1127; N277/G366/F539/M763/D1127; N277/G366/F539/D965/D1127; N277/G366/F539/F1038/D1127; N277/G366/F539/M763/D965/D1127; N277/G366/F539/M763/F1038/D1127; N277/G366/F539/D965/F1038/D1127; N277/G366/F539/M763/D965/F1038/D1127; N277/G366/I601/M763/D1127; N277/G366/I601/D965/D1127; N277/G366/I601/F1038/D1127; N277/G366/I601/M763/D965/D1127; N277/G366/I601/M763/F1038/D1127; N277/G366/I601/D965/F1038/D1127; N277/G366/I601/M763/D965/F1038/D1127; G366/F539/I601/M763/D1127; G366/F539/I601/D965/D1127; G366/F539/I601/F1038/D1127; G366/F539/I601/M763/D965/D1127; G366/F539/I601/M763/F1038/D1127; G366/F539/I601/D965/F1038/D1127; or G366/F539/I601/M763/D965/F1038/D1127 of the wild-type SpCas9.

In another exemplary embodiment, the TS-SpCas9 may be a SpCas9 variant formed by modifying A203/N277/G366/M763/T1102/D1127; A203/N277/G366/D965/T1102/D1127; A203/N277/G366/F1038/T1102/D1127; A203/N277/G366/M763/D965/T1102/D1127; A203/N277/G366/M763/F1038/T1102/D1127; A203/N277/G366/D965/F1038/T1102/D1127; A203/N277/G366/M763/D965/F1038/T1102/D1127; A203/N277/F539/M763/T1102/D1127; A203/N277/F539/D965/T1102/D1127; A203/N277/F539/F1038/T1102/D1127; A203/N277/F539/M763/D965/T1102/D1127; A203/N277/F539/M763/F1038/T1102/D1127; A203/N277/F539/D965/F1038/T1102/D1127; A203/N277/F539/M763/D965/F1038/T1102/D1127; A203/N277/I601/M763/T1102/D1127; A203/N277/I601/D965/T1102/D1127; A203/N277/I601/F1038/T1102/D1127; A203/N277/I601/M763/D965/T1102/D1127; A203/N277/I601/M763/F1038/T1102/D1127; A203/N277/I601/D965/F1038/T1102/D1127; A203/N277/I601/M763/D965/F1038/T1102/D1127; A203/G366/F539/M763/T1102/D1127; A203/G366/F539/D965/T1102/D1127; A203/G366/F539/F1038/T1102/D1127; A203/G366/F539/M763/D965/T1102/D1127; A203/G366/F539/M763/F1038/T1102/D1127; A203/G366/F539/D965/F1038/T1102/D1127; A203/G366/F539/M763/D965/F1038/T1102/D1127; A203/G366/I601/M763/T1102/D1127; A203/G366/I601/D965/T1102/D1127; A203/G366/I601/F1038/T1102/D1127; A203/G366/I601/M763/D965/T1102/D1127; A203/G366/I601/M763/F1038/T1102/D1127; A203/G366/I601/D965/F1038/T1102/D1127; A203/G366/I601/M763/D965/F1038/T1102/D1127; A203/F539/I601/M763/T1102/D1127; A203/F539/I601/D965/T1102/D1127; A203/F539/I601/F1038/T1102/D1127; A203/F539/I601/M763/D965/T1102/D1127; A203/F539/I601/M763/F1038/T1102/D1127; A203/F539/I601/D965/F1038/T1102/D1127; A203/F539/

I601/M763/D965/F1038/T1102/D1127; N277/G366/F539/ M763/T1102/D1127; N277/G366/F539/D965/T1102/ D1127; N277/G366/F539/F1038/T1102/D1127; N277/ G366/F539/M763/D965/T1102/D1127; N277/G366/F539/ M763/F1038/T1102/D1127; N277/G366/F539/D965/ F1038/T1102/D1127; N277/G366/F539/M763/D965/ F1038/T1102/D1127; N277/G366/I601/M763/T1102/ D1127; N277/G366/I601/D965/T1102/D1127; N277/G366/ I601/F1038/T1102/D1127; N277/G366/I601/M763/D965/ T1102/D1127; N277/G366/I601/M763/F1038/T1102/ D1127; N277/G366/I601/D965/F1038/T1102/D1127; N277/G366/I601/M763/D965/F1038/T1102/D1127; G366/ F539/I601/M763/T1102/D1127; G366/F539/I601/D965/ T1102/D1127; G366/F539/I601/F1038/T1102/D1127; G366/F539/I601/M763/D965/T1102/D1127; G366/F539/ I601/M763/F1038/T1102/D1127; G366/F539/I601/D965/ F1038/T1102/D1127; or G366/F539/I601/M763/D965/ F1038/T1102/D1127 of the wild-type SpCas9.

In one exemplary embodiment, the TS-SpCas9 may be a SpCas9 variant formed by modifying A203/N277/G366/ F539/M763/T1102; A203/N277/G366/F539/D965/T1102; A203/N277/G366/F539/F1038/T1102; A203/N277/G366/ F539/M763/D965/T1102; A203/N277/G366/F539/M763/ F1038/T1102; A203/N277/G366/F539/D965/F1038/T1102; A203/N277/G366/F539/M763/D965/F1038/T1102; A203/ N277/G366/I601/M763/T1102; A203/N277/G366/I601/ D965/T1102; A203/N277/G366/I601/F1038/T1102; A203/ N277/G366/I601/M763/D965/T1102; A203/N277/G366/ I601/M763/F1038/T1102; A203/N277/G366/I601/D965/ F1038/T1102; A203/N277/G366/I601/M763/D965/F1038/ T1102; N277/G366/F539/I601/M763/T1102; N277/G366/ F539/I601/D965/T1102; N277/G366/F539/I601/F1038/ T1102; N277/G366/F539/I601/M763/D965/T1102; N277/ G366/F539/I601/M763/F1038/T1102; N277/G366/F539/ I601/D965/F1038/T1102; N277/G366/F539/I601/M763/ D965/F1038/T1102; A203/N277/G366/F539/I601/M763/ T1102; A203/N277/G366/F539/I601/D965/T1102; A203/ N277/G366/F539/I601/F1038/T1102; A203/N277/G366/ F539/I601/M763/D965/T1102; A203/N277/G366/F539/ I601/M763/F1038/T1102; A203/N277/G366/F539/I601/ D965/F1038/T1102; A203/N277/G366/F539/I601/M763/ D965/F1038/T1102; A203/N277/G366/F539/M763/D1127; A203/N277/G366/F539/D965/D1127; A203/N277/G366/ F539/F1038/D1127; A203/N277/G366/F539/M763/D965/ D1127; A203/N277/G366/F539/M763/F1038/D1127; A203/N277/G366/F539/D965/F1038/D1127; A203/N277/ G366/F539/M763/D965/F1038/D1127; A203/N277/G366/ I601/M763/D1127; A203/N277/G366/I601/D965/D1127; A203/N277/G366/I601/F1038/D1127; A203/N277/G366/ I601/M763/D965/D1127; A203/N277/G366/I601/M763/ F1038/D1127; A203/N277/G366/I601/D965/F1038/D1127; A203/N277/G366/I601/M763/D965/F1038/D1127; N277/ G366/F539/I601/M763/D1127; N277/G366/F539/I601/ D965/D1127; N277/G366/F539/I601/F1038/D1127; N277/ G366/F539/I601/M763/D965/D1127; N277/G366/F539/ I601/M763/F1038/D1127; N277/G366/F539/I601/D965/ F1038/D1127; N277/G366/F539/I601/M763/D965/F1038/ D1127; A203/N277/G366/F539/I601/M763/D1127; A203/ N277/G366/F539/I601/D965/D1127; A203/N277/G366/ F539/I601/F1038/D1127; A203/N277/G366/F539/I601/ M763/D965/D1127; A203/N277/G366/F539/I601/M763/ F1038/D1127; A203/N277/G366/F539/I601/D965/F1038/ D1127; or A203/N277/G366/F539/I601/M763/D965/ F1038/D1127 of the wild-type SpCas9.

In another exemplary embodiment, the TS-SpCas9 may be a SpCas9 variant formed by modifying A203/N277/ G366/F539/M763/T1102/D1127; A203/N277/G366/F539/

D965/T1102/D1127; A203/N277/G366/F539/F1038/T1102/ D1127; A203/N277/G366/F539/M763/D965/T1102/D1127; A203/N277/G366/F539/M763/F1038/T1102/D1127; A203/ N277/G366/F539/D965/F1038/T1102/D1127; A203/N277/ G366/F539/M763/D965/F1038/T1102/D1127; A203/N277/ G366/I601/M763/T1102/D1127; A203/N277/G366/I601/ D965/T1102/D1127; A203/N277/G366/I601/F1038/T1102/ D1127; A203/N277/G366/I601/M763/D965/T1102/D1127; A203/N277/G366/I601/M763/F1038/T1102/D1127; A203/ N277/G366/I601/D965/F1038/T1102/D1127; A203/N277/ G366/I601/M763/D965/F1038/T1102/D1127; N277/G366/ F539/I601/M763/T1102/D1127; N277/G366/F539/I601/ D965/T1102/D1127; N277/G366/F539/I601/F1038/T1102/ D1127; N277/G366/F539/I601/M763/D965/T1102/D1127; N277/G366/F539/I601/M763/F1038/T1102/D1127; N277/ G366/F539/I601/D965/F1038/T1102/D1127; N277/G366/ F539/I601/M763/D965/F1038/T1102/D1127; A203/N277/ G366/F539/I601/M763/T1102/D1127; A203/N277/G366/ F539/I601/D965/T1102/D1127; A203/N277/G366/F539/ I601/F1038/T1102/D1127; A203/N277/G366/F539/I601/ M763/D965/T1102/D1127; A203/N277/G366/F539/I601/ M763/F1038/T1102/D1127; A203/N277/G366/F539/I601/ D965/F1038/T1102/D1127; or A203/N277/G366/F539/ I601/M763/D965/F1038/T1102/D1127 of the wild-type SpCas9.

The TS-SpCas9 may be a SpCas9 variant formed by modifying three or more amino acids selected from the amino acid sequences of the second region, the third region and the fourth region of the wild-type SpCas9. Here, the three or more amino acids may be present in different regions, respectively.

The TS-SpCas9 may be a SpCas9 variant formed by modifying one or more amino acids selected from the amino acid sequence(s) of the region 2-1, the region 2-2 and/or the region 2-3; one or more amino acids selected from the amino acid sequence of the region 3-1; and one or more amino acids selected from the amino acid sequence of the region 4-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying M763/K890/T1102; K890/D965/T1102; K890/F1038/T1102; M763/K890/ D1127; K890/D965/D1127; K890/F1038/D1127; M763/

K890/T1102/D1127; K890/D965/T1102/D1127; or K890/F1038/T1102/D1127 of the wild-type SpCas9.

In another exemplary embodiment, the TS-SpCas9 may be a SpCas9 variant formed by modifying M763/K890/D965/T1102; M763/K890/F1038/T1102; K890/D965/F1038/T1102; M763/K890/D965/D1127; M763/K890/F1038/D1127; K890/D965/F1038/D1127; M763/K890/D965/T1102/D1127; M763/K890/F1038/T1102/D1127; or K890/D965/F1038/T1102/D1127 of the wild-type SpCas9.

In still another exemplary embodiment, the TS-SpCas9 may be a SpCas9 variant formed by modifying M763/K890/D965/F1038/T1102; M763/K890/D965/F1038/D1127 or M763/K890/D965/F1038/T1102/D1127 of the wild-type SpCas9.

The TS-SpCas9 may be a SpCas9 variant formed by modifying three or more amino acids selected from the amino acid sequences of the first region, the second region, the third region and the fourth region of the wild-type SpCas9. Here, the three or more amino acids may be present in different regions, respectively.

The TS-SpCas9 may be a SpCas9 variant formed by modifying one or more amino acids selected from the amino acid sequence(s) of the region 2-1, the region 2-2 and/or the region 2-3; one or more amino acids selected from the amino acid sequence of the region 3-1; and one or more amino acids selected from the amino acid sequence of the region 4-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; one or more amino acids I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying A203/M763/K890/T1102; A203/K890/D965/T1102; A203/K890/F1038/T1102; A203/M763/K890/D965/T1102; A203/M763/K890/F1038/T1102; A203/K890/D965/F1038/T1102; A203/M763/K890/D965/F1038/T1102; N277/M763/K890/T1102; N277/K890/D965/T1102; N277/K890/F1038/T1102; N277/M763/K890/D965/T1102; N277/M763/K890/F1038/T1102; N277/K890/D965/F1038/T1102; N277/M763//K890D965/F1038/T1102; G366/M763/K890/T1102; G366/K890/D965/T1102; G366/K890/F1038/T1102; G366/M763/K890/D965/T1102; G366/M763/K890/F1038/T1102; G366/K890/D965/F1038/T1102; G366/M763/K890/D965/F1038/T1102; F539/M763/K890/T1102; F539/K890/D965/T1102; F539/K890/F1038/T1102; F539/M763/K890/D965/T1102; F539/M763/K890/F1038/T1102; F539/K890/D965/F1038/T1102; F539/M763/K890/D965/F1038/T1102; I601/M763/K890/T1102; I601/K890/D965/T1102; I601/K890/F1038/T1102; I601/M763/K890/D965/T1102; I601/M763/K890/F1038/T1102; I601/K890/D965/F1038/T1102; I601/M763/K890/D965/F1038/T1102; A203/M763/K890/D1127; A203/K890/D965/D1127; A203/K890/F1038/D1127; A203/M763/K890/D965/D1127; A203/M763/K890/F1038/D1127; A203/K890/D965/F1038/D1127; A203/M763/K890/D965/F1038/D1127; N277/M763/K890/D1127; N277/K890/D965/D1127; N277/K890/F1038/D1127; N277/M763/K890/D965/D1127; N277/M763/K890/F1038/D1127; N277/K890/D965/F1038/D1127; N277/M763//K890D965/F1038/D1127; G366/M763/K890/D1127; G366/K890/D965/D1127; G366/K890/F1038/D1127; G366/M763/K890/D965/D1127; G366/M763/K890/F1038/D1127; G366/K890/D965/F1038/D1127; G366/M763/K890/D965/F1038/D1127; F539/M763/K890/D1127; F539/K890/D965/D1127; F539/K890/F1038/D1127; F539/M763/K890/D965/D1127; F539/M763/K890/F1038/D1127; F539/K890/D965/F1038/D1127; F539/M763/K890/D965/F1038/D1127; I601/M763/K890/D1127; I601/K890/D965/D1127; I601/K890/F1038/D1127; I601/M763/K890/D965/D1127; I601/M763/K890/F1038/D1127; I601/K890/D965/F1038/D1127; or I601/M763/K890/D965/F1038/D1127 of the wild-type SpCas9.

In another exemplary embodiment, the TS-SpCas9 may be a SpCas9 variant formed by modifying A203/M763/K890/T1102/D1127; A203/K890/D965/T1102/D1127; A203/K890/F1038/T1102/D1127; A203/M763/K890/D965/T1102/D1127; A203/M763/K890/F1038/T1102/D1127; A203/K890/D965/F1038/T1102/D1127; A203/M763/K890/D965/F1038/T1102/D1127; N277/M763/K890/T1102/D1127; N277/K890/D965/T1102/D1127; N277/K890/F1038/T1102/D1127; N277/M763/K890/D965/T1102/D1127; N277/M763/K890/F1038/T1102/D1127; N277/K890/D965/F1038/T1102/D1127; N277/M763//K890D965/F1038/T1102/D1127; G366/M763/K890/T1102/D1127; G366/K890/D965/T1102/D1127; G366/K890/F1038/T1102/D1127; G366/M763/K890/D965/T1102/D1127; G366/K890/D965/F1038/T1102/D1127; G366/M763/K890/D965/F1038/T1102/D1127; F539/M763/K890/T1102/D1127; F539/K890/D965/T1102/D1127; F539/K890/F1038/T1102/D1127; F539/M763/K890/D965/T1102/D1127; F539/M763/K890/F1038/T1102/D1127; F539/K890/D965/F1038/T1102/D1127; F539/M763/K890/D965/F1038/T1102/D1127; I601/M763/K890/T1102/D1127; I601/K890/D965/T1102/D1127; I601/K890/F1038/T1102/D1127; I601/M763/K890/D965/T1102/D1127; I601/M763/K890/F1038/T1102/D1127; I601/K890/D965/F1038/

T1102/D1127; or I601/M763/K890/D965/F1038/T1102/ D1127 of the wild-type SpCas9.

In one exemplary embodiment, the TS-SpCas9 may be a SpCas9 variant formed by modifying A203/N277/M763/ K890/T1102; A203/N277/K890/D965/T1102; A203/N277/ K890/F1038/T1102; A203/N277/M763/K890/D965/T1102; A203/N277/M763/K890/F1038/T1102; A203/N277/K890/ D965/F1038/T1102; A203/G366/M763/K890/T1102; A203/G366/K890/ D965/T1102; A203/G366/K890/F1038/T1102; A203/G366/ M763/K890/D965/T1102; A203/G366/M763/K890/F1038/ T1102; A203/G366/K890/D965/F1038/T1102; A203/G366/ M763/K890/D965/F1038/T1102; A203/F539/M763/K890/ T1102; A203/F539/K890/D965/T1102; A203/F539/K890/ F1038/T1102; A203/F539/M763/K890/D965/T1102; A203/ F539/M763/K890/F1038/T1102; A203/F539/K890/D965/ F1038/T1102; A203/F539/M763/K890/D965/F1038/ T1102; A203/I601/M763/K890/T1102; A203/I601/K890/ D965/T1102; A203/I601/K890/F1038/T1102; A203/I601/ M763/K890/D965/T1102; A203/I601/M763/K890/F1038/ T1102; A203/I601/K890/D965/F1038/T1102; A203/I601/ M763/K890/D965/F1038/T1102; N277/G366/M763/K890/ T1102; N277/G366/K890/D965/T1102; N277/G366/K890/ F1038/T1102; N277/G366/M763/K890/D965/T1102; N277/G366/M763/K890/F1038/T1102; N277/G366/K890/ D965/F1038/T1102; N277/G366/M763/K890/D965/F1038/ T1102; N277/F539/M763/K890/T1102; N277/F539/K890/ D965/T1102; N277/F539/K890/F1038/T1102; N277/F539/ M763/K890/D965/T1102; N277/F539/M763/K890/F1038/ T1102; N277/F539/K890/D965/F1038/T1102; N277/F539/ M763/K890/D965/F1038/T1102; N277/I601/M763/K890/ T1102; N277/I601/K890/D965/T1102; N277/I601/K890/ F1038/T1102; N277/I601/M763/K890/D965/T1102; N277/ I601/M763/K890/F1038/T1102; N277/I601/K890/D965/ F1038/T1102; N277/I601/M763/K890/D965/F1038/T1102; G366/F539/M763/K890/T1102; G366/F539/K890/D965/ T1102; G366/F539/K890/F1038/T1102; G366/F539/M763/ K890/D965/T1102; G366/F539/M763/K890/F1038/T1102; G366/F539/K890/D965/F1038/T1102; G366/F539/M763/ K890/D965/F1038/T1102; G366/I601/M763/K890/T1102; G366/I601/K890/D965/T1102; G366/I601/K890/F1038/ T1102; G366/I601/M763/K890/D965/T1102; G366/I601/ M763/K890/F1038/T1102; G366/I601/K890/D965/F1038/ T1102; G366/I601/M763/K890/D965/F1038/T1102; F539/ I601/M763/K890/T1102; F539/I601/K890/D965/T1102; F539/I601/K890/F1038/T1102; F539/I601/M763/K890/ D965/T1102; F539/I601/M763/K890/F1038/T1102; F539/ I601/K890/D965/F1038/T1102; F539/I601/M763/K890/ D965/F1038/T1102; A203/N277/M763/K890/D1127; A203/N277/K890/D965/D1127; A203/N277/K890/F1038/ D1127; A203/N277/M763/K890/D965/D1127; A203/N277/ M763/K890/F1038/D1127; A203/N277/K890/D965/F1038/ D1127; A203/N277/M763/K890/D965/F1038/D1127; A203/G366/M763/K890/D1127; A203/G366/K890/D965/ D1127; A203/G366/K890/F1038/D1127; A203/G366/ M763/K890/D965/D1127; A203/G366/M763/K890/F1038/ D1127; A203/G366/K890/D965/F1038/D1127; A203/ G366/M763/K890/D965/F1038/D1127; A203/F539/M763/ K890/D1127; A203/F539/K890/D965/D1127; A203/F539/ K890/F1038/D1127; A203/F539/M763/K890/D965/D1127; A203/F539/M763/K890/F1038/D1127; A203/F539/K890/ D965/F1038/D1127; A203/F539/M763/K890/D965/F1038/ D1127; A203/I601/M763/K890/D1127; A203/I601/K890/ D965/D1127; A203/I601/K890/F1038/D1127; A203/I601/ M763/K890/D965/D1127; A203/I601/M763/K890/F1038/ D1127; A203/I601/K890/D965/F1038/D1127; A203/I601/ M763/K890/D965/F1038/D1127; N277/G366/M763/K890/

D1127; N277/G366/K890/D965/D1127; N277/G366/K890/ F1038/D1127; N277/G366/M763/K890/D965/D1127; N277/G366/M763/K890/F1038/D1127; N277/G366/K890/ D965/F1038/D1127; N277/G366/M763/K890/D965/F1038/ D1127; N277/F539/M763/K890/D1127; N277/F539/K890/ D965/D1127; N277/F539/K890/F1038/D1127; N277/F539/ M763/K890/D965/D1127; N277/F539/M763/K890/F1038/ D1127; N277/F539/K890/D965/F1038/D1127; N277/F539/ M763/K890/D965/F1038/D1127; N277/I601/M763/K890/ D1127; N277/I601/K890/D965/D1127; N277/I601/K890/ F1038/D1127; N277/I601/M763/K890/D965/D1127; N277/ I601/M763/K890/F1038/D1127; N277/I601/K890/D965/ F1038/D1127; N277/I601/M763/K890/D965/F1038/ D1127; G366/F539/M763/K890/D1127; G366/F539/K890/ D965/D1127; G366/F539/K890/F1038/D1127; G366/F539/ M763/K890/D965/D1127; G366/F539/M763/K890/F1038/ D1127; G366/F539/K890/D965/F1038/D1127; G366/F539/ M763/K890/D965/F1038/D1127; G366/I601/M763/K890/ D1127; G366/I601/K890/D965/D1127; G366/I601/K890/ F1038/D1127; G366/I601/M763/K890/D965/D1127; G366/ I601/M763/K890/F1038/D1127; G366/I601/K890/D965/ F1038/D1127; G366/I601/M763/K890/D965/F1038/ D1127; F539/I601/M763/K890/D1127; F539/I601/K890/ D965/D1127; F539/I601/K890/F1038/D1127; F539/I601/ M763/K890/D965/D1127; F539/I601/M763/K890/F1038/ D1127; F539/I601/K890/D965/F1038/D1127; or F539/ I601/M763/K890/D965/F1038/D1127 of the wild-type SpCas9.

In another exemplary embodiment, the TS-SpCas9 may be a SpCas9 variant formed by modifying A203/N277/ M763/K890/T1102/D1127; A203/N277/K890/D965/T1102/ D1127; A203/N277/K890/F1038/T1102/D1127; A203/ N277/M763/K890/D965/T1102/D1127; A203/N277/M763/ K890/F1038/T1102/D1127; A203/N277/K890/D965/ F1038/T1102/D1127; A203/N277/M763/K890/D965/ F1038/T1102/D1127; A203/G366/M763/K890/T1102/ D1127; A203/G366/K890/D965/T1102/D1127; A203/ G366/K890/F1038/T1102/D1127; A203/G366/M763/K890/ D965/T1102/D1127; A203/G366/M763/K890/F1038/ T1102/D1127; A203/G366/K890/D965/F1038/T1102/ D1127; A203/G366/M763/K890/D965/F1038/T1102/ D1127; A203/F539/M763/K890/T1102/D1127; A203/F539/ K890/D965/T1102/D1127; A203/F539/K890/F1038/T1102/ D1127; A203/F539/M763/K890/D965/T1102/D1127; A203/F539/M763/K890/F1038/T1102/D1127; A203/F539/ K890/D965/F1038/T1102/D1127; A203/F539/M763/K890/ D965/F1038/T1102/D1127; A203/I601/M763/K890/T1102/ D1127; A203/I601/K890/D965/T1102/D1127; A203/I601/ K890/F1038/T1102/D1127; A203/I601/M763/K890/D965/ T1102/D1127; A203/I601/M763/K890/F1038/T1102/ D1127; A203/I601/K890/D965/F1038/T1102/D1127; A203/I601/M763/K890/D965/F1038/T1102/D1127; N277/ G366/M763/K890/T1102/D1127; N277/G366/K890/D965/ T1102/D1127; N277/G366/K890/F1038/T1102/D1127; N277/G366/M763/K890/D965/T1102/D1127; N277/G366/ M763/K890/F1038/T1102/D1127; N277/G366/K890/ D965/F1038/T1102/D1127; N277/G366/M763/K890/ D965/F1038/T1102/D1127; N277/F539/M763/K890/ T1102/D1127; N277/F539/K890/D965/T1102/D1127; N277/F539/K890/F1038/T1102/D1127; N277/F539/M763/ K890/D965/T1102/D1127; N277/F539/M763/K890/F1038/ T1102/D1127; N277/F539/K890/D965/F1038/T1102/ D1127; N277/F539/M763/K890/D965/F1038/T1102/ D1127; N277/I601/M763/K890/T1102/D1127; N277/I601/ K890/D965/T1102/D1127; N277/I601/K890/F1038/T1102/ D1127; N277/I601/M763/K890/D965/T1102/D1127; N277/ I601/M763/K890/F1038/T1102/D1127; N277/I601/K890/

D965/F1038/T1102/D1127; N277/I601/M763/K890/D965/ F1038/T1102/D1127; G366/F539/M763/K890/T1102/ D1127; G366/F539/K890/D965/T1102/D1127; G366/F539/ K890/F1038/T1102/D1127; G366/F539/M763/K890/D965/ T1102/D1127; G366/F539/M763/K890/F1038/T1102/ D1127; G366/F539/K890/D965/F1038/T1102/D1127; G366/F539/M763/K890/D965/F1038/T1102/D1127; G366/ I601/M763/K890/T1102/D1127; G366/I601/K890/D965/ T1102/D1127; G366/I601/K890/F1038/T1102/D1127; G366/I601/M763/K890/D965/T1102/D1127; G366/I601/ M763/K890/F1038/T1102/D1127; G366/I601/K890/D965/ F1038/T1102/D1127; G366/I601/M763/K890/D965/F1038/ T1102/D1127; F539/I601/M763/K890/T1102/D1127; F539/ I601/K890/D965/T1102/D1127; F539/I601/K890/F1038/ T1102/D1127; F539/I601/M763/K890/D965/T1102/D1127; F539/I601/M763/K890/F1038/T1102/D1127; F539/I601/ K890/D965/F1038/T1102/D1127; or F539/I601/M763/ K890/D965/F1038/T1102/D1127 of the wild-type SpCas9.

In one exemplary embodiment, the TS-SpCas9 may be a SpCas9 variant formed by modifying A203/N277/G366/ M763/K890/T1102; A203/N277/G366/K890/D965/T1102; A203/N277/G366/K890/F1038/T1102; A203/N277/G366/ M763/K890/D965/T1102; A203/N277/G366/M763/K890/ F1038/T1102; A203/N277/G366/K890/D965/F1038/ T1102; A203/N277/G366/M763/K890/D965/F1038/T1102; A203/N277/F539/M763/K890/T1102; A203/N277/F539/ K890/D965/T1102; A203/N277/F539/K890/F1038/T1102; A203/N277/F539/M763/K890/D965/T1102; A203/N277/ F539/M763/K890/F1038/T1102; A203/N277/F539/K890/ D965/F1038/T1102; A203/N277/F539/M763/K890/D965/ F1038/T1102; A203/N277/I601/M763/K890/T1102; A203/ N277/I601/K890/D965/T1102; A203/N277/I601/K890/ F1038/T1102; A203/N277/I601/M763/K890/D965/T1102; A203/N277/I601/M763/K890/F1038/T1102; A203/N277/ I601/K890/D965/F1038/T1102; A203/N277/I601/M763/ K890/D965/F1038/T1102; A203/G366/F539/M763/K890/ T1102; A203/G366/F539/K890/D965/T1102; A203/G366/ F539/K890/F1038/T1102; A203/G366/F539/M763/K890/ D965/T1102; A203/G366/F539/M763/K890/F1038/T1102; A203/G366/F539/K890/D965/F1038/T1102; A203/G366/ F539/M763/K890/D965/F1038/T1102; A203/G366/I601/ M763/K890/T1102; A203/G366/I601/K890/D965/T1102; A203/G366/I601/K890/F1038/T1102; A203/G366/I601/ M763/K890/D965/T1102; A203/G366/I601/M763/K890/ F1038/T1102; A203/G366/I601/K890/D965/F1038/T1102; A203/G366/I601/M763/K890/D965/F1038/T1102; A203/ F539/I601/M763/K890/T1102; A203/F539/I601/K890/ D965/T1102; A203/F539/I601/K890/F1038/T1102; A203/ F539/I601/M763/K890/D965/T1102; A203/F539/I601/ M763/K890/F1038/T1102; A203/F539/I601/K890/D965/ F1038/T1102; A203/F539/I601/M763/K890/D965/F1038/ T1102; N277/G366/F539/M763/K890/T1102; N277/G366/ F539/K890/D965/T1102; N277/G366/F539/K890/F1038/ T1102; N277/G366/F539/M763/K890/D965/T1102; N277/ G366/F539/M763/K890/F1038/T1102; N277/G366/F539/ K890/D965/F1038/T1102; N277/G366/F539/M763/K890/ D965/F1038/T1102; N277/G366/I601/M763/K890/T1102; N277/G366/I601/K890/D965/T1102; N277/G366/I601/ K890/F1038/T1102; N277/G366/I601/M763/K890/D965/ T1102; N277/G366/I601/M763/K890/F1038/T1102; N277/ G366/I601/K890/D965/F1038/T1102; N277/G366/I601/ M763/K890/D965/F1038/T1102; G366/F539/I601/M763/ K890/T1102; G366/F539/I601/K890/D965/T1102; G366/ F539/I601/K890/F1038/T1102; G366/F539/I601/M763/ K890/D965/T1102; G366/F539/I601/M763/K890/F1038/ T1102; G366/F539/I601/K890/D965/F1038/T1102; G366/ F539/I601/M763/K890/D965/F1038/T1102; A203/N277/

G366/M763/K890/D1127; A203/N277/G366/K890/D965/ D1127; A203/N277/G366/K890/F1038/D1127; A203/ N277/G366/M763/K890/D965/D1127; A203/N277/G366/ M763/K890/F1038/D1127; A203/N277/G366/K890/D965/ F1038/D1127; A203/N277/G366/M763/K890/D965/F1038/ D1127; A203/N277/F539/M763/K890/D1127; A203/N277/ F539/K890/D965/D1127; A203/N277/F539/K890/F1038/ D1127; A203/N277/F539/M763/K890/D965/D1127; A203/ N277/F539/M763/K890/F1038/D1127; A203/N277/F539/ K890/D965/F1038/D1127; A203/N277/F539/M763/K890/ D965/F1038/D1127; A203/N277/I601/M763/K890/D1127; A203/N277/I601/K890/D965/D1127; A203/N277/I601/ K890/F1038/D1127; A203/N277/I601/M763/K890/D965/ D1127; A203/N277/I601/M763/K890/F1038/D1127; A203/ N277/I601/K890/D965/F1038/D1127; A203/N277/I601/ M763/K890/D965/F1038/D1127; A203/G366/F539/M763/ K890/D1127; A203/G366/F539/K890/D965/D1127; A203/ G366/F539/K890/F1038/D1127; A203/G366/F539/M763/ K890/D965/D1127; A203/G366/F539/M763/K890/F1038/ D1127; A203/G366/F539/K890/D965/F1038/D1127; A203/ G366/F539/M763/K890/D965/F1038/D1127; A203/G366/ I601/M763/K890/D1127; A203/G366/I601/K890/D965/ D1127; A203/G366/I601/K890/F1038/D1127; A203/G366/ I601/M763/K890/D965/D1127; A203/G366/I601/M763/ K890/F1038/D1127; A203/G366/I601/K890/D965/F1038/ D1127; A203/G366/I601/M763/K890/D965/F1038/D1127; A203/F539/I601/M763/K890/D1127; A203/F539/I601/ K890/D965/D1127; A203/F539/I601/K890/F1038/D1127; A203/F539/I601/M763/K890/D965/D1127; A203/F539/ I601/M763/K890/F1038/D1127; A203/F539/I601/K890/ D965/F1038/D1127; A203/F539/I601/M763/K890/D965/ F1038/D1127; N277/G366/F539/M763/K890/D1127; N277/G366/F539/K890/D965/D1127; N277/G366/F539/ K890/F1038/D1127; N277/G366/F539/M763/K890/D965/ D1127; N277/G366/F539/M763/K890/F1038/D1127; N277/G366/F539/K890/D965/F1038/D1127; N277/G366/ F539/M763/K890/D965/F1038/D1127; N277/G366/I601/ M763/K890/D1127; N277/G366/I601/K890/D965/D1127; N277/G366/I601/K890/F1038/D1127; N277/G366/I601/ M763/K890/D965/D1127; N277/G366/I601/M763/K890/ F1038/D1127; N277/G366/I601/K890/D965/F1038/D1127; N277/G366/I601/M763/K890/D965/F1038/D1127; G366/ F539/I601/M763/K890/D1127; G366/F539/I601/K890/ D965/D1127; G366/F539/I601/K890/F1038/D1127; G366/ F539/I601/M763/K890/D965/D1127; G366/F539/I601/ M763/K890/F1038/D1127; G366/F539/I601/K890/D965/ F1038/D1127; or G366/F539/I601/M763/K890/D965/ F1038/D1127 of the wild-type SpCas9.

In another exemplary embodiment, the TS-SpCas9 may be a SpCas9 variant formed by modifying A203/N277/ G366/M763/K890/T1102/D1127; A203/N277/G366/K890/ D965/T1102/D1127; A203/N277/G366/K890/F1038/ T1102/D1127; A203/N277/G366/M763/K890/D965/T1102/ D1127; A203/N277/G366/M763/K890/F1038/T1102/ D1127; A203/N277/G366/K890/D965/F1038/T1102/ D1127; A203/N277/G366/M763/K890/D965/F1038/T1102/ D1127; A203/N277/F539/M763/K890/T1102/D1127; A203/N277/F539/K890/D965/T1102/D1127; A203/N277/ F539/K890/F1038/T1102/D1127; A203/N277/F539/M763/ K890/D965/T1102/D1127; A203/N277/F539/M763/K890/ F1038/T1102/D1127; A203/N277/F539/K890/D965/F1038/ T1102/D1127; A203/N277/F539/M763/K890/D965/F1038/ T1102/D1127; A203/N277/I601/M763/K890/T1102/ D1127; A203/N277/I601/K890/D965/T1102/D1127; A203/ N277/I601/K890/F1038/T1102/D1127; A203/N277/I601/ M763/K890/D965/T1102/D1127; A203/N277/I601/M763/ K890/F1038/T1102/D1127; A203/N277/I601/K890/D965/

F1038/T1102/D1127; A203/N277/I601/M763/K890/D965/ F1038/T1102/D1127; A203/G366/F539/M763/K890/ T1102/D1127; A203/G366/F539/K890/D965/T1102/ D1127; A203/G366/F539/K890/F1038/T1102/D1127; A203/G366/F539/M763/K890/D965/T1102/D1127; A203/ G366/F539/M763/K890/F1038/T1102/D1127; A203/G366/ F539/K890/D965/F1038/T1102/D1127; A203/G366/F539/ M763/K890/D965/F1038/T1102/D1127; A203/G366/I601/ M763/K890/T1102/D1127; A203/G366/I601/K890/D965/ T1102/D1127; A203/G366/I601/K890/F1038/T1102/ D1127; A203/G366/I601/M763/K890/D965/T1102/D1127; A203/G366/I601/M763/K890/F1038/T1102/D1127; A203/ G366/I601/K890/D965/F1038/T1102/D1127; A203/G366/ I601/M763/K890/D965/F1038/T1102/D1127; A203/F539/ I601/M763/K890/T1102/D1127; A203/F539/I601/K890/ D965/T1102/D1127; A203/F539/I601/K890/F1038/T1102/ D1127; A203/F539/I601/M763/K890/D965/T1102/D1127; A203/F539/I601/M763/K890/F1038/T1102/D1127; A203/ F539/I601/K890/D965/F1038/T1102/D1127; A203/F539/ I601/M763/K890/D965/F1038/T1102/D1127; N277/G366/ F539/M763/K890/T1102/D1127; N277/G366/F539/K890/ D965/T1102/D1127; N277/G366/F539/K890/F1038/ T1102/D1127; N277/G366/F539/M763/K890/D965/T1102/ D1127; N277/G366/F539/M763/K890/F1038/T1102/ D1127; N277/G366/F539/K890/D965/F1038/T1102/ D1127; N277/G366/F539/M763/K890/D965/F1038/T1102/ D1127; N277/G366/I601/M763/K890/T1102/D1127; N277/ G366/I601/K890/D965/T1102/D1127; N277/G366/I601/ K890/F1038/T1102/D1127; N277/G366/I601/M763/K890/ D965/T1102/D1127; N277/G366/I601/M763/K890/F1038/ T1102/D1127; N277/G366/I601/K890/D965/F1038/T1102/ D1127; N277/G366/I601/M763/K890/D965/F1038/T1102/ D1127; G366/F539/I601/M763/K890/T1102/D1127; G366/ F539/I601/K890/D965/T1102/D1127; G366/F539/I601/ K890/F1038/T1102/D1127; G366/F539/I601/M763/K890/ D965/T1102/D1127; G366/F539/I601/M763/K890/F1038/ T1102/D1127; G366/F539/I601/K890/D965/F1038/T1102/ D1127; or G366/F539/I601/M763/K890/D965/F1038/ T1102/D1127 of the wild-type SpCas9.

In one exemplary embodiment, the TS-SpCas9 may be a SpCas9 variant formed by modifying A203/N277/G366/ F539/M763/K890/T1102; A203/N277/G366/F539/K890/ D965/T1102; A203/N277/G366/F539/K890/F1038/T1102; A203/N277/G366/F539/M763/K890/D965/T1102; A203/ N277/G366/F539/M763/K890/F1038/T1102; A203/N277/ G366/F539/K890/D965/F1038/T1102; A203/N277/G366/ F539/M763/K890/D965/F1038/T1102; A203/N277/G366/ I601/M763/K890/T1102; A203/N277/G366/I601/K890/ D965/T1102; A203/N277/G366/I601/K890/F1038/T1102; A203/N277/G366/I601/M763/K890/D965/T1102; A203/ N277/G366/I601/M763/K890/F1038/T1102; A203/N277/ G366/I601/K890/D965/F1038/T1102; A203/N277/G366/ I601/M763/K890/D965/F1038/T1102; N277/G366/F539/ I601/M763/K890/T1102; N277/G366/F539/I601/K890/ D965/T1102; N277/G366/F539/I601/K890/F1038/T1102; N277/G366/F539/I601/M763/K890/D965/T1102; N277/ G366/F539/I601/M763/K890/F1038/T1102; N277/G366/ F539/I601/K890/D965/F1038/T1102; N277/G366/F539/ I601/M763/K890/D965/F1038/T1102; A203/N277/G366/ F539/I601/M763/K890/T1102; A203/N277/G366/F539/ I601/K890/D965/T1102; A203/N277/G366/F539/I601/ K890/F1038/T1102; A203/N277/G366/F539/I601/M763/ K890/D965/T1102; A203/N277/G366/F539/I601/M763/ K890/F1038/T1102; A203/N277/G366/F539/I601/K890/ D965/F1038/T1102; A203/N277/G366/F539/I601/M763/ K890/D965/F1038/T1102; A203/N277/G366/F539/M763/ K890/D1127; A203/N277/G366/F539/K890/D965/D1127;

A203/N277/G366/F539/K890/F1038/D1127; A203/N277/ G366/F539/M763/K890/D965/D1127; A203/N277/G366/ F539/M763/K890/F1038/D1127; A203/N277/G366/F539/ K890/D965/F1038/D1127; A203/N277/G366/F539/M763/ K890/D965/F1038/D1127; A203/N277/G366/I601/M763/ K890/D1127; A203/N277/G366/I601/K890/D965/D1127; A203/N277/G366/I601/K890/F1038/D1127; A203/N277/ G366/I601/M763/K890/D965/D1127; A203/N277/G366/ I601/M763/K890/F1038/D1127; A203/N277/G366/I601/ K890/D965/F1038/D1127; A203/N277/G366/I601/M763/ K890/D965/F1038/D1127; N277/G366/F539/I601/M763/ K890/D1127; N277/G366/F539/I601/K890/D965/D1127; N277/G366/F539/I601/K890/F1038/D1127; N277/G366/ F539/I601/M763/K890/D965/D1127; N277/G366/F539/ I601/M763/K890/F1038/D1127; N277/G366/F539/I601/ K890/D965/F1038/D1127; N277/G366/F539/I601/M763/ K890/D965/F1038/D1127; A203/N277/G366/F539/I601/ M763/K890/D1127; A203/N277/G366/F539/I601/K890/ D965/D1127; A203/N277/G366/F539/I601/K890/F1038/ D1127; A203/N277/G366/F539/I601/M763/K890/D965/ D1127; A203/N277/G366/F539/I601/M763/K890/F1038/ D1127; A203/N277/G366/F539/I601/K890/D965/F1038/ D1127; or A203/N277/G366/F539/I601/M763/K890/D965/ F1038/D1127 of the wild-type SpCas9.

In another exemplary embodiment, the TS-SpCas9 may be a SpCas9 variant formed by modifying A203/N277/ G366/F539/M763/K890/T1102/D1127; A203/N277/G366/ F539/K890/D965/T1102/D1127; A203/N277/G366/F539/ K890/F1038/T1102/D1127; A203/N277/G366/F539/M763/ K890/D965/T1102/D1127; A203/N277/G366/F539/M763/ K890/F1038/T1102/D1127; A203/N277/G366/F539/K890/ D965/F1038/T1102/D1127; A203/N277/G366/F539/M763/ K890/D965/F1038/T1102/D1127; A203/N277/G366/I601/ M763/K890/T1102/D1127; A203/N277/G366/I601/K890/ D965/T1102/D1127; A203/N277/G366/I601/K890/F1038/ T1102/D1127; A203/N277/G366/I601/M763/K890/D965/ T1102/D1127; A203/N277/G366/I601/M763/K890/F1038/ T1102/D1127; A203/N277/G366/I601/K890/D965/F1038/ T1102/D1127; A203/N277/G366/I601/M763/K890/D965/ F1038/T1102/D1127; N277/G366/F539/I601/M763/K890/ T1102/D1127; N277/G366/F539/I601/K890/D965/T1102/ D1127; N277/G366/F539/I601/K890/F1038/T1102/D1127; N277/G366/F539/I601/M763/K890/D965/T1102/D1127; N277/G366/F539/I601/M763/K890/F1038/T1102/D1127; N277/G366/F539/I601/K890/D965/F1038/T1102/D1127; N277/G366/F539/I601/M763/K890/D965/F1038/T1102/ D1127; A203/N277/G366/F539/I601/M763/K890/T1102/ D1127; A203/N277/G366/F539/I601/K890/D965/T1102/ D1127; A203/N277/G366/F539/I601/K890/F1038/T1102/ D1127; A203/N277/G366/F539/I601/M763/K890/D965/ T1102/D1127; A203/N277/G366/F539/I601/M763/K890/ F1038/T1102/D1127; A203/N277/G366/F539/I601/K890/ D965/F1038/T1102/D1127; or A203/N277/G366/F539/ I601/M763/K890/D965/F1038/T1102/D1127 of the wild-type SpCas9.

The TS-SpCas9 may be a SpCas9 variant formed by removing one or more amino acids selected from the amino acid sequence(s) of the first region, the second region, the third region and/or the fourth region of the wild-type SpCas9.

The TS-SpCas9 may be a SpCas9 variant formed by removing one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the first region; I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the second region; K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the third region; and/or T1102, S1106, E1108, S1116, D1117, D1125, D1127, D1135, S1136 and T1138 in the fourth region of the wild-type SpCas9.

The TS-SpCas9 may be a SpCas9 variant formed by substituting one or more amino acids selected from the amino acid sequence(s) of the first region, the second region, the third region and/or the fourth region of the wild-type SpCas9 with different amino acid(s).

The TS-SpCas9 may be a SpCas9 variant formed by substituting one or more amino acids selected from the amino acid sequence of the first region of the wild-type SpCas9 with different amino acid(s).

The TS-SpCas9 may be a SpCas9 variant formed by substituting one or more amino acids selected from N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively low hydropathy index.

In one exemplary embodiment, the TS-SpCas9 may be a SpCas9 variant formed by substituting A203 (hydropathy index: 1.8) in the region 1-1 of the wild-type SpCas9 with one amino acid selected from the group consisting of amino acids having a relatively low hydropathy index, such as arginine, asparagine, aspartic acid, glutamic acid, glutamine, glycine, histidine, lysine, proline, serine, threonine, tryptophan and tyrosine.

For example, the TS-SpCas9 may be a SpCas9 variant formed by substituting A203 (hydropathy index: 1.8) in the region 1-1 of the wild-type SpCas9 with an amino acid having a relatively low hydropathy index, such as aspartic acid (hydropathy index: −3.5).

In another exemplary embodiment, the TS-SpCas9 may be a SpCas9 variant formed by substituting G366 (hydropathy index: −0.4) in the region 1-2 of the wild-type SpCas9 with one amino acid selected from the group consisting of amino acids having a relatively low hydropathy index, such as arginine, asparagine, aspartic acid, glutamic acid, glutamine, histidine, lysine, proline, serine, threonine, tryptophan and tyrosine.

For example, the TS-SpCas9 may be a SpCas9 variant formed by substituting G366 (hydropathy index: −0.4) in the region 1-2 of the wild-type SpCas9 with an amino acid having a relatively low hydropathy index, such as serine (hydropathy index: −0.8).

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of amino acids having a relatively low hydropathy index, such as alanine, arginine, asparagine, aspartic acid, cysteine, glutamic acid, glutamine, glycine, histidine, lysine, methionine, proline, serine, threonine, tryptophan and tyrosine.

For example, the TS-SpCas9 may be a SpCas9 variant formed by substituting F539 (hydropathy index: 2.8) in the region 1-3 of the wild-type SpCas9 with an amino acid having a relatively low hydropathy index such as serine (hydropathy index: −0.8).

In another exemplary embodiment, the TS-SpCas9 may be a SpCas9 variant formed by substituting I601 (hydropathy index: 4.5) in the region 1-3 of the wild-type SpCas9 with one amino acid selected from the group consisting of amino acids having a relatively low hydropathy index, such as alanine, arginine, asparagine, aspartic acid, cysteine, glutamic acid, glutamine, glycine, histidine, leucine, lysine, methionine, phenylalanine, proline, serine, threonine, tryptophan, tyrosine and valine.

For example, the TS-SpCas9 may be a SpCas9 variant formed by substituting I601 (hydropathy index: 4.5) in the region 1-3 of the wild-type SpCas9 with an amino acid having a relatively low hydropathy index such as asparagine (hydropathy index: −3.5).

In still another exemplary embodiment, the TS-SpCas9 may be a SpCas9 variant formed by substituting A203 (hydropathy index: 1.8), G366 (hydropathy index: −0.4), F539 (hydropathy index: 2.8) and I601 (hydropathy index: 4.5) in the region 1-1, the region 1-2, the region 1-3 and/or the region 1-4 of the wild-type SpCas9 with amino acids having a relatively low hydropathy index, respectively.

For example, the TS-SpCas9 may be a SpCas9 variant formed by substituting A203 (hydropathy index: 1.8) in the region 1-1 of the wild-type SpCas9 with an amino acid having a relatively low hydropathy index, such as aspartic acid (hydropathy index: −3.5), substituting G366 (hydropathy index: −0.4) in the region 1-2 thereof with an amino acid having a relatively low hydropathy index, such as serine (hydropathy index: −0.8), substituting F539 (hydropathy index: 2.8) in the region 1-3 thereof with an amino acid having a relatively low hydropathy index, such as serine (hydropathy index: −0.8), and substituting I601 (hydropathy index: 4.5) in the region 1-3 thereof with an amino acid having a relatively low hydropathy index, such as asparagine (hydropathy index: −3.5).

The TS-SpCas9 may be a SpCas9 variant formed by substituting one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively high hydropathy index.

In one exemplary embodiment, the TS-SpCas9 may be a SpCas9 variant formed by substituting N277 (hydropathy index: −3.5) in the region 1-1 of the wild-type SpCas9 with one amino acid selected from the group consisting of amino acids having a relatively high hydropathy index, such as alanine, cysteine, glycine, histidine, isoleucine, leucine, methionine, phenylalanine, proline, serine, threonine, tryptophan, tyrosine and valine.

For example, the TS-SpCas9 may be a SpCas9 variant formed by substituting N277 (hydropathy index: −3.5) in the region 1-1 of the wild-type SpCas9 with an amino acid having a relatively high hydropathy index, such as histidine (hydropathy index: −3.2).

The TS-SpCas9 may be a SpCas9 variant formed by substituting two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acids having a relatively low or high hydropathy index.

In one exemplary embodiment, the TS-SpCas9 may be a SpCas9 variant formed by substituting A203 (hydropathy index: 1.8), N277 (hydropathy index: −3.5), G366 (hydropathy index: −0.4), F539 (hydropathy index: 2.8) and I601 (hydropathy index: 4.5) in the region 1-1, the region 1-2, the region 1-3 and/or the region 1-4 of the wild-type SpCas9 with amino acids having a relatively low or high hydropathy index, respectively.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, substituting N277 (hydropathy index: −3.5) in the region 1-1 of the wild-type SpCas9 with histidine (hydropathy index: −3.2), which is an amino acid having a relatively high hydropathy index, substituting G366 (hydropathy index: −0.4) in the region 1-2 with serine (hydropathy index: −0.8), which is an amino acid having a relatively low hydropathy index, substituting F539 (hydropathy index: 2.8) in the region 1-3 with serine (hydropathy index: −0.8), which is an amino acid having a relatively low hydropathy index, and substituting I601 (hydropathy index: 4.5) in the region 1-3 with asparagine (hydropathy index: −3.5), which is an amino acid having a relatively low hydropathy index.

The TS-SpCas9 may be a SpCas9 variant formed by substituting one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively small functional group.

In one exemplary embodiment, the TS-SpCas9 may be a SpCas9 variant formed by substituting F539 in the region 1-3 of the wild-type SpCas9 with one amino acid selected from the group consisting of alanine, asparagine, aspartic acid, cysteine, glutamic acid, glutamine, glycine, histidine, isoleucine, leucine, lysine, methionine, proline, serine, threonine and valine, which are amino acids having a relatively small functional group.

For example, the TS-SpCas9 may be a SpCas9 variant formed by substituting F539 in the region 1-3 of the wild-type SpCas9 with asparagine, which is an amino acid having a relatively small functional group.

The TS-SpCas9 may be a SpCas9 variant formed by substituting one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively large functional group.

In one exemplary embodiment, the TS-SpCas9 may be a SpCas9 variant formed by substituting A203 in the region 1-1 of the wild-type SpCas9 with one amino acid selected from the group consisting of arginine, asparagine, aspartic acid, cysteine, glutamic acid, glutamine, histidine, isoleucine, leucine, lysine, methionine, phenylalanine, proline, serine, threonine, tryptophan, tyrosine and valine, which are amino acids having a relatively large functional group.

For example, the TS-SpCas9 may be a SpCas9 variant formed by substituting A203 in the region 1-1 of the wild-type SpCas9 with aspartic acid, which is an amino acid having a relatively large functional group.

The TS-SpCas9 may be a SpCas9 variant formed by substituting two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively small or large functional group.

In one exemplary embodiment, the TS-SpCas9 may be a SpCas9 variant formed by substituting A203, N277, G366, F539 and I601 in the region 1-1, the region 1-2, the region 1-3 and/or the region 1-4 of the wild-type SpCas9 with amino acids having a relatively small or large functional group.

For example, the TS-SpCas9 may be a SpCas9 variant formed by substituting A203 and N277 in the region 1-1, G366 in the region 1-2, and I601 in the region 1-3 of the wild-type SpCas9 with aspartic acid, histidine, serine and asparagine, which are amino acids having a relatively large functional group, respectively, and substituting F539 in the region 1-3 with serine, which has a relatively small functional group.

The TS-SpCas9 may be a SpCas9 variant formed by substituting one or more amino acids selected from the amino acid sequence of the second region of the wild-type SpCas9 with different amino acid(s).

The TS-SpCas9 may be a SpCas9 variant formed by substituting one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3 of the wild-type SpCas9 with amino acid(s) having a relatively high hydropathy index.

In one exemplary embodiment, the TS-SpCas9 may be a SpCas9 variant formed by substituting M763 (hydropathy index: 1.9) in the region 2-2 of the wild-type SpCas9 with one amino acid selected from the group consisting of cysteine, isoleucine, leucine, phenylalanine and valine, which are amino acids having a relatively high hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index.

In another exemplary embodiment, the TS-SpCas9 may be a SpCas9 variant formed by substituting D965 (hydropathy index: −3.5) in the region 2-3 of the wild-type SpCas9 with one amino acid selected from the group consisting of alanine, cysteine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting D965 (hydropathy index: −3.5) in the 2-3 of the wild-type SpCas9 with tyrosine (hydropathy index: −1.3), which is an amino acid having a relatively high hydropathy index.

In still another exemplary embodiment, the TS-SpCas9 may be a SpCas9 variant formed by substituting M763 (hydropathy index: 1.9) and D965 (hydropathy index: −3.5) in the region 2-1, the region 2-2 and/or the region 2-3 of the wild-type SpCas9 with amino acid(s) having a relatively high hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, and substituting D965 (hydropathy index: −3.5) in the region 2-3 of the wild-type SpCas9 with tyrosine (hydropathy index: −1.3), which is an amino acid having a relatively high hydropathy index.

The TS-SpCas9 may be a SpCas9 variant formed by substituting one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3 of the wild-type SpCas9 with amino acids having a relatively low hydropathy index.

In one exemplary embodiment, the TS-SpCas9 may be a SpCas9 variant formed by substituting F1037 and/or F1038 in the region 2-3 of the wild-type SpCas9 with one amino acid selected from the group consisting of arginine, asparagine, aspartic acid, cysteine, glutamic acid, glutamine, glycine, histidine, lysine, methionine, proline, serine, threonine, tryptophan and tyrosine, which are amino acids having a relatively low hydropathy index.

For example, the TS-SpCas9 may be a SpCas9 variant formed by substituting F1038 (hydropathy index: 2.8) in the region 2-3 of the wild-type SpCas9 with tyrosine (hydropathy index: −1.3), which is an amino acid having a relatively low hydropathy index.

For example, the TS-SpCas9 may be a SpCas9 variant formed by substituting F1037 (hydropathy index: 2.8) in the region 2-3 of the wild-type SpCas9 with arginine (hydropathy index: −4.5), which is an amino acid having a relatively low hydropathy index.

The TS-SpCas9 may be a SpCas9 variant formed by substituting two or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3 of the wild-type SpCas9 with amino acid(s) having a relatively low or high hydropathy index.

In one exemplary embodiment, the TS-SpCas9 may be a SpCas9 variant formed by substituting M763 (hydropathy index: 1.9), D965 (hydropathy index: −3.5) and F1038 (hydropathy index: 2.8) in the region 2-1, the region 2-2 and/or the region 2-3 of the wild-type SpCas9 with amino acids having a relatively low or high hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, substituting D965 (hydropathy index: −3.5) in the region 2-3 with tyrosine (hydropathy index: −1.3), which is an amino acid having a relatively high hydropathy index, and substituting F1038 (hydropathy index: 2.8) in the region 2-3 with tyrosine (hydropathy index: −1.3), which is an amino acid having a relatively low hydropathy index.

The TS-SpCas9 may be a SpCas9 variant formed by substituting one or more amino acids selected from the amino acid sequence of the third region of the wild-type SpCas9 with a different amino acid.

The TS-SpCas9 may be a SpCas9 variant formed by substituting one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9 with amino acid(s) having a relatively high hydropathy index.

In one exemplary embodiment, the TS-SpCas9 may be a SpCas9 variant formed by substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting K890 (hydropathy index: −3.9) in the region 3-1 of the wild-type SpCas9 with asparagine (hydropathy index: −3.5), which is an amino acid having a relatively high hydropathy index.

The TS-SpCas9 may be a SpCas9 variant formed by substituting one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9 with uncharged amino acid(s).

In one exemplary embodiment, the TS-SpCas9 may be a SpCas9 variant formed by substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting K890 in the region 3-1 of the wild-type SpCas9 with glutamine, which is an uncharged amino acid.

For example, the TS-SpCas9 may be a SpCas9 variant formed by substituting K890 in the region 3-1 of the wild-type SpCas9 with asparagine, which is an uncharged amino acid.

The TS-SpCas9 may be a SpCas9 variant formed by substituting one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9 with amino acid(s) having a relatively small functional group.

In one exemplary embodiment, the TS-SpCas9 may be a SpCas9 variant formed by substituting K890 and/or K896 in the region 3-1 of the wild-type SpCas9 with one amino acid selected from the group consisting of alanine, asparagine, aspartic acid, cysteine, glycine, isoleucine, leucine, proline, serine, threonine and valine, which are amino acids having a relatively small functional group.

For example, the TS-SpCas9 may be a SpCas9 variant formed by substituting K890 in the region 3-1 of the wild-type SpCas9 with aspartic acid, which is an amino acid having a relatively small functional group.

For example, the TS-SpCas9 may be a SpCas9 variant formed by substituting K896 in the region 3-1 of the wild-type SpCas9 with asparagine, which is an amino acid having a relatively small functional group.

The TS-SpCas9 may be a SpCas9 variant formed by substituting one or more amino acids selected from the amino acid sequence in the fourth region of the wild-type SpCas9 with different amino acids.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with amino acid(s) having a relatively low hydropathy index.

In one exemplary embodiment, the TS-SpCas9 may be a SpCas9 variant formed by substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting T1102 (hydropathy index: −0.7) in the region 4-1 of the wild-type SpCas9 with proline (hydropathy index: −1.6) having a relatively low hydropathy index.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with amino acid(s) having a relatively high hydropathy index.

In one exemplary embodiment, the TS-SpCas9 may be a SpCas9 variant formed by substituting S1106 in the region 4-1 of the wild-type SpCas9 with one amino acid selected from the group consisting of alanine, cysteine, glycine, isoleucine, leucine, methionine, phenylalanine, threonine and valine, which are amino acids having a relatively high hydropathy index.

For example, the TS-SpCas9 may be a SpCas9 variant formed by substituting S1106 (hydropathy index: −0.8) in the region 4-1 of the wild-type SpCas9 with glycine (hydropathy index: −0.4), which is a relatively high hydropathy index.

The TS-SpCas9 may be a SpCas9 variant formed by substituting two or more amino acids selected from the group consisting of T1102, S1106, E1108, S1116, D1117, D1125, D1127, D1135, S1136 and T1138 in the region 4-1 of the wild-type SpCas9 with amino acids having a relatively low or high hydropathy index.

For example, the TS-SpCas9 may be a SpCas9 variant formed by substituting T1102 and S1136 in the region 4-1 of the wild-type SpCas9 with amino acids having a relatively low or high hydropathy index.

For example, the TS-SpCas9 may be a SpCas9 variant formed by substituting T1102 (hydropathy index: −0.7) in the region 4-1 of the wild-type SpCas9 with proline (hydropathy index: −1.6), which has a relatively low hydropathy index, and substituting S1106 (hydropathy index: −0.8) of the wild-type SpCas9 with glycine (hydropathy index: −0.4) having a relatively high hydropathy index.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with amino acid(s) having a relatively small functional group.

In one exemplary embodiment, the TS-SpCas9 may be a SpCas9 variant formed by substituting T1102 in the region 4-1 of the wild-type SpCas9 with an amino acid having a relatively small functional group.

For example, the TS-SpCas9 may be a SpCas9 variant formed by substituting T1102 in the region 4-1 of the wild-type SpCas9 with proline having a relatively small functional group.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with an amino acid having a relatively large functional group.

In one exemplary embodiment, the TS-SpCas9 may be a SpCas9 variant formed by substituting D1127 in the region 4-1 of the wild-type SpCas9 with an amino acid having a relatively large functional group.

For example, the TS-SpCas9 may be a SpCas9 variant formed by substituting D1127 in the region 4-1 of the wild-type SpCas9 with glutamic acid having a relatively large functional group.

The TS-SpCas9 may be a SpCas9 variant formed by substituting two or more amino acids selected from the group consisting of T1102, S1106, E1108, S1116, D1117, D1125, D1127, D1135, S1136 and T1138 in the region 4-1 of the wild-type SpCas9 with amino acids having a relatively small or large functional group.

In one exemplary embodiment, the TS-SpCas9 may be a SpCas9 variant formed by substituting T1102 and D1127 in the region 4-1 of the wild-type SpCas9 with amino acids having a relatively small or large functional group.

For example, the TS-SpCas9 may be a SpCas9 variant formed by substituting T1102 in the region 4-1 of the wild-type SpCas9 with proline having a relatively small functional group, and substituting D1127 in the region 4-1 of the wild-type SpCas9 with glutamic acid having a relatively large functional group.

The TS-SpCas9 may be a SpCas9 variant formed by substituting two or more amino acids selected from the amino acid sequences of the first region, the second region, the third region and/or the fourth region of the wild-type SpCas9 with different amino acids. Here, the two or more amino acids may be present in different regions, respectively.

Here, descriptions on the substitution of the one or more amino acids selected in the different regions are the same as described above.

The TS-SpCas9 may be a SpCas9 variant formed by substituting one or more amino acids selected from the amino acid sequence of the first region; and one or more amino acids selected from the amino acid sequence of the second region of the wild-type SpCas9 with different amino acids, respectively.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; and substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, and substituting M763 (hydropathy index: 1.9) in the region 2-2 of the wild-type SpCas9 with isoleucine (hydropathy index: 4.5) having an amino acid having a relatively high hydropathy index.

In another exemplary embodiment, the TS-SpCas9 may be a SpCas9 variant formed by substituting I601 (hydropathy index: 4.5) in the region 1-3 of the wild-type SpCas9 with one amino acid selected from the group consisting of alanine, arginine, asparagine, aspartic acid, cysteine, glutamic acid, glutamine, glycine, histidine, leucine, lysine, methionine, phenylalanine, proline, serine, threonine, tryptophan, tyrosine and valine, which are amino acids having a relatively low hydropathy index; and substituting D965 (hydropathy index: −3.5) in the region 2-3 of the wild-type SpCas9 with one amino acid selected from the group consisting of alanine, cysteine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting I601 (hydropathy index: 4.5) in the region 1-3 of the wild-type SpCas9 with asparagine (hydropathy index: −3.5), which is an amino acid having a relatively low hydropathy index, and substituting D965 (hydropathy index: −3.5) in the region 2-3 of the wild-type SpCas9 with tyrosine (hydropathy index: −1.3), which is an amino acid having a relatively high hydropathy index.

In still another exemplary embodiment, the TS-SpCas9 may be a SpCas9 variant formed by substituting A203 (hydropathy index: 1.8) in the region 1-1 of the wild-type SpCas9 with one amino acid selected from the group consisting of arginine, asparagine, aspartic acid, glutamic acid, glutamine, glycine, histidine, lysine, proline, serine, threonine, tryptophan and tyrosine, which are amino acids having a relatively low hydropathy index; and substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, and M763 (hydropathy index: 1.9) in the region 2-2 of the wild-type SpCas9 with isoleucine (hydropathy index: 4.5), which is an amino acid having a relatively high hydropathy index.

The TS-SpCas9 may be a SpCas9 variant formed by substituting one or more amino acids selected form the amino acid sequence of the first region of the wild-type SpCas9; and one or more amino acids selected form the amino acid sequence of the third region of the wild-type SpCas9 with different amino acids, respectively.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, and substituting K890 in the region 3-1 of the wild-type SpCas9 with asparagine, which is an uncharged amino acid.

In another exemplary embodiment, the TS-SpCas9 may be a SpCas9 variant formed by substituting F539 and/or I601 in the region 1-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting F539 and I601 in the region 1-3 of the wild-type SpCas9 with threonine and glutamic acid, which are polar amino acids, respectively, and substituting K890 (hydropathy index: −3.9) in the region 3-1 of the wild-type SpCas9 with asparagine (hydropathy index: −3.5), which is an amino acid having a relatively high hydropathy index.

The TS-SpCas9 may be a SpCas9 variant formed by substituting one or more amino acids selected from the amino acid sequence in the first region of the wild-type SpCas9 and one or more amino acids selected from the amino acid sequence in the fourth region of the wild-type SpCas9 with different amino acids, respectively.

In one exemplary embodiment, the TS-SpCas9 may be a SpCas9 variant formed by substituting A203 (hydropathy index: 1.8) in the region 1-1 of the wild-type SpCas9 with one amino acid selected from the group consisting of arginine, asparagine, aspartic acid, glutamic acid, glutamine, glycine, histidine, lysine, proline, serine, threonine, tryptophan and tyrosine, which are amino acids having a relatively low hydropathy index; and substituting T1102 in the region 4-1 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, and substituting T1102 (hydropathy index: −0.7) in the region 4-1 of the wild-type SpCas9 with proline (hydropathy index: −1.6) having a relatively low hydropathy index.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; and substituting D1127 in the region 4-1 of the wild-type SpCas9 with an amino acid having a relatively large functional group.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, and substituting D1127 in the region 4-1 of the wild-type SpCas9 with glutamic acid having a relatively large functional group.

The TS-SpCas9 may be a SpCas9 variant formed by substituting one or more amino acids selected from the amino acid sequence in the second region of the wild-type SpCas9; and one or more amino acids selected from the amino acid sequence in the third region of the wild-type SpCas9 with different amino acids, respectively.

In one exemplary embodiment, the TS-SpCas9 may be a SpCas9 variant formed by substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, and substituting K890 in the region 3-1 of the wild-type SpCas9 with asparagine, which is an uncharged amino acid.

In another exemplary embodiment, the TS-SpCas9 may be a SpCas9 variant formed by substituting F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting K890 (hydropathy index: −3.9) in the region 3-1 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting F1038 in the region 2-3 of the wild-type SpCas9 with tyrosine, which is a polar amino acid, and substituting K890 (hydropathy index: −3.9) in the region 3-1 of the wild-type SpCas9 with asparagine (hydropathy index: −3.5), which is an amino acid having a high hydropathy index.

In another exemplary embodiment, the TS-SpCas9 may be a SpCas9 variant formed by substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which is an amino acid having a relatively high hydropathy index; substituting F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, substituting F1038 in the region 2-3 with tyrosine, which is a polar amino acid, and substituting K890 in the region 3-1 of the wild-type SpCas9 with asparagine, which is an uncharged amino acid.

The TS-SpCas9 may be a SpCas9 variant formed by substituting one or more amino acids selected from the amino acid sequence of the second region of the wild-type SpCas9; and one or more amino acids selected from the amino acid sequence of the fourth region of the wild-type SpCas9 with different amino acids, respectively.

In one exemplary embodiment, the TS-SpCas9 may be a SpCas9 variant formed by substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, and substituting T1102 (hydropathy index: −0.7) in the region 4-1 of the wild-type SpCas9 with proline (hydropathy index: −1.6) having a relatively low hydropathy index.

In another exemplary embodiment, the TS-SpCas9 may be a SpCas9 variant formed by substituting F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting D1127 in the region 4-1 of the wild-type SpCas9 with an amino acid having a relatively large functional group.

For example, the TS-SpCas9 may be a SpCas9 variant formed by substituting F1038 in the region 2-3 of the wild-type SpCas9 with tyrosine, which is a polar amino acid, and substituting D1127 in the region 4-1 of the wild-type SpCas9 with glutamic acid having a relatively large functional group.

The TS-SpCas9 may be a SpCas9 variant formed by substituting one or more amino acids selected from the amino acid sequence of the third region of the wild-type SpCas9; and one or more amino acids selected from the amino acid sequence of the fourth region with different amino acids, respectively.

In one exemplary embodiment, the TS-SpCas9 may be a SpCas9 variant formed by substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting K890 in the region 3-1 of the wild-type SpCas9 with asparagine, which is an uncharged amino acid, and substituting T1102 (hydropathy index: −0.7) in the region 4-1 of the wild-type SpCas9 with proline (hydropathy index: −1.6) having a relatively low hydropathy index.

In another exemplary embodiment, the TS-SpCas9 may be a SpCas9 variant formed by substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index; and substituting D1127 in the region 4-1 of the wild-type SpCas9 with an amino acid having a relatively large functional group.

For example, the TS-SpCas9 may be a SpCas9 variant formed by substituting K890 (hydropathy index: −3.9) in the region 3-1 of the wild-type SpCas9 with asparagine (hydropathy index: −3.5), which is an amino acid having a relatively high hydropathy index, and substituting D1127 in the region 4-1 of the wild-type SpCas9 with glutamic acid having a relatively large functional group.

The TS-SpCas9 may be a SpCas9 variant formed by substituting one or more amino acids selected from the amino acid sequence of the first region of the wild-type SpCas9; one or more amino acids selected in the amino acid sequence of the second region of the wild-type SpCas9; and/or one or more amino acids selected in the amino acid sequence of the third region of the wild-type SpCas9 with different amino acids, respectively.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acid having a relatively high hydropathy index; and substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acid having a relatively high hydropathy index.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, substituting M763 (hydropathy index: 1.9) in the region 2-2 of the wild-type SpCas9 with isoleucine (hydropathy index: 4.5), which is an amino acid having a relatively high hydropathy index, and substituting K890 (hydropathy index: −3.9) in the region 3-1 of the wild-type SpCas9 with asparagine (hydropathy index: −3.5), which is an amino acid having a relatively high hydropathy index.

In another exemplary embodiment, the TS-SpCas9 may be a SpCas9 variant formed by substituting F539 and/or I601 in the region 1-3 of the wild-type SpCas9; and F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids, respectively; substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting F539 in the region 1-3 of the wild-type SpCas9 with serine, which is a polar amino acid, substituting F1038 in the region 2-3 of the wild-type SpCas9 with tyrosine, which is a polar amino acid, substituting K890 in the region 3-1 of the wild-type SpCas9 with asparagine, which is an uncharged amino acid, and substituting T1102 in the region 4-1 of the wild-type SpCas9 with proline (hydropathy index: −1.6), which is an amino acid having a relatively low hydropathy index.

For example, the TS-SpCas9 may be a SpCas9 variant formed by substituting I601 in the region 1-3 of the wild-type SpCas9 with glutamic acid, which is a polar amino acid, substituting F1038 in the region 2-3 of the wild-type SpCas9 with tyrosine, which is a polar amino acid, K890 in the region 3-1 of the wild-type SpCas9 with asparagine, which is an uncharged amino acid, and substituting T1102 in the region 4-1 of the wild-type SpCas9 with proline (hydropathy index: −1.6), which is an amino acid having a relatively low hydropathy index.

For example, the TS-SpCas9 may be a SpCas9 variant formed by substituting F539 and I601 in the region 1-3 of the wild-type SpCas9 with serine and asparagine, which are polar amino acids, respectively, substituting F1038 in the region 2-3 of the wild-type SpCas9 with tyrosine, which is a polar amino acid, substituting K890 in the region 3-1 of the wild-type SpCas9 with asparagine, which is an uncharged amino acid, and substituting T1102 in the region 4-1 of the wild-type SpCas9 with proline (hydropathy index: −1.6), which is an amino acid having a relatively low hydropathy index.

In still another exemplary embodiment, the TS-SpCas9 may be a SpCas9 variant formed by substituting F539 and/or I601 in the region 1-3 of the wild-type SpCas9 with one amino acid selected from the group consisting of arginine, asparagine, aspartic acid, glutamic acid, glutamine, histidine, lysine, serine, threonine and tyrosine, which are polar amino acids, respectively; substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acid having a relatively high hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting I601 in the region 1-3 of the wild-type SpCas9 with asparagine, which is a polar amino acid, substituting M763 (hydropathy index: 1.9) in the region 2-2 of the wild-type SpCas9 with isoleucine (hydropathy index: 4.5), which is an amino acid having a relatively high hydropathy index, and substituting K890 in the region 3-1 of the wild-type SpCas9 with asparagine, which is an uncharged amino acid.

For example, the TS-SpCas9 may be a SpCas9 variant formed by substituting F539 and I601 in the region 1-3 of the wild-type SpCas9 with serine and asparagine, which are polar amino acids, respectively, substituting M763 (hydropathy index: 1.9) in the region 2-2 of the wild-type SpCas9 with isoleucine (hydropathy index: 4.5), which is an amino acid having a relatively high hydropathy index, and substituting K890 in the region 3-1 of the wild-type SpCas9 with asparagine, which is an uncharged amino acid.

In another exemplary embodiment, the TS-SpCas9 may be a SpCas9 variant formed by substituting A203 (hydropathy index: 1.8) in the region 1-1 of the wild-type SpCas9 with one amino acid selected from the group consisting of arginine, asparagine, aspartic acid, glutamic acid, glutamine, glycine, histidine, lysine, proline, serine, threonine, tryptophan and tyrosine, which are amino acids having a relatively low hydropathy index; substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, substituting M763 (hydropathy index: 1.9) in the region 2-2 of the wild-type SpCas9 with isoleucine (hydropathy index: 4.5), which is an amino acid having a relatively high hydropathy index, substituting F1038 in the region 2-3 with tyrosine, which is a polar amino acid, and substituting K890 in the region 3-1 of the wild-type SpCas9 with asparagine, which is an uncharged amino acid.

In yet another exemplary embodiment, the TS-SpCas9 may be a SpCas9 variant formed by substituting I601 (hydropathy index: 4.5) in the region 1-3 of the wild-type SpCas9 with one amino acid selected from the group consisting of alanine, arginine, asparagine, aspartic acid, cysteine, glutamic acid, glutamine, glycine, histidine, leucine, lysine, methionine, phenylalanine, proline, serine, threonine, tryptophan, tyrosine and valine, which are amino acids having a relatively low hydropathy index; substituting D965 (hydropathy index: −3.5) in the region 2-3 of the wild-type SpCas9 with one amino acid selected from the group consisting of alanine, cysteine, glycine, histidine, isoleucine, leucine, methionine, phenylalanine, proline, serine, threonine, tryptophan, tyrosine and valine, which are amino acids having a relatively high hydropathy index; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting I601 (hydropathy index: 4.5) in the region 1-3 of the wild-type SpCas9 with asparagine (hydropathy index: −3.5), which is an amino acid having a relatively low hydropathy index, substituting M763 (hydropathy index: 1.9) in the region 2-2 of the wild-type SpCas9 with isoleucine (hydropathy index: 4.5), which is an amino acid having a relatively high hydropathy index, substituting D965 (hydropathy index: −3.5) in the region 2-3 of the wild-type SpCas9 with tyrosine (hydropathy index: −1.3), which is an amino acid having a relatively high hydropathy index, and substituting T1102 (hydropathy index: −0.7) in the region 4-1 of the wild-type SpCas9 with proline (hydropathy index: −1.6) having a relatively low hydropathy index.

In one exemplary embodiment, the TS-SpCas9 may be a SpCas9 variant formed by substituting one or more amino acids selected from the group consisting of A203 and N277 in the region 1-1, G366 in the region 1-2, and F539 and I601 in the region 1-3 of the wild-type SpCas9 with amino acid(s) having a relatively small or large functional group; substituting one or more amino acids selected from the group consisting of M763 in the region 2-2 and D956 and F1038 in the region 2-3 of the wild-type SpCas9 with amino acid(s) having a relatively small or large functional group; substituting K890 in the region 3-1 of the wild-type SpCas9 with an uncharged amino acid; and substituting one or more amino acids selected from the group consisting of T1102 and D1127 in the region 4-1 of the wild-type SpCas9 with amino acid(s) having a relatively small or large functional group.

For example, the TS-SpCas9 may be a SpCas9 variant formed by substituting G366 in the region 1-2, and F539 and I601 in the region 1-3 of the wild-type SpCas9 with serine (amino acid having a relatively large functional group), serine (amino acid having a relatively small functional group) and asparagine (amino acid having a relatively large functional group), respectively, substituting M763 in the region 2-2 and F1038 in the region 2-3 with isoleucine (amino acid having a relatively small functional group) and tyrosine (amino acid having a relatively large functional group), respectively, substituting K890 in the region 3-1 with uncharged asparagine, and substituting D1127 in the region 4-1 with glutamic acid having a relatively large functional group.

For example, the TS-SpCas9 may be a SpCas9 variant formed by substituting A203 and N277 in the region 1-1, G366 in the region 1-2, and F539 and I601 in the region 1-3 of the wild-type SpCas9 with aspartic acid (amino acid having a relatively large functional group), histidine (amino acid having a relatively large functional group), serine (amino acid having a relatively large functional group), serine (amino acid having a relatively small functional group) and asparagine (amino acid having a relatively large functional group), respectively, substituting M763 in the region 2-2 and D956 and F1038 in the region 2-3 of the wild-type SpCas9 with isoleucine (amino acid having a relatively small functional group), tyrosine (amino acid having a relatively large functional group) and tyrosine (amino acid having a relatively large functional group), respectively, substituting K890 in the region 3-1 of the wild-type SpCas9 with uncharged asparagine, and substituting T1102 and D1127 in the region 4-1 with proline (amino acid having a relatively small functional group) and glutamic acid (amino acid having a relatively large functional group), respectively.

As an example of the TS-SpCas9 disclosed herein, the TS-SpCas9 may be a SpCas9 variant formed by substituting F539, M763 and/or K890 of the wild-type SpCas9 with different amino acids.

In one exemplary embodiment, the TS-SpCas9 may be a SpCas9 variant formed by substituting F539 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine.

For example, the TS-SpCas9 may be a SpCas9 variant formed by substituting F539 of the wild-type SpCas9 with serine. Here, the TS-SpCas9 (F539S) formed by substituting F539 with serine may be a SpCas9 variant in which the interaction between the REC domain of SpCas9 (F539S) and a target sequence and/or the PAM distal end of gRNA may be changed, compared to the wild-type SpCas9.

In one exemplary embodiment, the TS-SpCas9 may be a SpCas9 variant formed by substituting M763 of the wild-type SpCas9 with one amino acid selected from the group consisting of cysteine, isoleucine, leucine, phenylalanine and valine.

For example, the TS-SpCas9 may be a SpCas9 variant formed by substituting M763 of the wild-type SpCas9 with isoleucine. Here, the TS-SpCas9 (F539S) formed by substituting M763 with isoleucine may be a SpCas9 variant in which the interaction between the RuvC domain of SpCas9 (M763I) and a metal may be changed, compared to the wild-type SpCas9.

In one exemplary embodiment, the TS-SpCas9 may be a SpCas9 variant formed by substituting K890 of the wild-type SpCas9 with alanine, asparagine, cysteine, glutamine, glycine, isoleucine, leucine, methionine, phenylalanine, proline, serine, threonine, tryptophan, tyrosine and valine.

For example, the SpCas9 may be a SpCas9 variant formed by substituting K890 of the wild-type SpCas9 with asparagine. Here, the TS-SpCas9 (K890N) formed by substituting K890 with asparagine may be a SpCas9 variant in which the interaction between the HNH domain of SpCas9 (K890N) and a metal is changed, compared to the wild-type SpCas9.

In another exemplary embodiment, the TS-SpCas9 may be a SpCas9 variant formed by substituting F539 and M763 of the wild-type SpCas9 with amino acids different from the original ones, respectively.

Here, the amino acids different from the original ones may be amino acids selected from the group consisting of alanine, arginine, asparagine, aspartic acid, cysteine, glutamic acid, glutamine, glycine, histidine, lysine, methionine, proline, serine, threonine, tryptophan, tyrosine, isoleucine, leucine, phenylalanine and valine.

For example, the TS-SpCas9 may be a SpCas9 variant formed by substituting F539 and M763 of the wild-type SpCas9 with serine and isoleucine, respectively. Here, the TS-SpCas9 (F539S, M763I) in which the F539 and M763 are substituted with serine and isoleucine, respectively, may be a SpCas9 variant in which the interaction between the REC domain of SpCas9 (F539S, M763I) and a target sequence and/or the PAM distal end of gRNA and the interaction between the RuvC domain of the SpCas9 (F539S, M763I) and a metal are changed, compared to the wild-type SpCas9.

In still another exemplary embodiment, the TS-SpCas9 may be a SpCas9 variant formed by substituting F539 and K890 of the wild-type SpCas9 with amino acids different form the original amino acids.

Here, the amino acids different form the original amino acids may be amino acids selected from the group consisting of alanine, arginine, asparagine, aspartic acid, cysteine, glutamic acid, glutamine, glycine, histidine, lysine, methionine, proline, serine, threonine, tryptophan, tyrosine, isoleucine, leucine, phenylalanine and valine.

For example, the TS-SpCas9 may be a SpCas9 variant formed by substituting F539 and K890 of the wild-type SpCas9 with serine and asparagine, respectively. Here, the TS-SpCas9 (F539S, K890N) formed by substituting F539 and K890 with serine and asparagine, respectively, may be a SpCas9 variant in which the interaction between the REC domain of SpCas9 (F539S, K890N) and a target sequence and/or the PAM distal end of gRNA, and the interaction between the HNH domain of the SpCas9 (F539S, K890N) and a metal are changed, compared to the wild-type SpCas9.

In another one exemplary embodiment, the TS-SpCas9 may be a SpCas9 variant formed by substituting M763 and K890 of the wild-type SpCas9 with amino acids different from the original ones.

Here, the amino acids different from the original ones may be amino acids selected from the group consisting of alanine, asparagine, cysteine, glutamine, glycine, isoleucine, leucine, methionine, phenylalanine, proline, serine, threonine, tryptophan, tyrosine and valine.

For example, the TS-SpCas9 may be a SpCas9 variant formed by substituting M763 and K890 of the wild-type SpCas9 with isoleucine and asparagine, respectively. Here, TS-SpCas9 (M763I, K890N) formed by substituting the M763 and K890 with isoleucine and asparagine, respectively, may be a SpCas9 variant in which the interaction between the RuvC domain of SpCas9 (M763I, K890N) and a metal, and the interaction between the HNH domain of SpCas9 (M763I, K890N) and a metal are changed, compared to the wild-type SpCas9.

In one exemplary embodiment, the TS-SpCas9 may be a SpCas9 variant formed by substituting F539, M763 and K890 of the wild-type SpCas9 with amino acids different from the original ones.

Here, the amino acids different from the original ones may be amino acids selected from the group consisting of alanine, arginine, asparagine, aspartic acid, cysteine, glutamic acid, glutamine, glycine, histidine, lysine, methionine, proline, serine, threonine, tryptophan, tyrosine, isoleucine, leucine, phenylalanine and valine.

For example, the TS-SpCas9 may be a SpCas9 variant (SEQ ID NO: 11) formed by substituting F539, M763 and K890 of the wild-type SpCas9 with serine, isoleucine and asparagine. Here, the TS-SpCas9 (F539S, M763I, K890N) formed by substituting F539, M763 and K890 with serine, isoleucine and asparagine, respectively, may be a SpCas9 variant in which the interaction between the REC domain of SpCas9 (F539S, M763I, K890N) and a target sequence and/or the PAM distal end of gRNA, and the interaction between the RuvC domain of the SpCas9 (F539S, M763I, K890N) and a metal, and the interaction between the HNH domain of SpCas9 (F539S, M763I, K890N) and a metal are changed, compared to the wild-type SpCas9.

In one exemplary embodiment of the disclosure disclosed herein, the artificially engineered Cas9 may be a fusion protein.

The fusion protein may be an artificially produced protein including target-specific Cas9 and one or more functional domains.

The descriptions of the target-specific Cas9 have been provided above.

The descriptions of the functional domains have been provided above.

For example, the fusion protein may be an artificially produced protein including TS-SpCas9 and a deaminase.

Here, the TS-SpCas9 may be a SpCas9 variant formed by substituting D10, F539, M763 and K890 of the wild-type SpCas9 with amino acids different from the original ones, respectively.

Alternatively, the TS-SpCas9 may be a SpCas9 variant formed by substituting F539, M763, H840 and K890 of the wild-type SpCas9 with amino acids different from the original ones, respectively.

Alternatively, the TS-SpCas9 may be a SpCas9 variant formed by substituting D10, F539, M763, H840 and K890 of the wild-type SpCas9 with amino acids different from the original ones, respectively.

Here, the deaminase may be an adenine deaminase and/or a cytidine deaminase.

Here, the fusion protein may be an artificially produced protein in the form in which a deaminase is fused to the N-terminus of TS-SpCas9.

Alternatively, the fusion protein may be an artificially produced protein in the form in which a deaminase is fused to the C-terminus of TS-SpCas9.

Alternatively, the fusion protein may be an artificially produced protein in the form in which the same or different deaminases are fused to the N-terminus and the C-terminus of TS-SpCas9, respectively.

A CRISPR enzyme, artificially engineered CRISPR enzyme, CRISPR enzyme variant, Cas9, artificially engineered Cas9, Cas9 variant or target-specific Cas9 disclosed herein may be a polypeptide or protein.

A CRISPR enzyme, artificially engineered CRISPR enzyme, CRISPR enzyme variant, Cas9, artificially engineered Cas9, Cas9 variant or target-specific Cas9 disclosed herein may be a nucleic acid having a nucleotide sequence encoding the polypeptide or protein.

The CRISPR enzyme, artificially engineered CRISPR enzyme, CRISPR enzyme variant, Cas9, artificially engineered Cas9, Cas9 variant or target-specific Cas9 may be codon-optimized for a subject to be introduced.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

The nucleic acid having the nucleotide sequence encoding the polypeptide or protein may be a form of a non-vector.

The non-vector may be naked DNA, a DNA complex or mRNA.

The nucleic acid having the nucleotide sequence encoding the polypeptide or protein may be included in a vector.

Here, the nucleic acid having the nucleotide sequence encoding the polypeptide or protein may be included in one vector, or divided and included in several vectors.

The vector may be a plasmid.

The vector may be a viral vector or a non-viral vector.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capacity of a virus may vary from at least 2 to 50 kb depending on the type of virus. According to the packaging capacity, a viral vector only including a CRISPR enzyme or a viral vector including a CRISPR enzyme and gRNA may be designed. Alternatively, a viral vector including a CRISPR enzyme, gRNA and an additional component may be designed.

In one example, a nucleic acid encoding a CRISPR enzyme may be included in a recombinant lentivirus vector.

In another example, the nucleic acid encoding a CRISPR enzyme may be included in a recombinant adenovirus vector.

In still another example, the nucleic acid encoding a CRISPR enzyme may be included in a recombinant AAV vector.

In yet another example, the nucleic acid encoding a CRISPR enzyme may be included in a hybrid vector, for example, one or more hybrid vectors among viruses disclosed herein.

In one exemplary embodiment disclosed herein, a nucleic acid encoding a CRISPR enzyme variant and/or Cas9 variant may be expressed to use the CRISPR enzyme variant and/or the Cas9 variant. Expression may be performed in various methods. For example, the nucleic acid encoding the CRISPR enzyme variant and/or the Cas9 variant may be cloned into an intermediate virus for transduction into prokaryotic or eukaryotic cells for cloning and/or expression. For storage or manipulation of the nucleic acid encoding the CRISPR enzyme variant and/or the Cas9 variant to produce the CRISPR enzyme variant and/or Cas9 variant, the intermediate vector is typically a prokaryotic vector such as a plasmid, a shuttle vector or an insect vector. In addition, the nucleic acid of the CRISPR enzyme variant and/or the Cas9 variant may be cloned into an expression vector for introduction into plant cells, animal cells, preferably, mammalian cells or human cells, fungal cells, bacterial cells, or protozoan cells.

To accomplish expression, typically, a sequence encoding a CRISPR enzyme variant and/or Cas9 variant is subcloned into an expression vector containing a promoter directing transcription. A bacteria expression system for expressing a engineered protein may be obtained from, for example, *E. coli, Bacillus* sp. and *Salmonella* sp. A kit for the expression system is commercially available. A eukaryotic cell-expressing system for mammalian, yeast and insect cells are widely known in the art, and also commercially available.

A promoter used to direct nucleic acid expression depends on a specific application. For example, a typically strong constitutive promoter is used to express and proliferate a fusion protein. In contrast, when a CRISPR enzyme variant and/or Cas9 variant is introduced into a living body for gene regulation, a constitutive or inducible promoter may be used according to a specific application of the CRISPR enzyme variant and/or Cas9 variant. In addition, a preferable promoter for introducing the CRISPR enzyme variant and/or Cas9 variant may be a weak promoter, for example, HSV TK or a promoter having a similar activity. The promoter may also include transcription activation-response elements, for example, a hypoxia-response element, a Gal4-response element, a lac inhibitor-response element, and small molecule-controlled systems, for example, a tetracycline-regulated system and a RU-486 system.

In addition to the promoter, typically, an expression vector includes a transcription unit or expression cassette containing additional elements required for nucleic acid expression in host cells such as prokaryotic or eukaryotic cells. Therefore, the typical expression cassette may include, for example, a promoter operably linked to a nucleic acid sequence encoding a CRISPR enzyme variant and/or Cas9 variant, and a random signal required for, for example, effective polyadenylation of a transcript, transcription termination, ribosome-binding sites, or translation termination. Additional elements of the cassette may include, for example, an enhancer and spliced heterologous intron signals.

A specific expression vector for transferring genetic information to cells is selected in regard to a desired use of a CRISPR enzyme variant and/or Cas9 variant, for example, expression in plants, animals, bacteria, fungi, protozoa or the like. Standard bacteria expression vectors include plasmids, for example, a pBR322-based plasmid, pSKF and pET23D, and commercially-available tag-fused expression systems, for example, GST and LacZ.

An expression vector containing a regulatory element derived from a eukaryotic cell virus is frequently used in a eukaryotic expression vector, for example, a SV40 vector, a papilloma virus vector, or a vector derived from Epstein-Barr virus. Other exemplary eukaryotic vectors include pMSG, pAV009/A+, pMTO10/A+, pMAMneo-5, baculovirus, pDSVE, and other vectors allowing protein expression under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

A vector for expressing a CRISPR enzyme variant and/or Cas9 variant may include the RNA Pol III promoter for inducing the expression of guide RNA, for example, the H1, U6 or 7SK promoter. Such a human promoter allows the expression of a CRISPR enzyme variant and/or Cas9 variant in mammalian cells after plasmid transfection.

Some expression systems have markers for selecting a stably transfected cell line, for example, thymidine kinase, hygromycin B phosphotransferase, and dihydrofolate reductase. A high yield expression system, for example, using a baculovirus vector in addition to a gRNA-coding sequence under the direction of a polyhedrin promoter or other strong baculovirus promoters in insect cells is also suitable.

Elements typically included in an expression vector also include a replicon functioning in *E. coli*, a gene encoding antibiotic resistance for allowing the selection of bacteria containing a recombinant plasmid, and a unique restriction site in the non-essential region of a plasmid to allow the insertion of a recombinant sequence.

A bacterial, mammalian, yeast or insect cell line expressing a large amount of proteins is produced using a standard transfection method, and purified using a standard technique (For example, refer to Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells is performed according to a standard technique (For example, refer to Morrison, 1977, J. Bacteriol. 132:349-351; Clark-Curtiss & Curtiss, Methods in Enzymology 101:347-362 (Wu et al., eds, 1983)).

Any known procedures for introducing a foreign nucleotide sequence into host cells may be used. These procedures include calcium phosphate transfection, polybrene, protoplast fusion, electroporation, nucleofection, liposomes, microinjection, naked DNA, a plasmid vector, a viral vector, episomal and integrative vectors, and other widely known methods for introducing cloned genome DNA, cDNA, synthetic DNA or other foreign genetic materials into host cells. The specific gene manipulation procedures used herein have to successfully introduce at least one gene into host cells capable of expressing a CRISPR enzyme variant and/or Cas9 variant.

In one exemplary embodiment disclosed herein, a vector capable of expressing a CRISPR enzyme variant and/or Cas9 variant and cells including the vector may be provided.

EXAMPLES

Hereinafter, the present invention will be described in detail with reference to examples.

The examples are merely provided to describe the present invention in further detail, and it might be obvious to those of ordinary skill in the art that the scope of the present invention is not limited to the following examples.

Example 1. Cas9 Variant

1. Cas9 Variant Libraries

SpCas9 variant libraries were constructed using three independent protocols. For the first library, a Cas9 library plasmid was transformed into XL1-red competent cells (Agilent), which were cultured according to the instructions in the vendor's manual. For the second and third libraries, error-prone PCR was performed on whole WT-SpCas9 from Cas9 library plasmid sequences using Genemorph II (Agilent) and Diversify PCR random mutagenesis kits (Clontech) under the condition of a low error rate (0-5 mutations/kb) with primers designed for Gibson Assembly. Subsequently, PCR products were gel-purified. The purified randomly mutagenized library and the backbone of the Cas9 library plasmid were Gibson-assembled. The assembled libraries were transformed into Endura™ electrocompetent cells (Lucigen) and incubated on chloramphenicol LB plates (12.5 μg/mL) at 37° C. overnight. After the transformed cells were cultured, each library was isolated and purified using a Midi prep kit (NucleoBond Xtra Midi EF, Macherey-Nagel). The obtained libraries were screened using a target-specific Cas9 screening method (WO 2017217768) with a multi-target system, thereby selecting target-specific Cas9 variants.

2-1. Plasmids Encoding Target-Specific Cas9 Variants

Plasmids encoding wild-type SpCas9 (p3s-Cas9HC; Addgene plasmid #43945) were purchased and used to produce target-specific SpCas9 variants. Constructs for the target-specific SpCas9 variants were produced by Gibson Assembly of a nucleic acid sequence including desired site mutations and the p3s-Cas9HC plasmid backbone. All constructs were confirmed by Sanger sequencing.

2-2. Plasmids Encoding Target-Specific Cas9 Variants

Plasmids encoding wild-type SpCas9 (p3s-Cas9HC; Addgene plasmid #43945) were purchased and used to produce target-specific SpCas9 variants. To produce target-specific SpCas9 variants, constructs including site mutations were produced in wild-type SpCas9-encoded plasmids using a site-directed mutagenesis kit. All constructs were confirmed by Sanger sequencing.

Example 2. Target Gene Manipulation Effect of Cas9 Variant

Experimental Methods

1. Cell Culture and Transfection Conditions

HEK293T cells (ATCC, CRL-11268) were maintained in DMEM medium supplemented with 10% FBS (fetal bovine serum) and 1% antibiotics. For genetic manipulation by Cas9 variants, HEK293T cells were seeded into 48-well plates until 70-80% confluency before transfection. The cells were transfected with Cas9 variant expression plasmids (250 ng) and sgRNA expression plasmids (250 ng) using Lipofectamine 2000 (Invitrogen). Genomic DNA was isolated and extracted using a DNeasy Blood & Tissue Kit (Qiagen) 72 hours after transfection.

2. In-Vitro Cleavage of Genomic DNA

Genomic DNA was purified from HEK293T cells using a DNeasy Blood & Tissue Kit (Qiagen). The genomic DNA (10 μg) was incubated with Cas9 or Sniper1 protien (100 nM) and 4 sgRNAs (75 nM each) in a reaction volume 1 mL for 8 h at 37° C. in a buffer (100 mM NaCl, 50 mM Tris-HCl, 10 mM MgCl, 100 μg/mL BSA, at pH 7.9). Digested genomic DNA was treated with RNase A (50 μg/mL) to degrade sgRNAs and purified again with DNeasy Blood & Tissue Kit (Qiagen).

3. Whole Genome and Digenome Sequencing

Genomic DNA (1 μg) was fragmented into a 400- to 500-bp range using the Covaris system (Life Technologies), and both ends of the fragments were blunt-ended using End Repair Mix (Thermo Fischer). To construct libraries, fragmented DNA was ligated with an adapter, and then subjected to whole-genome sequencing using a HiSeq X Ten Sequencer (Illumina) at Macrogen. Whole genome sequencing was performed at a sequencing depth of 30-40×. DNA cleavage sites were identified using Digenome 1.0 programs.

4. Targeted Deep Sequencing

Target sites and potential off-target sites were analyzed by targeted deep sequencing. Deep-sequencing libraries were generated by PCR. TruSeq HT Dual Index primers were used to label each sample. Pooled libraries were subjected to paired-end sequencing using MiniSeq.

Experimental Results

In this example, to confirm a target gene manipulation effect of SpCas9 variants, the indel (%) effect of the SpCas9 variants according to the target gene was confirmed with various genes used as a target. Here, the effect of the SpCas9 variants was confirmed for each region.

1. First Region Variants of SpCas9

A total of five SpCas9 variants (A203D, N277H, G366S, F539S and I601N) formed by substituting A203, N277, G366, F539 and I601 in the first region of SpCas9 with different amino acids, respectively, were used in the experiment.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29), a sequence different from the target sequence is shown in lower case), in all SpCas9 variants, compared to the wild-type SpCas9, indel frequencies at the on-target site increased, indel frequencies at the off-target site decreased, which is that the ratio of indel frequency at the off-target site based on the value of the on-target site was low (FIG. 1). Particularly, it was confirmed that, for A203D, F539S and I601N, indel frequencies at on-target sites are similar to those of the wild-type SpCas9, but indel frequencies at off-target sites are lowered below a certain level compared to the wild-type SpCas9.

Figure 2:
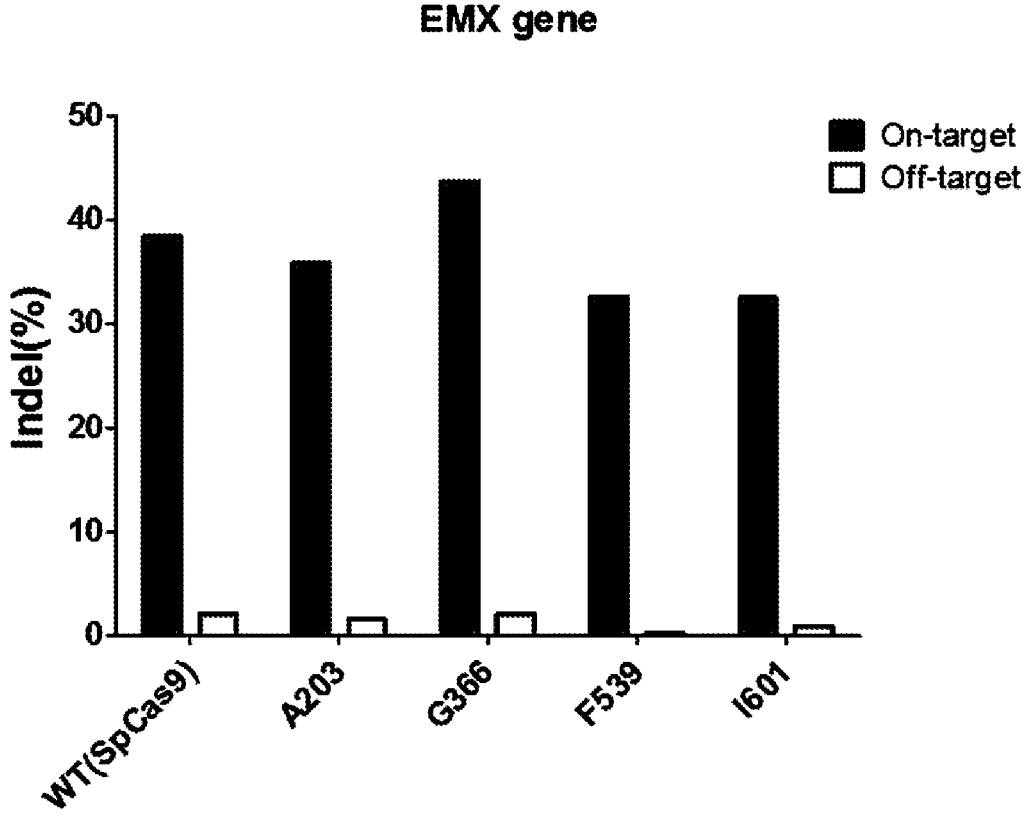
FIG. 2 is a graph showing indel frequencies (%), which represents the manipulation effect of a target gene (EMX gene) by first region variants of SpCas9.

In addition, when an EMX gene was used as a target gene (target sequence: GAGTCCGAGCAGAAGAAGAA (SEQ ID NO: 30)/non-target sequence: GAGT-taGAGCAGAAGAAGAA (SEQ ID NO: 31)), for all SpCas9 variants, compared to the wild-type SpCas9, indel frequencies increased at the on-target site and decreased at the off-target site, which is that the ratio of indel frequency at the off-target site based on the value of the on-target site was low (FIG. 2). Particularly, for G366S, it was confirmed that indel frequencies at the off-target site are similar to those of the wild-type SpCas9, but indel frequencies at the on-target site are higher than those of the wild-type SpCas9. In addition, for F539S and I601N, it was confirmed that indel frequencies at the off-target site are almost not shown or are lowered to half of those of the wild-type SpCas9.

Figure 3:
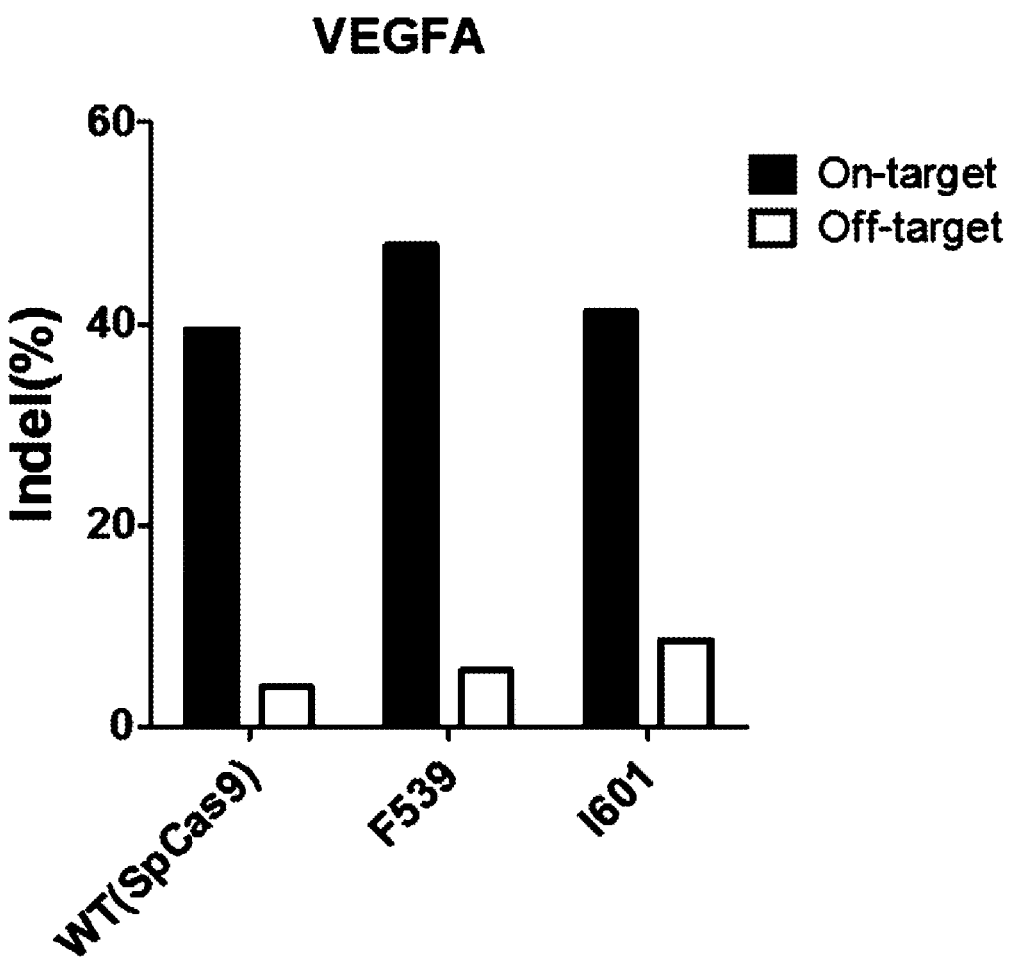
FIG. 3 is a graph showing indel frequencies (%), which represents the manipulation effect of a target gene (VEGFA gene) by first region variants of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), for all SpCas9 variants, compared to the wild-type SpCas9, indel frequencies at the on-target site increased, or were similar to those of the wild-type SpCas9 (FIG. 3). Particularly, for F539S, indel frequencies at the off-target site were similar to those of the wild-type SpCas9, but indel frequencies at the on-target site were 10% or higher than those of the wild-type SpCas9.

From the above-mentioned results, it can be confirmed that a total of five SpCas9 variants formed by substituting A203, N277, G366, F539 and I601 in the first region of SpCas9 with different amino acids are improved in target specificity, compared to the wild-type SpCas9.

2. Second Region Variants of SpCas9

Three SpCas9 variants (M763I, D965Y and F1038Y) formed by substituting M763, D965 and F1038 in the second region of SpCas9 with different amino acids and two SpCas9 variants (M763I/F1038Y and D965Y/F1038Y) formed by substituting M763/F1038 and D965/F1038 in the second region of SpCas9 with different amino acids were used in an experiment.

Figure 4:
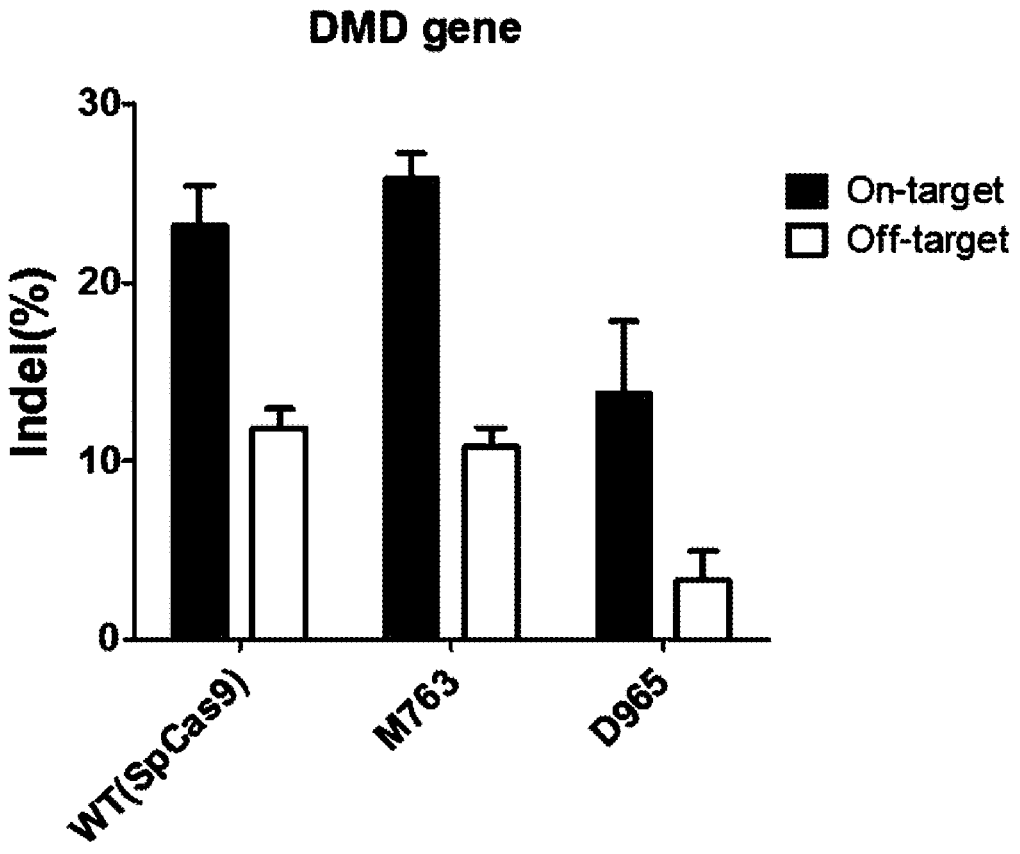
FIGS. 4 and 5 are graphs showing indel frequencies (%), which represents the manipulation effect of a target gene (DMD gene) by second region variants of SpCas9.
Figure 5:
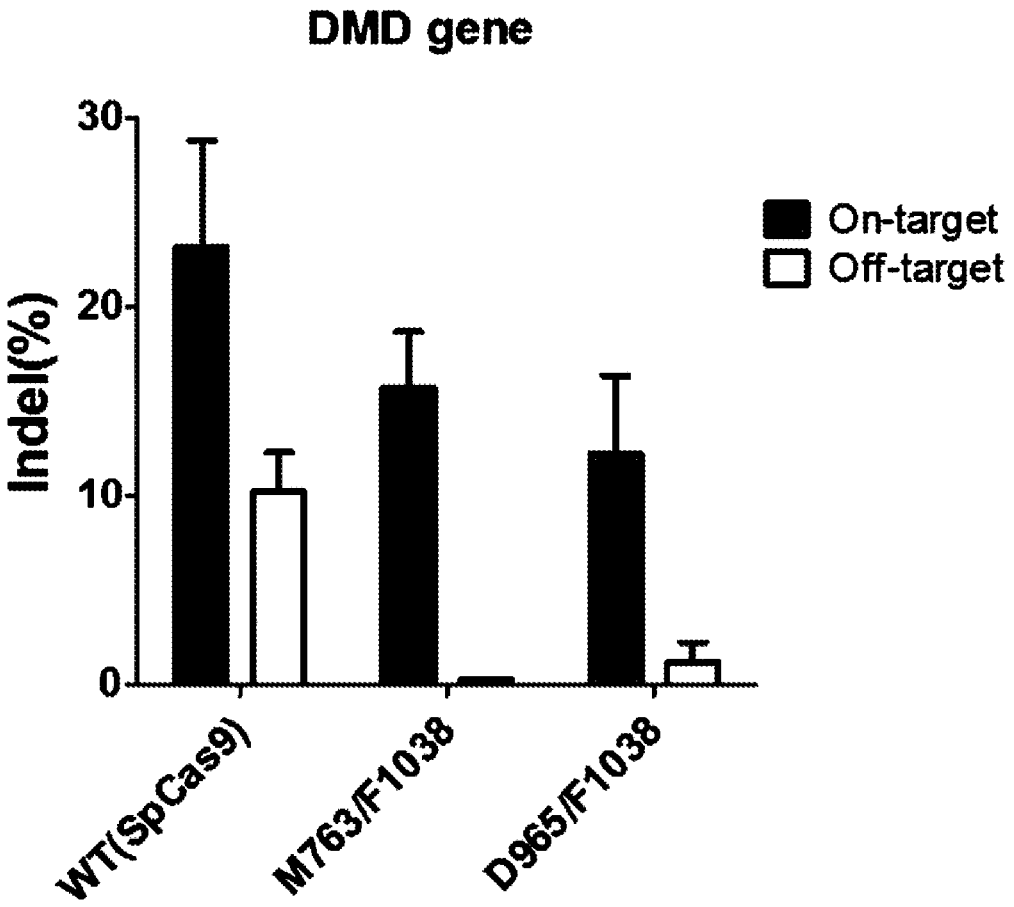

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), for all SpCas9 variants, compared to the wild-type SpCas9, indel frequencies at the on-target site increased, indel frequencies at the off-target site decreased, or the indel frequencies at the off-target site were lower than those at the on-target site (FIG. 4). Particularly, for M763I, it was confirmed that indel frequencies at the off-target site were similar to those of wild-type SpCas9, but indel frequencies at the on-target site were higher than those of the wild-type SpCas9. In addition, for M763I/F1038Y and D965Y/F1038Y, it was confirmed that indel frequencies at the on-target site are slightly lower than those of the wild-type SpCas9, but indel frequencies at the off-target site are almost not shown, and thus the ratio of indel frequency at the off-target site based on the value of the on-target site was lower than those of the wild-type SpCas9. Therefore, it was confirmed that the SpCas9 variants have target specificity, compared to the wild-type SpCas9 (FIG. 5).

Figure 6:
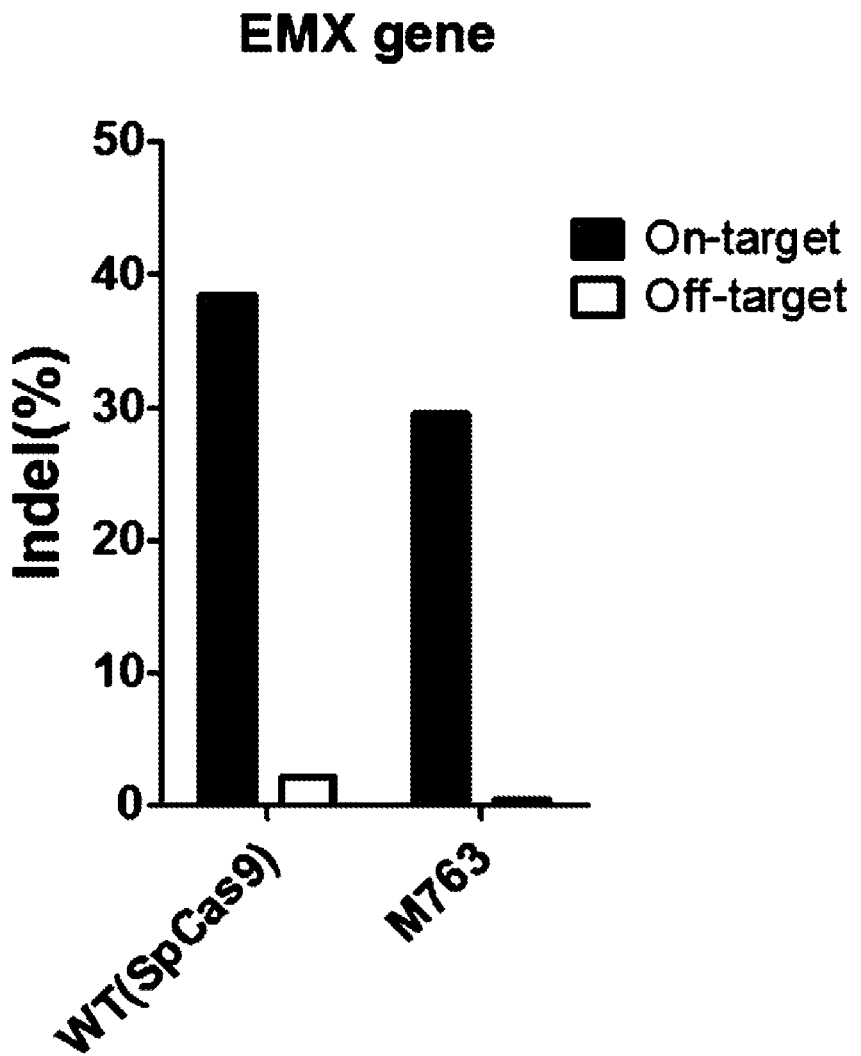
FIGS. 6 and 7 are graphs showing indel frequencies (%), which represents the manipulation effect of a target gene (EMX gene) by second region variants of SpCas9.
Figure 7:
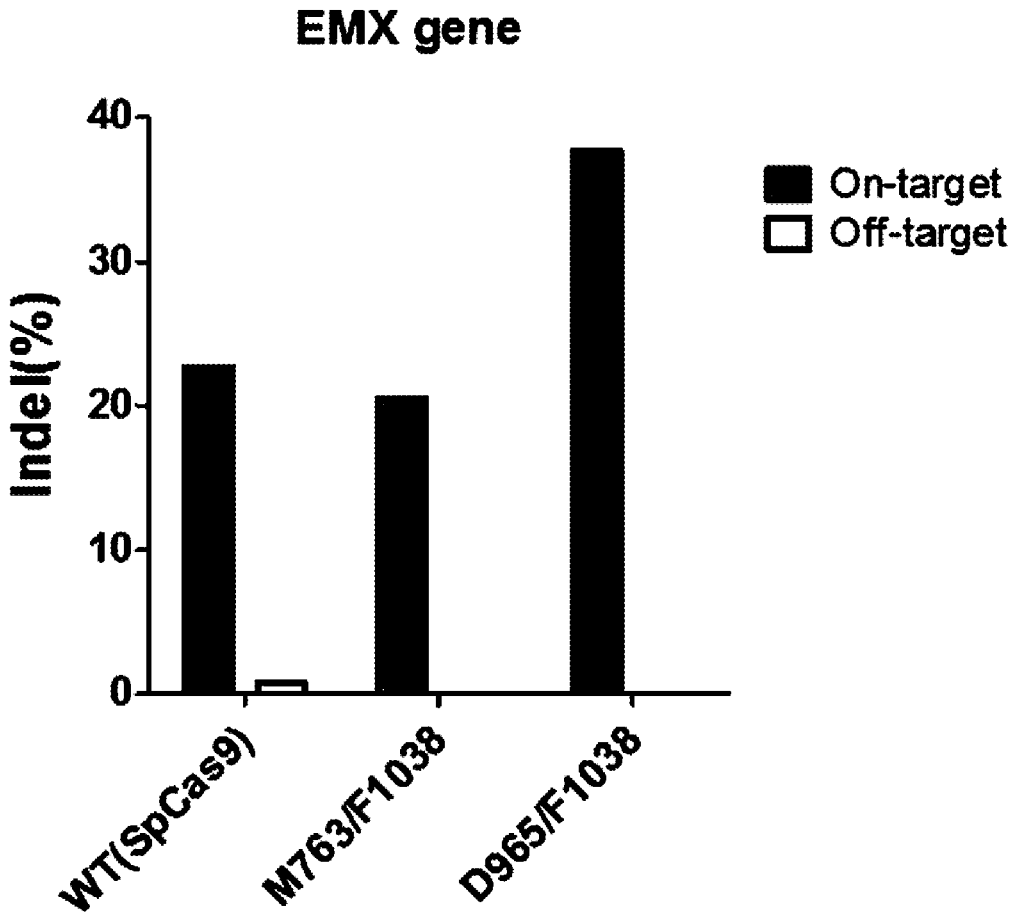

In addition, when an EMX gene was used as a target gene (target sequence: GAGTCCGAGCAGAAGAAGAA (SEQ ID NO: 30)/non-target sequence: GAGT-taGAGCAGAAGAAGAA (SEQ ID NO: 31)), for M763I, compared to the wild-type SpCas9, indel frequencies at the on-target site were slightly lowered, but indel frequencies at the off-target site were almost not shown, and thus the ratio of indel frequency at the off-target site based on the value of the on-target site was low. Therefore, M763I has target specificity, compared to the wild-type SpCas9 (FIG. 6). In addition, for M763I/F1038Y and D965Y/F1038Y, indel frequencies at the off-target site were almost not shown, and indel frequencies at the on-target site were similar to or significantly higher, compared to the wild-type SpCas9 (FIG. 7).

Figure 8:
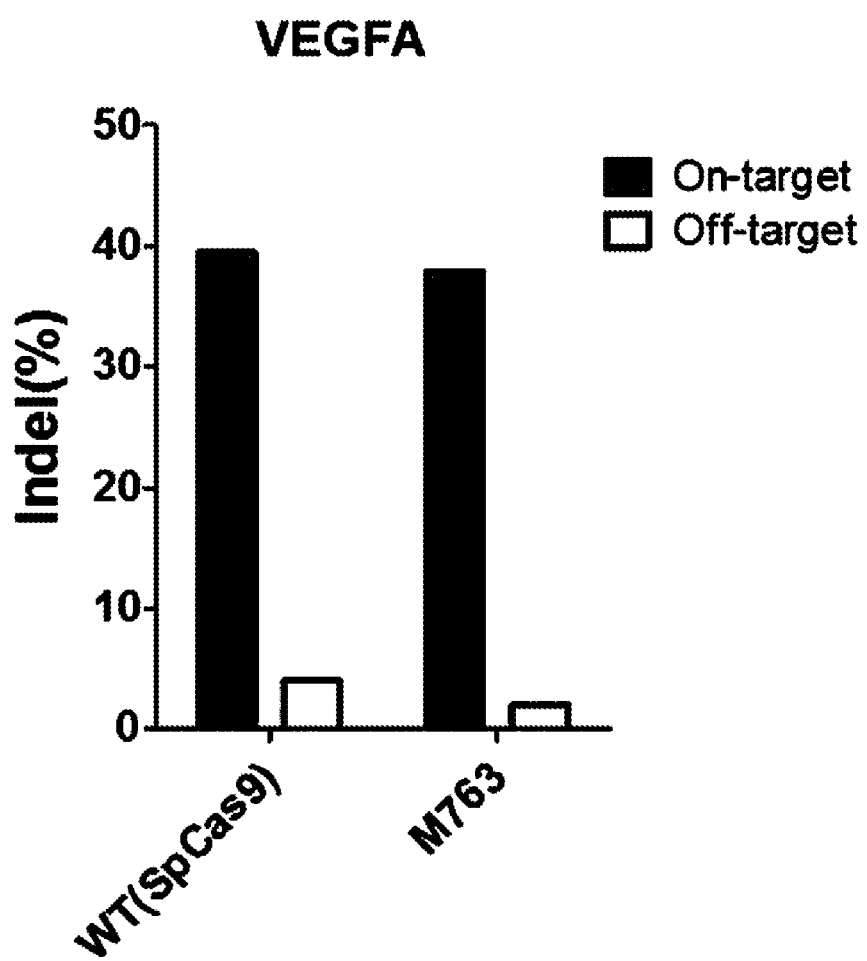
FIG. 8 is a graph showing indel frequencies (%), which represents the manipulation effect of a target gene (VEGFA gene) by second region variants of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), for M763I, compared to the wild-type SpCas9, indel frequencies at the on-target site were similar, but indel frequencies at the off-target site were almost not shown, and thus it can be confirmed that for M763I, compared to the wild-type SpCas9, which is that the ratio of indel frequency at the off-target site based on the value of the on-target site was low, and thus M763I has target specificity, compared to the wild-type SpCas9 (FIG. 8).

Figure 9:
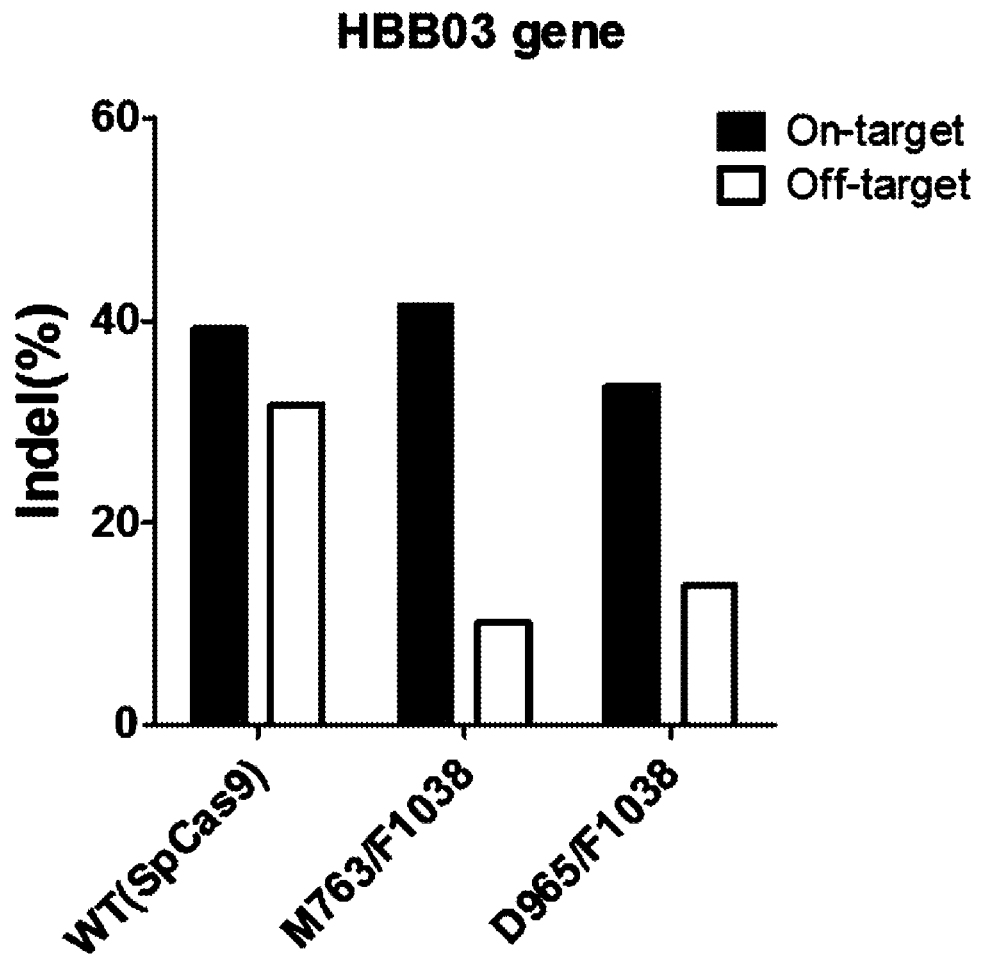
FIG. 9 is a graph showing indel frequencies (%), which represents the manipulation effect of a target gene (HBB03 gene) by second region variants of SpCas9.

When an HBB03 gene was used as a target gene (target sequence: CACGTTCACCTTGCCCCACA (SEQ ID NO: 34)/non-target sequence: CACGTTCACtTTGCCCCACA (SEQ ID NO: 35)), it was confirmed that, for M763I/F1038Y and D965Y/F1038Y, compared to the wild-type SpCas9, indel frequencies at the off-target site decrease by half or less, but indel frequencies at the on-target site increase or slightly decrease (FIG. 9).

Figure 10:
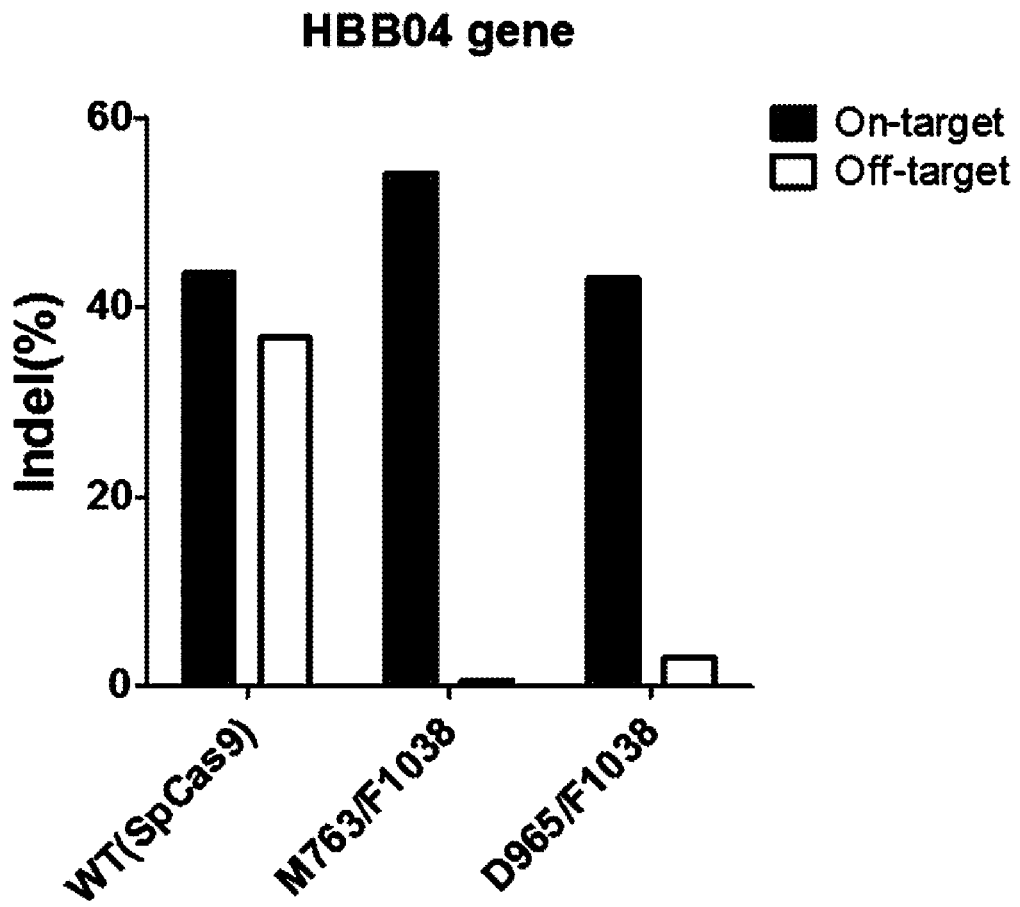
FIG. 10 is a graph showing indel frequencies (%), which represents the manipulation effect of a target gene (HBB04 gene) by second region variants of SpCas9.

When an HBB04 gene was used as a target gene (target sequence: CCACGTTCACCTTGCCCCAC (SEQ ID NO: 36)/non-target sequence: CCACaTTCACCTTGCCCCAC (SEQ ID NO: 37)), it was confirmed that, for M763I/F1038Y and D965Y/F1038Y, compared to the wild-type SpCas9, indel frequencies at the off-target site are almost not shown, and indel frequencies at the on-target site increase or similar (FIG. 10).

From the above-mentioned results, it can be confirmed that the three SpCas9 variants (M763I, D965Y and F1038Y) formed by substituting M763, D965 and F1038 in the second region of SpCas9 with different amino acids and two SpCas9 variants (M763I/F1038Y and D965Y/F1038Y) formed by substituting M763/F1038 and D965/F1038 in the second region of SpCas9 with different amino acids were improved in target specificity, compared to the wild-type SpCas9.

3. Third Region Variants of SpCas9

A SpCas9 variant (K890N) formed by substituting K890 in the third region of SpCas9 with different amino acid were used in the experiment.

Figure 11:
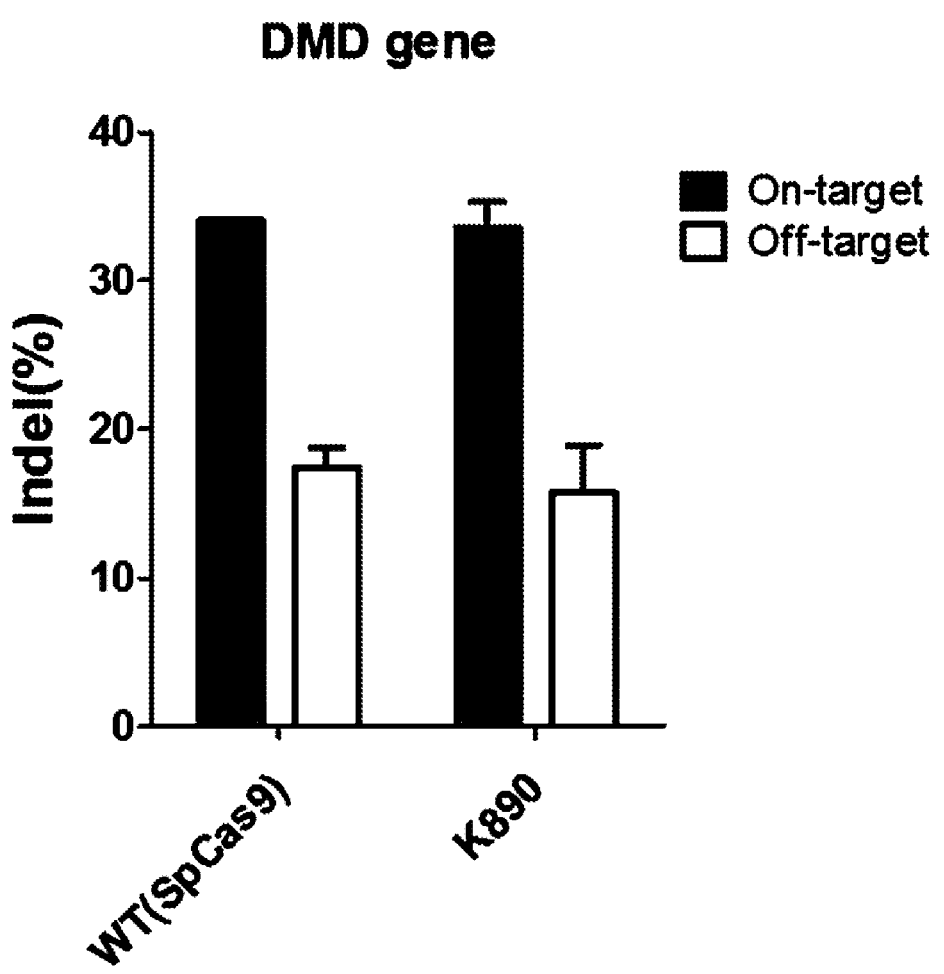
FIG. 11 is a graph showing indel frequencies (%), which represents the manipulation effect of a target gene (DMD gene) by third region variants of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for K890N, compared to the wild-type SpCas9, indel frequencies at the on-target site are similar, but indel frequencies at the off-target site slightly decrease (FIG. 11).

Form the above-mentioned results, it can be confirmed that the SpCas9 variant (K890N) formed by substituting K890 in the third region of SpCas9 with a different amino acid shows similar or slightly increased target specificity, compared to the wild-type SpCas9.

4. Fourth Region Variants of SpCas9

SpCas9 variants (T1102P and D1127E) formed by substituting T1102 and D1127 in the fourth region of SpCas9 with different amino acids were used in the experiment.

Figure 12:
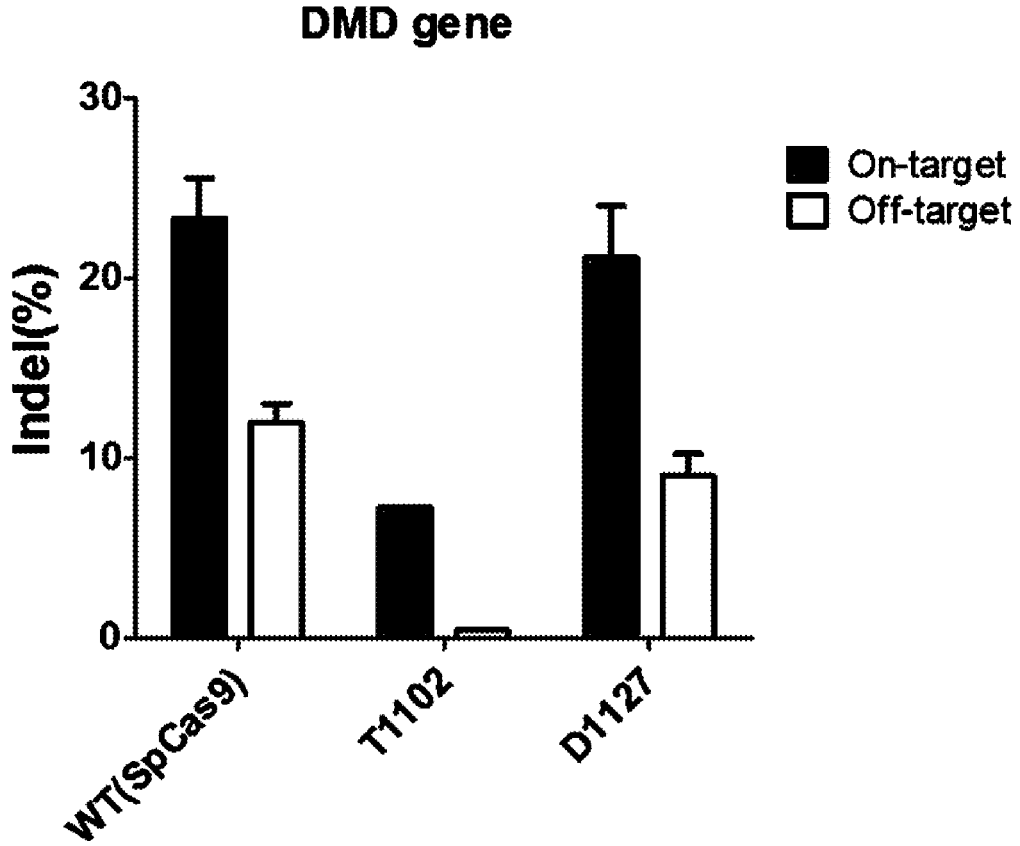
FIG. 12 is a graph showing indel frequencies (%), which represents the manipulation effect of a target gene (DMD gene) by fourth region variants of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for T1102P, compared to the wild-type SpCas9, almost no indel frequencies at the off-target site are shown, and for D1127E, compared to the wild-type SpCas9, indel frequencies at the on-target site are similar, but indel frequencies at the off-target site decrease (FIG. 12).

Figure 13:
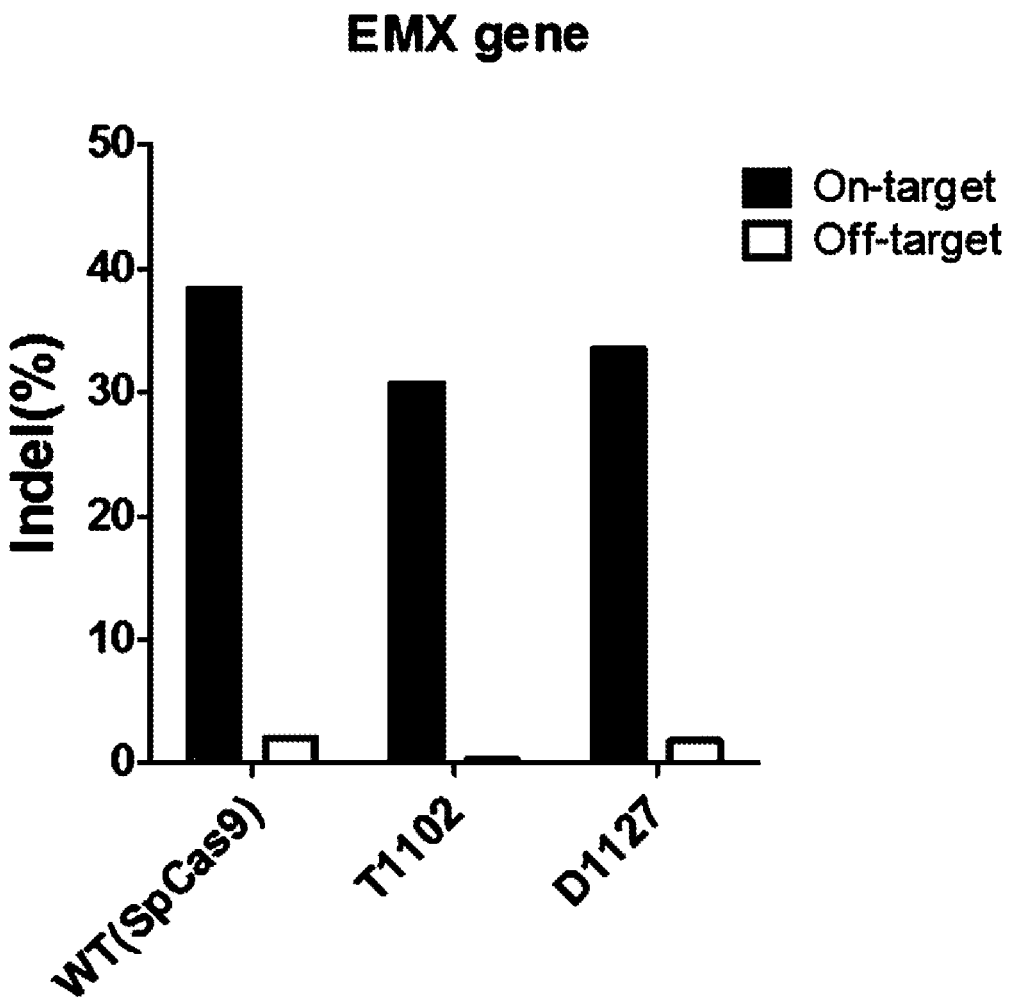
FIG. 13 is a graph showing indel frequencies (%), which represents the manipulation effect of a target gene (EMX gene) by fourth region variants of SpCas9.

In addition, when an EMX gene was used as a target gene (target sequence: GAGTCCGAGCAGAAGAAGAA (SEQ ID NO: 30)/non-target sequence: GAGT-taGAGCAGAAGAAGAA (SEQ ID NO: 31)), both T1102 and D1127 showed similar indel frequencies at the on-target site, but almost no indel frequencies at the off-target site, compared to the wild-type SpCas9 (FIG. 13).

Form the above-mentioned results, it can be confirmed that the SpCas9 variants (T1102P and D1127E) formed by substituting T1102 and D1127 in the fourth region of SpCas9 with different amino acids show similar or slightly improved target specificity, compared to the wild-type SpCas9.

5. SpCas9 Variants Having Mutations in Two Regions

SpCas9 variants having mutations in two regions of the four regions of SpCas9 are used in an experiment. Here, F539S/F1038Y, F539S/M763I, I601N/D965Y and F539S/M763I/F1038Y having mutations in the first and second regions; F539S/K890N having mutations in the first and third regions; and M763I/K890N having mutations in the second and third regions were used as SpCas9 variants.

Figure 14:
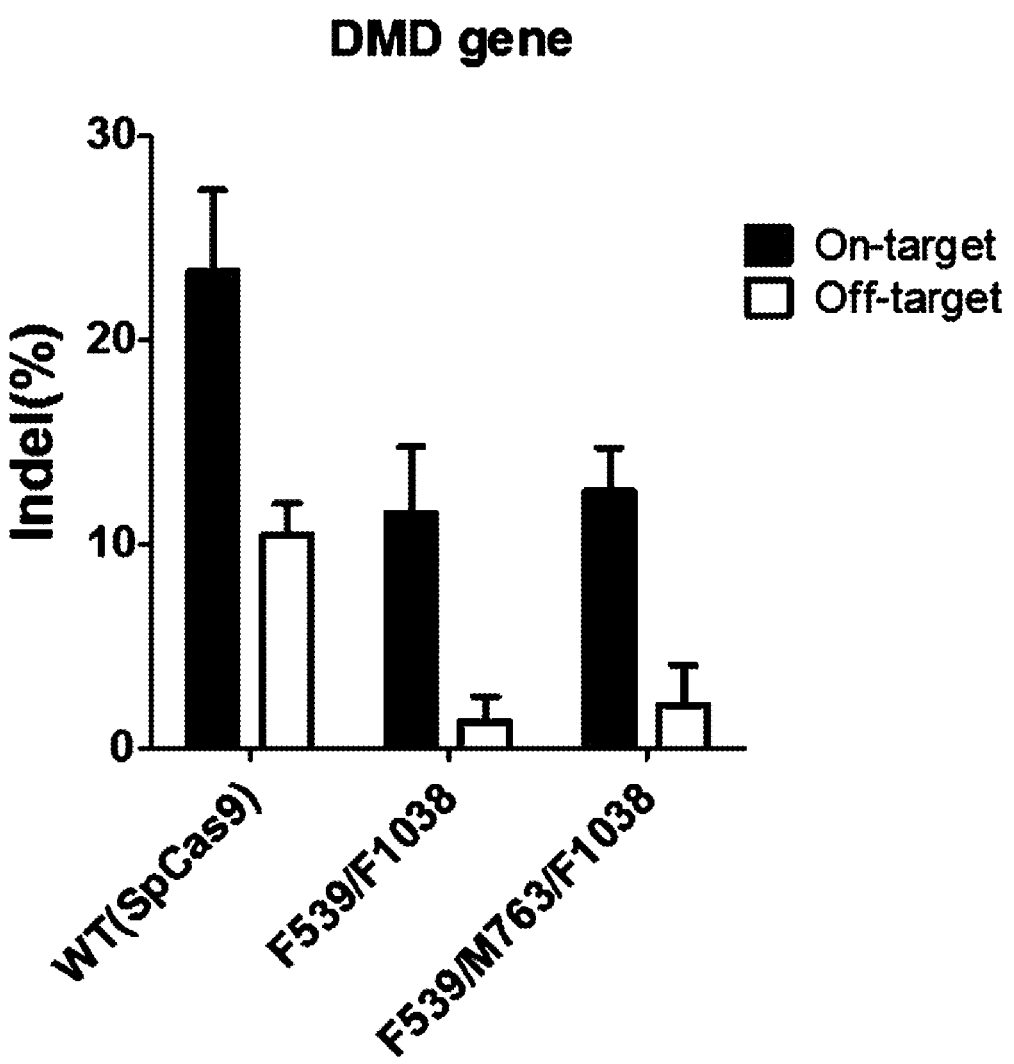
FIG. 14 is a graph showing indel frequencies (%), which represents the manipulation effect of a target gene (DMD gene) by SpCas9 variants having mutations in two regions of the four regions of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for F539S/F1038Y and F539S/M763I/F1038Y, compared to the wild-type SpCas9, indel frequencies at the on-target site decreased, but indel frequencies at the off-target site decreased by approximately 70 to 80%, and thus the ratio of indel frequency at the off-target site based on the value of the on-target site was low. Therefore, it was confirmed that F539S/F1038Y and F539S/M763I/F1038Y have target specificity, compared to the wild-type SpCas9 (FIG. 14).

Figure 15:
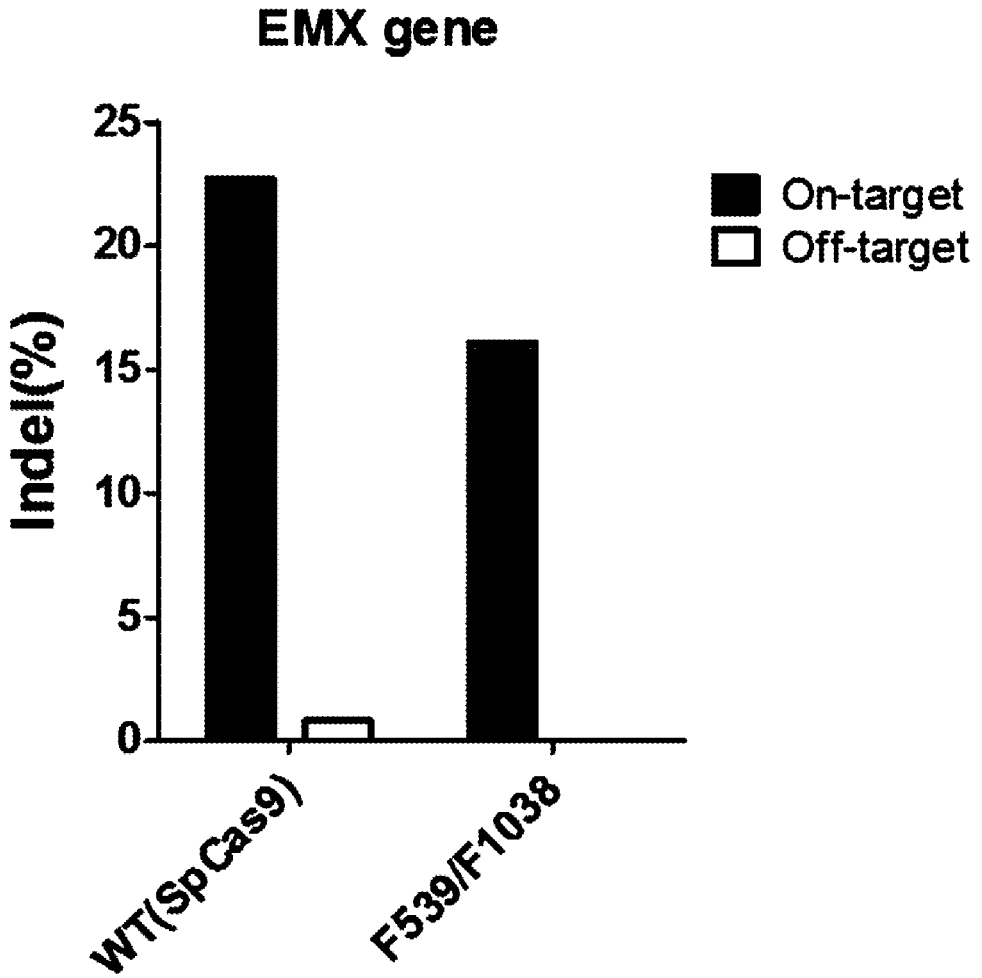
FIG. 15 is a graph showing indel frequencies (%), which represents the manipulation effect of a target gene (EMX gene) by SpCas9 variants having mutations in two regions of the four regions of SpCas9.

In addition, when an EMX gene was used as a target gene (target sequence: GAGTCCGAGCAGAAGAAGAA (SEQ ID NO: 30)/non-target sequence: GAGT-taGAGCAGAAGAAGAA (SEQ ID NO: 31)), for F539S/F1038Y, compared to the wild-type SpCas9, indel frequencies at the on-target site slightly decreased, but indel frequencies at the off-target site were almost not shown, and thus the ratio of indel frequency at the off-target site based on the value of the on-target site was low. Therefore, it was confirmed that F539S/F1038Y has target specificity, compared to the wild-type SpCas9 (FIG. 15).

Figure 16:
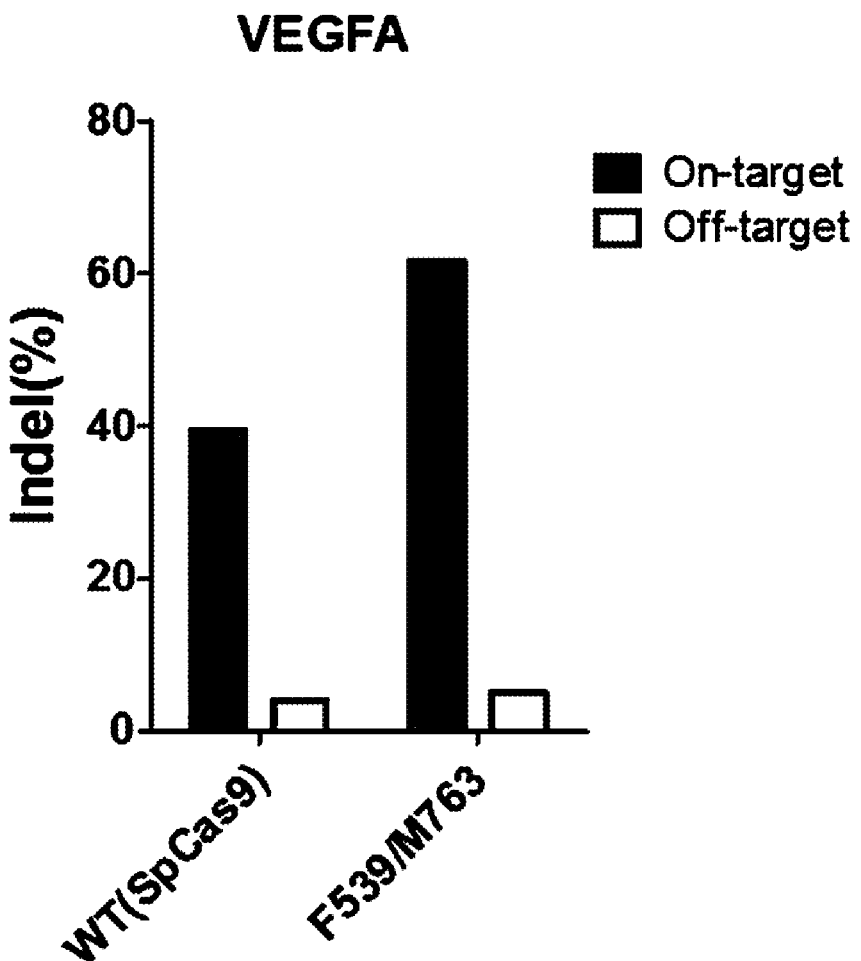
FIG. 16 is a graph showing indel frequencies (%), which represents the manipulation effect of a target gene (VEGFA gene) by SpCas9 variants having mutations in two regions of the four regions of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), it was confirmed that, for F539S/M763I, compared to the wild-type SpCas9, indel frequencies at the off-target site are similar, but indel frequencies at the on-target site significantly increase (FIG. 16).

Figure 17:
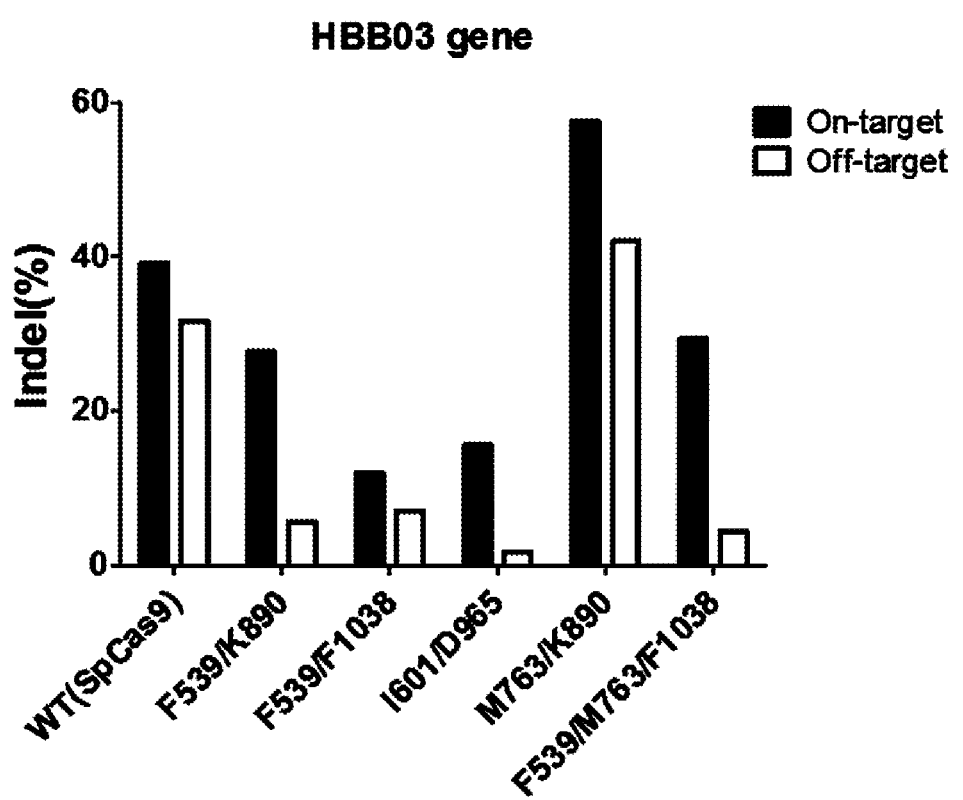
FIG. 17 is a graph showing indel frequencies (%), which represents the manipulation effect of a target gene (HBB03 gene) by SpCas9 variants having mutations in two regions of the four regions of SpCas9.

When an HBB03 gene was used as a target gene (target sequence: CACGTTCACCTTGCCCCACA (SEQ ID NO: 34)/non-target sequence: CACGTTCACtTTGCCCCACA (SEQ ID NO: 35)), it was confirmed that, for F539S/K890N and F539S/M763I/F1038Y, compared to the wild-type SpCas9, indel frequencies at the on-target site slightly decrease, but indel frequencies at the off-target site decrease by 70% or more, and thus the ratio of indel frequency at the off-target site based on the value of the on-target site was low. Therefore, it was confirmed that F539S/K890N and F539S/M763I/F1038Y have target specificity, compared to the wild-type SpCas9 (FIG. 17). In addition, it was confirmed that, for M763I/K890N, compared to the wild-type SpCas9, indel frequencies at the off-target site slightly increase, but indel frequencies at the on-target site increase by approximately 30 to 40%, and thus the ratio of indel frequency at the off-target site based on the value of the on-target site was low. Therefore, it was confirmed that M763I/K890N has target specificity, compared to the wild-type SpCas9 (FIG. 17).

Figure 18:
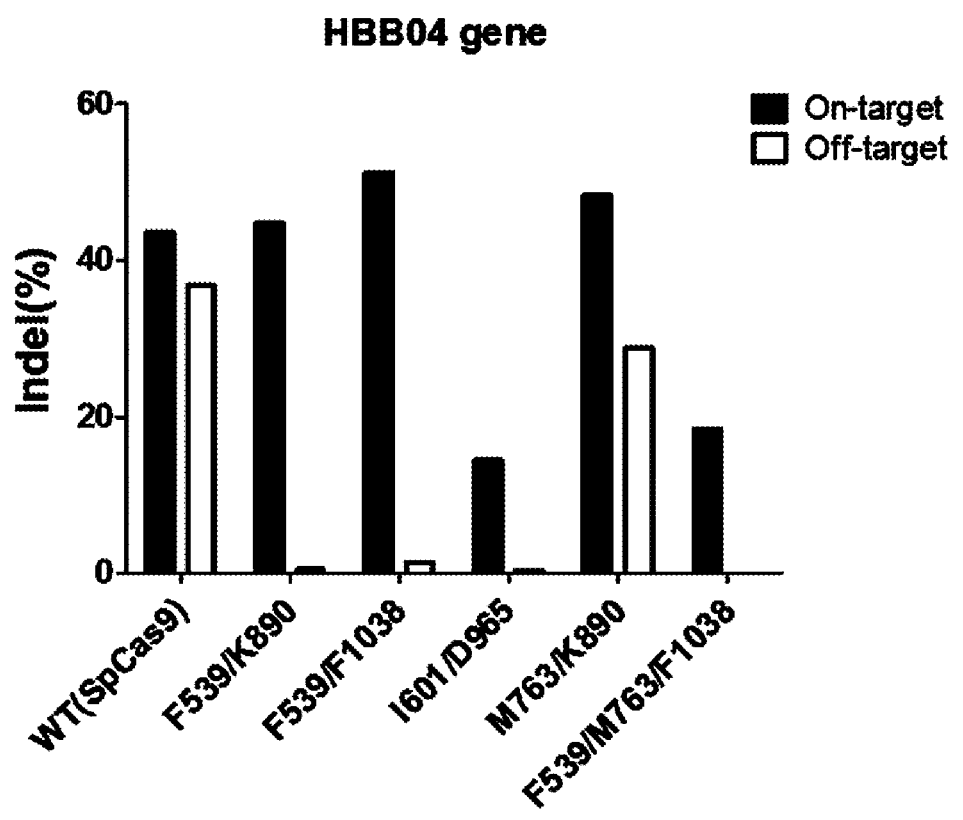
FIG. 18 is a graph showing indel frequencies (%), which represents the manipulation effect of a target gene (HBB04 gene) by SpCas9 variants having mutations in two regions of the four regions of SpCas9.

When an HBB04 gene was used as a target gene (target sequence: CCACGTTCACCTTGCCCCAC (SEQ ID NO: 36)/non-target sequence: CCACaTTCACCTTGCCCCAC (SEQ ID NO: 37)), it was confirmed that, for F539S/K890N and F539S/F1038Y, compared to the wild-type SpCas9, indel frequencies at the on-target site are similar or increase, and indel frequencies at the off-target site are almost not shown (FIG. 18). In addition, it was confirmed that, for M763I/K890N, compared to the wild-type SpCas9, indel frequencies at the on-target site slightly increase, and indel frequencies at the off-target site decrease by approximately 30% (FIG. 18).

Form the above-mentioned results, it can be confirmed that the SpCas9 variants (F539S/K890N, F539S/F1038Y, F539S/M763I, I601N/D965Y, M763I/K890N and F539S/M763I/F1038Y) having mutations in two regions of the four regions of SpCas9 are improved in target specificity, compared to the wild-type SpCas9.

6. SpCas9 Variants Having Mutations in Three or More Regions

SpCas9 variants having mutations in three or more regions of the four regions of SpCas9 were used in the experiment. Here, F539S/M763I/K890N, F539S/M763I/D965Y/K890N and F539S/M763I/K890N/F1038Y having mutations in the first, second and third regions; and A203D/N277H/G366S/M763I/F1038Y/T1102P/D1127E having mutations in the first, second and fourth regions were used as SpCas9 variants.

Figure 19:
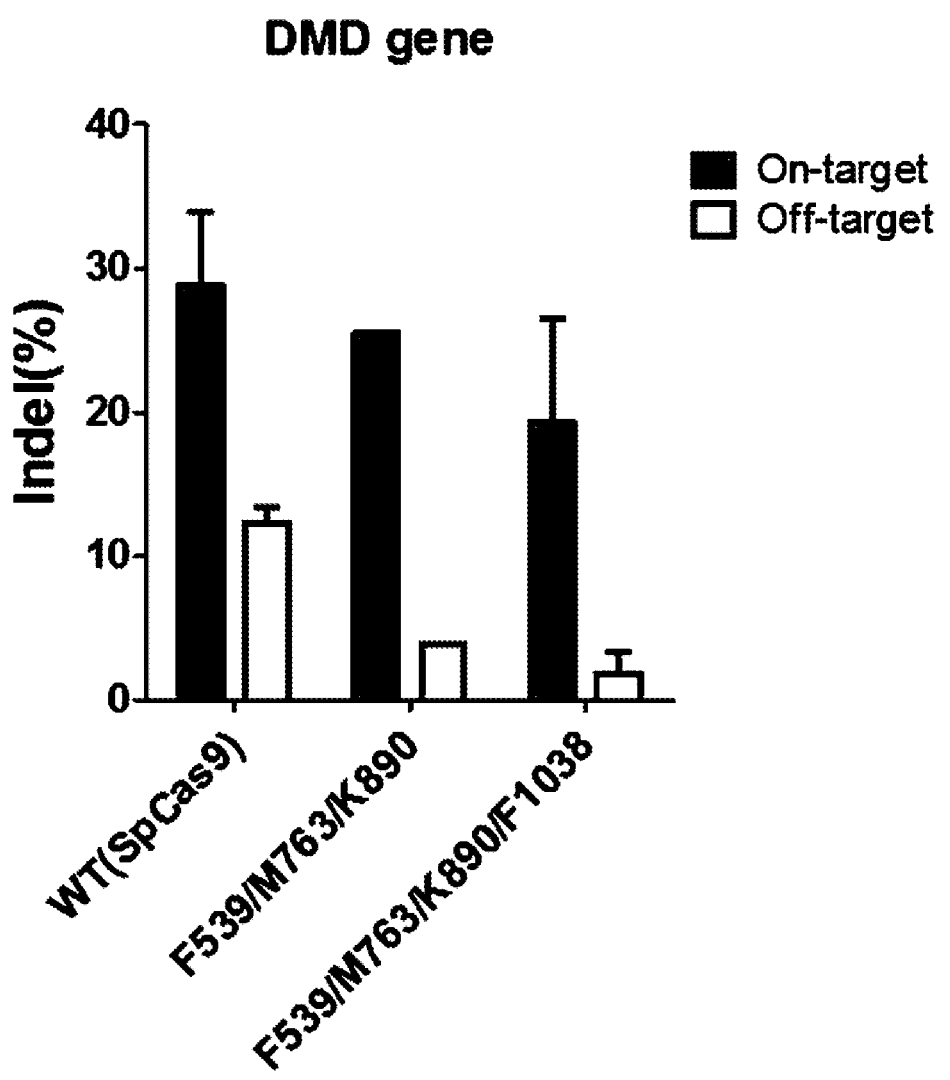
FIG. 19 is a graph showing indel frequencies (%), which represents the manipulation effect of a target gene (DMD gene) by SpCas9 variants having mutations in three regions of the four regions of SpCas9.
Figure 23:
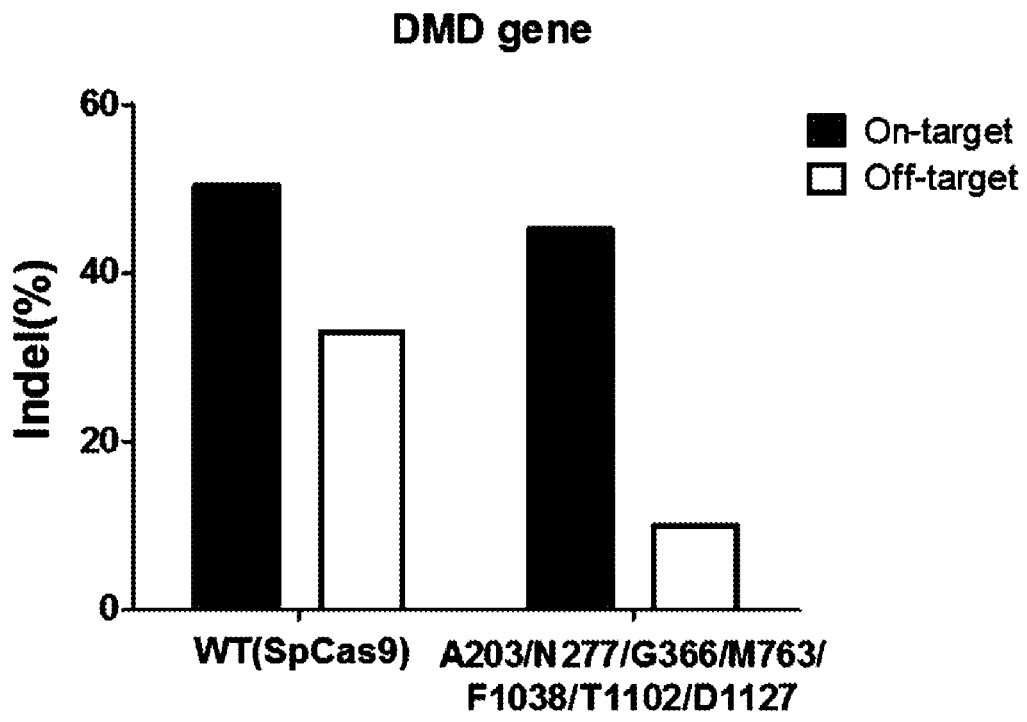
FIG. 23 is a graph showing indel frequencies (%), which represents the manipulation effect of a target gene (DMD gene) by SpCas9 variants having mutations in three regions of the four regions of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for F539S/M763I/K890N and F539S/M763I/K890N/F1038Y, compared to the wild-type SpCas9, indel frequencies at the on-target site slightly decrease, but indel frequencies at the off-target site decrease by half or less, and thus the ratio of indel frequency at the off-target site based on the value of the on-target site was low. Therefore, it was confirmed that for F539S/M763I/K890N and F539S/M763I/K890N/F1038Y have target specificity, compared to the wild-type SpCas9 (FIG. 19). In addition, for A203D/N277H/G366S/M763I/F1038Y/T1102P/D1127E, compared to the wild-type SpCas9, indel frequencies at the on-target site slightly decrease, but indel frequencies at the off-target site decrease by approximately 60 to 70%, and thus the ratio of indel frequency at the off-target site based on the value of the on-target site was low. Therefore, it was confirmed that A203D/N277H/G366S/M763I/F1038Y/T1102P/D1127E has target specificity, compared to the wild-type SpCas9 (FIG. 23).

Figure 20:
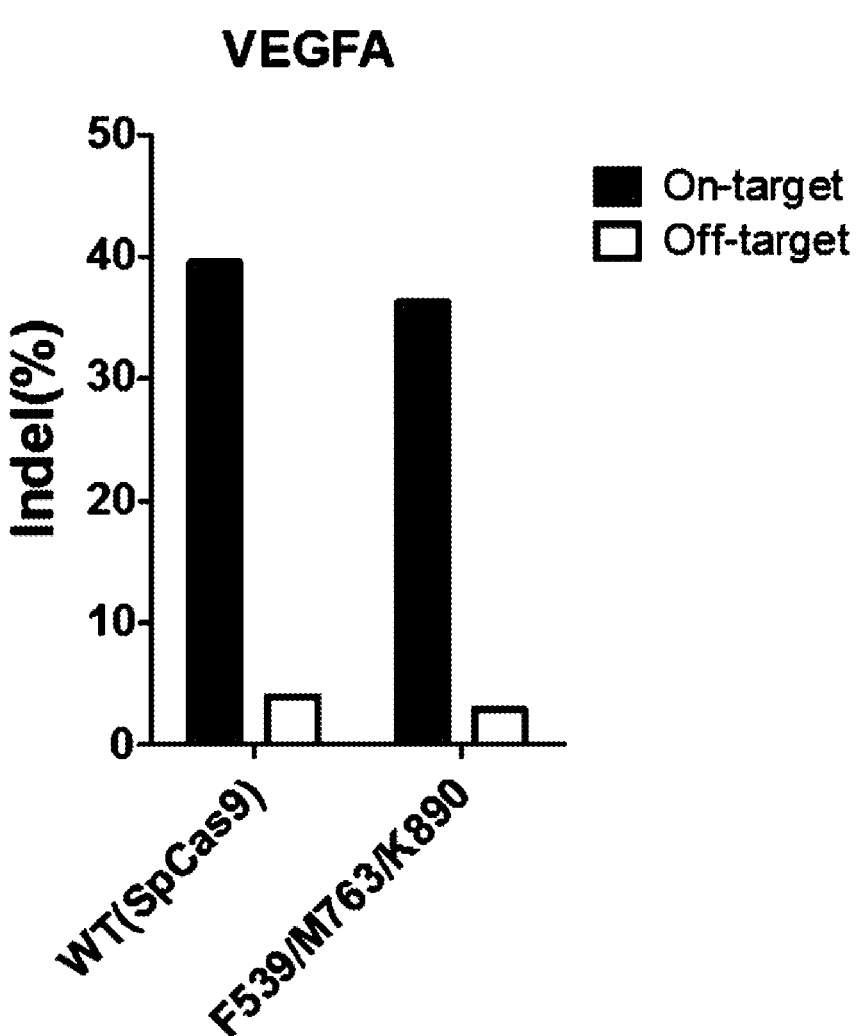
FIG. 20 is a graph showing indel frequencies (%), which represents the manipulation effect of a target gene (VEGFA gene) by SpCas9 variants having mutations in three regions of the four regions of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), it was confirmed that, for F539S/M763I/K890N, compared to the wild-type SpCas9, indel frequencies at the on-target site slightly decrease, but indel frequencies at the off-target site decrease by half, and thus the ratio of indel frequency at the off-target site based on the value of the on-target site was low. Therefore, it was confirmed that F539S/M763I/K890N has target specificity, compared to the wild-type SpCas9 (FIG. 20).

Figure 21:
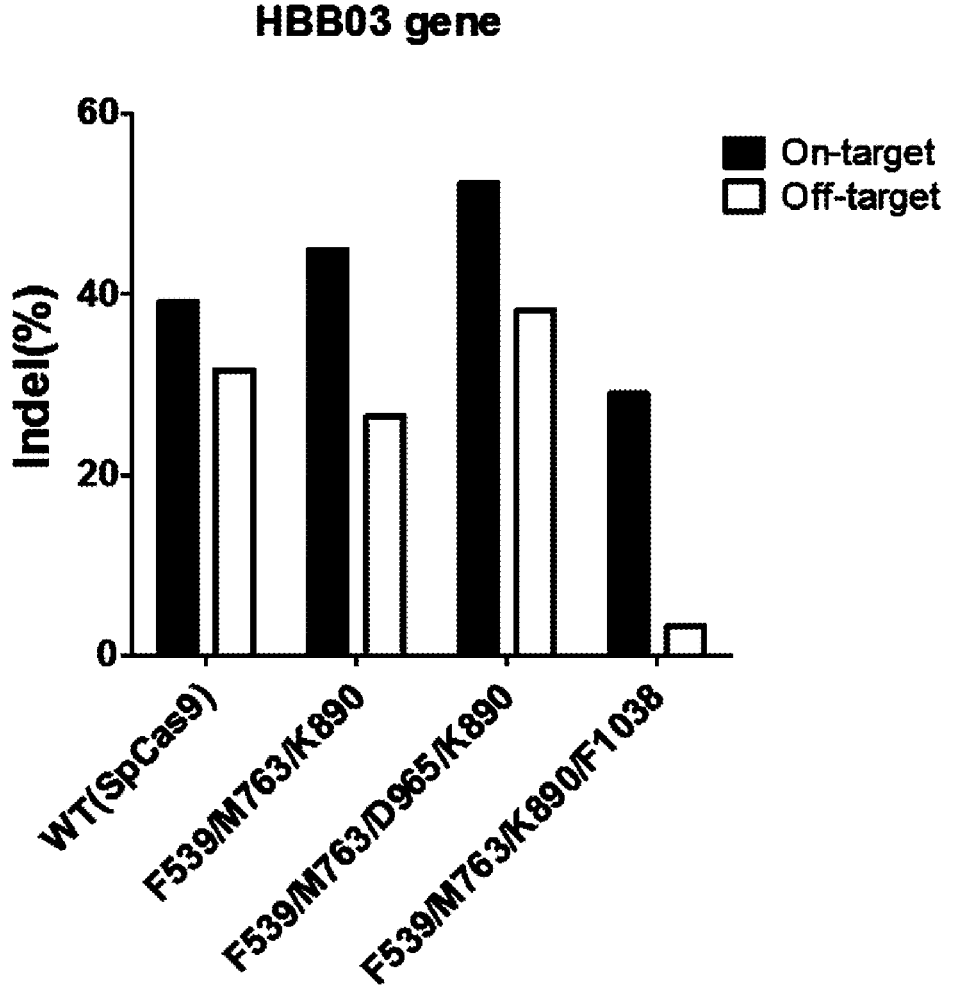
FIG. 21 is a graph showing indel frequencies (%), which represents the manipulation effect of a target gene (HBB03 gene) by SpCas9 variants having mutations in three regions of the four regions of SpCas9.

When an HBB03 gene was used as a target gene (target sequence: CACGTTCACCTTGCCCCACA (SEQ ID NO: 34)/non-target sequence: CACGTTCACtTTGCCCCACA (SEQ ID NO: 35)), it was confirmed that, for F539S/M763I/K890N, compared to the wild-type SpCas9, indel frequencies at the on-target site increase, but indel frequencies at the off-target site decrease, for F539S/M763I/K890N/F1038Y, compared to the wild-type SpCas9, indel frequencies at the on-target site slightly decrease, but indel frequencies at the off-target site decrease by approximately 70% or more, and thus the ratio of indel frequency at the off-target site based on the value of the on-target site was low. Therefore, it was confirmed that F539S/M763I/K890N and F539S/M763I/K890N/F1038Y have target specificity, compared to the wild-type SpCas9 (FIG. 21). In addition, it was confirmed that, compared to the wild-type SpCas9, for F539S/M763I/D965Y/K890N, indel frequencies at the off-target site slightly increase, but indel frequencies at the on-target sites increase by approximately 10 to 20%, and thus the ratio of indel frequency at the off-target site based on the value of the on-target site was low. Therefore, it can be confirmed that F539S/M763I/D965Y/K890N has target specificity, compared to the wild-type SpCas9 (FIG. 21).

Figure 22:
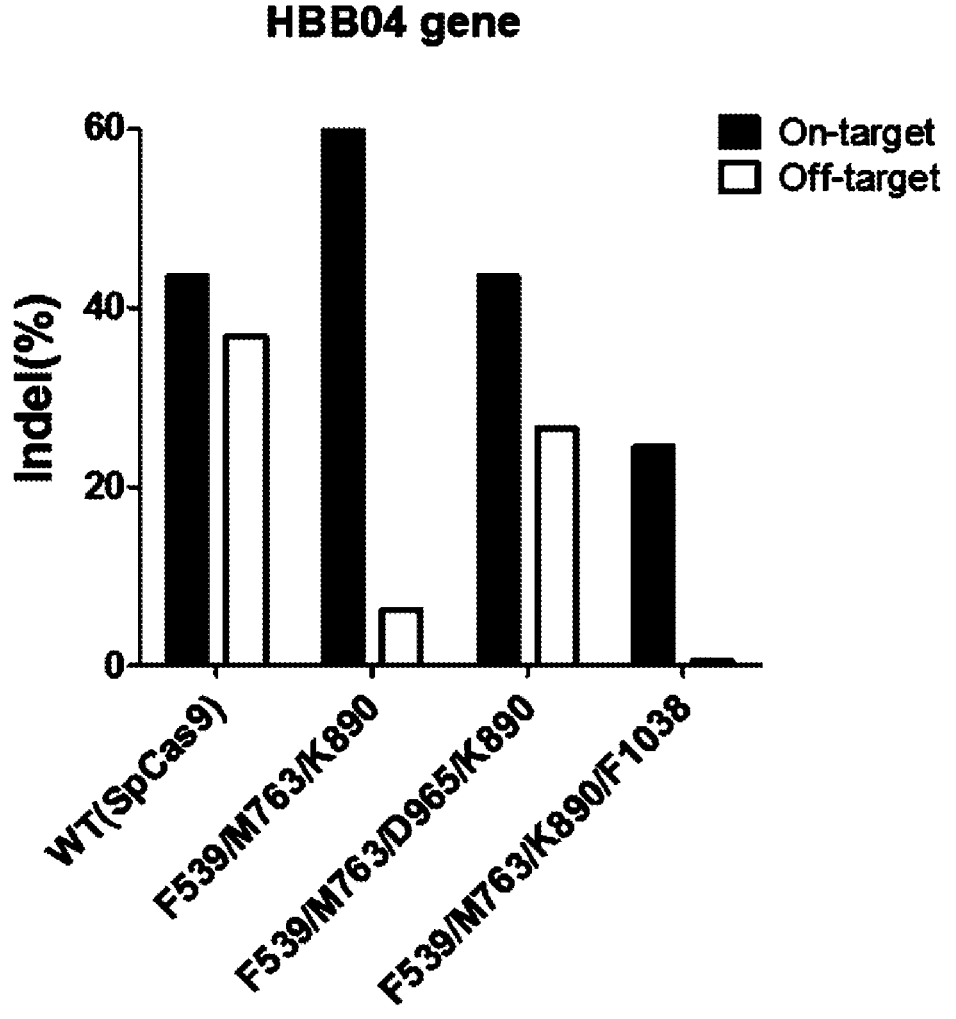
FIG. 22 is a graph showing indel frequencies (%), which represents the manipulation effect of a target gene (HBB04 gene) by SpCas9 variants having mutations in three regions of the four regions of SpCas9.

When an HBB04 gene was used as a target gene (target sequence: CCACGTTCACCTTGCCCCAC (SEQ ID NO: 36)/non-target sequence: CCACaTTCACCTTGCCCCAC (SEQ ID NO: 37)), it was confirmed that, compared to the wild-type SpCas9, for F539S/M763I/K890N, indel frequencies at the on-target site increase, indel frequencies at the off-target site significantly decrease, and for F539S/M763I/D965Y/K890N, indel frequencies at the on-target site are similar, but indel frequencies at the off-target site decrease by approximately 10 to 20% (FIG. 22). In addition, it was confirmed that, for F539S/M763I/K890N/F1038Y, compared to the wild-type SpCas9, indel frequencies at the on-target site decrease by approximately 40%, indel frequencies at the off-target site are almost not shown, and thus the ratio of indel frequency at the off-target site based on the value of the on-target site was lower compared to the wild-type SpCas9. Therefore, it was confirmed that F539S/M763I/K890N has target specificity, compared to the wild-type SpCas9 (FIG. 22).

Form the above-mentioned results, it can be confirmed that the SpCas9 variants (F539S/M763I/K890N, F539S/M763I/D965Y/K890N, F539S/M763I/K890N/F1038Y and A203D/N277H/G366S/M763I/F1038Y/T1102P/D1127E) having mutations in three or more regions of the four regions of SpCas9 are improved in target specificity, compared to the wild-type SpCas9.

Form the above-mentioned results, it was confirmed that the SpCas9 variants having mutations in one or more amino acids selected from the four regions of SpCas9 were improved in target specificity, compared to the wild-type SpCas9.

INDUSTRIAL APPLICABILITY

In the present invention, a CRISPR-Cas system improved in target specificity using an artificially engineered CRISPR enzyme can be used in genome and/or epigenome manipulation or modification, genome targeting, genome editing, and in vitro diagnosis, etc.

[Sequence Listing Free text]

Amino acid sequence of wild-type SpCas9, amino acid sequence of each region and amino acid sequence of target-specific SpCas9 variant according to one exemplary embodiment This application contains references to amino acid sequences and/or nucleic acid sequences which have been submitted concurrently herewith as the sequence listing text file entitled "000009uscoa_SequenceListing.NRL", file size 44 kilobytes (KB), created on 9 Dec. 2022. The aforementioned sequence listing is hereby incorporated by reference in its entirety pursuant to 37 C.F.R. § 1.52(e)(5)

What is claimed is:

1. A SpCas9 (*Streptococcus pyogenes* Cas9) variant comprising:

all of SEQ ID NO:1 except for:

an aspartic acid at the position corresponding to position 203 of the polypeptide of SEQ ID NO: 1;

a histidine at the position corresponding to position 277 of the polypeptide of SEQ ID NO: 1;

a serine at the position corresponding to position 366 of the polypeptide of SEQ ID NO: 1;

a serine at the position corresponding to position 539 of the polypeptide of SEQ ID NO: 1;

an asparagine at the position corresponding to position 601 of the polypeptide of SEQ ID NO: 1;

an asparagine at the position corresponding to position 890 of the polypeptide of SEQ ID NO: 1;

a tyrosine at the position corresponding to position 965 of the polypeptide of SEQ ID NO: 1;

a tyrosine at the position corresponding to position 1038 of the polypeptide of SEQ ID NO: 1;

a glutamic acid at the position corresponding to position 1127 of the polypeptide of SEQ ID NO: 1;

a serine at the position corresponding to position 539 of the polypeptide of SEQ ID NO: 1, and an isoleucine at the position corresponding to position 763 of the polypeptide of SEQ ID NO: 1;

a serine at the position corresponding to position 539 of the polypeptide of SEQ ID NO: 1, and an asparagine at the position corresponding to position 890 of the polypeptide of SEQ ID NO: 1;

a serine at the position corresponding to position 539 of the polypeptide of SEQ ID NO: 1, and a tyrosine at the position corresponding to position 1038 of the polypeptide of SEQ ID NO: 1;

an asparagine at the position corresponding to position 601 of the polypeptide of SEQ ID NO: 1, and a tyrosine at the position corresponding to position 965 of the polypeptide of SEQ ID NO: 1;

an isoleucine at the position corresponding to position 763 of the polypeptide of SEQ ID NO: 1, and an asparagine at the position corresponding to position 890 of the polypeptide of SEQ ID NO: 1;

an isoleucine at the position corresponding to position 763 of the polypeptide of SEQ ID NO: 1, and a tyrosine at the position corresponding to position 1038 of the polypeptide of SEQ ID NO: 1;

a tyrosine at the position corresponding to position 965 of the polypeptide of SEQ ID NO: 1, and a tyrosine at the position corresponding to position 1038 of the polypeptide of SEQ ID NO: 1;

a serine at the position corresponding to position 539 of the polypeptide of SEQ ID NO: 1, an isoleucine at the position corresponding to position 763 of the polypeptide of SEQ ID NO: 1, and a tyrosine at the position corresponding to position 1038 of the polypeptide of SEQ ID NO: 1;

a serine at the position corresponding to position 539 of the polypeptide of SEQ ID NO: 1, an isoleucine at the position corresponding to position 763 of the polypeptide of SEQ ID NO: 1, an asparagine at the position corresponding to position 890 of the polypeptide of SEQ ID NO: 1, and a tyrosine at the position corresponding to position 965 of the polypeptide of SEQ ID NO: 1; or a serine at the position corresponding to position 539 of the polypeptide of SEQ ID NO: 1, an isoleucine at the position corresponding to position 763 of the polypeptide of SEQ ID NO: 1, an asparagine at the position corresponding to position 890 of the polypeptide of SEQ ID NO: 1, and a tyrosine at the position corresponding to position 1038 of the polypeptide of SEQ ID NO: 1, wherein the SpCas9 variant has an endonuclease activity.

2. The SpCas9 variant of claim 1, wherein the SpCas9 variant further comprises one or more functional domains selected from the group consisting of a tag for isolation and purification;

a deaminase; and an activity domain having methylase activity, demethylase activity, transcription activation activity, transcription repression activity, transcription release factor activity, histone modification activity, RNA cleavage activity, or nucleic acid binding activity.

3. The SpCas9 variant of claim 1, wherein the SpCas9 variant further comprises a reporter protein, a nuclear localization sequence or signal (NLS) or a nuclear export sequence or signal (NES).

4. A composition for gene modification, comprising:

the *Streptococcus pyogenes* Cas9 (SpCas9) variant of claim 1, and a guide RNA, wherein the guide RNA is capable of targeting the interest gene and complexing with the SpCas9 variant.

5. The composition of claim 4, wherein the guide RNA and the SpCas9 variant form a complex which is a ribonucleoprotein (RNP).

6. The composition of claim 4, wherein the composition further comprises a donor nucleic acid that comprises a gene of interest.

7. A composition for gene modification, comprising:

the *Streptococcus pyogenes* Cas9 (SpCas9) variant of claim 1, and a nucleic acid encoding a guide RNA.

8. The composition of claim 7, wherein the composition comprises a vector comprising the nucleic acid encoding the guide RNA.

\* \* \* \* \*

```
                          SEQUENCE LISTING

Sequence total quantity: 37
SEQ ID NO: 1            moltype = AA  length = 1368
FEATURE                 Location/Qualifiers
source                  1..1368
                        mol_type = protein
                        organism = Streptococcus pyogenes
SEQUENCE: 1
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD            1368

SEQ ID NO: 2            moltype = AA  length = 87
FEATURE                 Location/Qualifiers
source                  1..87
                        mol_type = protein
                        organism = Streptococcus pyogenes
SEQUENCE: 2
FEENPINASG VDAKAILSAR LSKSRRLENL IAQLPGEKKN GLFGNLIALS LGLTPNFKSN  60
FDLAEDAKLQ LSKDTYDDDL DNLLAQI                                      87

SEQ ID NO: 3            moltype = AA  length = 79
FEATURE                 Location/Qualifiers
source                  1..79
                        mol_type = protein
                        organism = Streptococcus pyogenes
SEQUENCE: 3
PLSASMIKRY DEHHQDLTLL KALVRQQLPE KYKEIFFDQS KNGYAGYIDG GASQEEFYKF  60
IKPILEKMDG TEELLVKLN                                               79

SEQ ID NO: 4            moltype = AA  length = 103
```

-continued

```
FEATURE                 Location/Qualifiers
source                  1..103
                        mol_type = protein
                        organism = Streptococcus pyogenes
SEQUENCE: 4
KHSLLYEYFT VYNELTKVKY VTEGMRKPAF LSGEQKKAIV DLLFKTNRKV TVKQLKEDYF  60
KKIECFDSVE ISGVEDRFNA SLGTYHDLLK IIKDKDFLDN EEN                    103

SEQ ID NO: 5            moltype = AA  length = 21
FEATURE                 Location/Qualifiers
source                  1..21
                        mol_type = protein
                        organism = Streptococcus pyogenes
SEQUENCE: 5
TILDFLKSDG FANRNFMQLI H                                            21

SEQ ID NO: 6            moltype = AA  length = 22
FEATURE                 Location/Qualifiers
source                  1..22
                        mol_type = protein
                        organism = Streptococcus pyogenes
SEQUENCE: 6
MDKKYSIGLD IGTNSVGWAV IT                                           22

SEQ ID NO: 7            moltype = AA  length = 40
FEATURE                 Location/Qualifiers
source                  1..40
                        mol_type = protein
                        organism = Streptococcus pyogenes
SEQUENCE: 7
PAIKKGILQT VKVVDELVKV MGRHKPENIV IEMARENQTT                        40

SEQ ID NO: 8            moltype = AA  length = 115
FEATURE                 Location/Qualifiers
source                  1..115
                        mol_type = protein
                        organism = Streptococcus pyogenes
SEQUENCE: 8
QITKHVAQIL DSRMNTKYDE NDKLIREVKV ITLKSKLVSD FRKDFQFYKV REINNYHHAH  60
DAYLNAVVGT ALIKKYPKLE SEFVYGDYKV YDVRKMIAKS EQEIGKATAK YFFYS       115

SEQ ID NO: 9            moltype = AA  length = 126
FEATURE                 Location/Qualifiers
source                  1..126
                        mol_type = protein
                        organism = Streptococcus pyogenes
SEQUENCE: 9
KNSRERMKRI EEGIKELGSQ ILKEHPVENT QLQNEKLYLY YLQNGRDMYV DQELDINRLS  60
DYDVDHIVPQ SFLKDDSIDN KVLTRSDKNR GKSDNVPSEE VVKKMKNYWR QLLNAKLITQ  120
RKFDNL                                                            126

SEQ ID NO: 10           moltype = AA  length = 41
FEATURE                 Location/Qualifiers
source                  1..41
                        mol_type = protein
                        organism = Streptococcus pyogenes
SEQUENCE: 10
EVQTGGFSKE SILPKRNSDK LIARKKDWDP KKYGGFDSPT V                      41

SEQ ID NO: 11           moltype = AA  length = 1368
FEATURE                 Location/Qualifiers
REGION                  1..1368
                        note = Streptococcus pyogenes Cas9 variant
source                  1..1368
                        mol_type = protein
                        organism = synthetic construct
SEQUENCE: 11
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPASL  540
SGEQKKAIVD LLFKTNRKVT VKQLKEDYFK IECFDSVEI SGVEDRFNAS LGTYHDLLKI   600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
```

```
HEHIANLAGS PAIKKGILQT VKVVDELVKV MGRHKPENIV IEIARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAN LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGD              1368

SEQ ID NO: 12            moltype = AA  length = 7
FEATURE                  Location/Qualifiers
REGION                   1..7
                         note = nuclear localization sequence
source                   1..7
                         mol_type = protein
                         organism = synthetic construct
SEQUENCE: 12
PKKKRKV                                                                 7

SEQ ID NO: 13            moltype = AA  length = 16
FEATURE                  Location/Qualifiers
REGION                   1..16
                         note = nuclear localization sequence
source                   1..16
                         mol_type = protein
                         organism = synthetic construct
SEQUENCE: 13
KRPAATKKAG QAKKKK                                                      16

SEQ ID NO: 14            moltype = AA  length = 9
FEATURE                  Location/Qualifiers
REGION                   1..9
                         note = nuclear localization sequence
source                   1..9
                         mol_type = protein
                         organism = synthetic construct
SEQUENCE: 14
PAAKRVKLD                                                               9

SEQ ID NO: 15            moltype = AA  length = 11
FEATURE                  Location/Qualifiers
REGION                   1..11
                         note = nuclear localization sequence
source                   1..11
                         mol_type = protein
                         organism = synthetic construct
SEQUENCE: 15
RQRRNELKRS P                                                           11

SEQ ID NO: 16            moltype = AA  length = 38
FEATURE                  Location/Qualifiers
REGION                   1..38
                         note = nuclear localization sequence
source                   1..38
                         mol_type = protein
                         organism = synthetic construct
SEQUENCE: 16
NQSSNFGPMK GGNFGGRSSG PYGGGGQYFA KPRNQGGY                              38

SEQ ID NO: 17            moltype = AA  length = 42
FEATURE                  Location/Qualifiers
REGION                   1..42
                         note = nuclear localization sequence
source                   1..42
                         mol_type = protein
                         organism = synthetic construct
SEQUENCE: 17
RMRIZFKNKG KDTAELRRRR VEVSVELRKA KKDEQILKRR NV                         42

SEQ ID NO: 18            moltype = AA  length = 8
FEATURE                  Location/Qualifiers
REGION                   1..8
                         note = nuclear localization sequence
source                   1..8
                         mol_type = protein
                         organism = synthetic construct
```

-continued

```
SEQUENCE: 18
VSRKRPRP                                                                 8

SEQ ID NO: 19       moltype = AA  length = 8
FEATURE             Location/Qualifiers
REGION              1..8
                    note = nuclear localization sequence
source              1..8
                    mol_type = protein
                    organism = synthetic construct
SEQUENCE: 19
PPKKARED                                                                 8

SEQ ID NO: 20       moltype = AA  length = 8
FEATURE             Location/Qualifiers
REGION              1..8
                    note = nuclear localization sequence
source              1..8
                    mol_type = protein
                    organism = synthetic construct
SEQUENCE: 20
PQPKKKPL                                                                 8

SEQ ID NO: 21       moltype = AA  length = 12
FEATURE             Location/Qualifiers
REGION              1..12
                    note = nuclear localization sequence
source              1..12
                    mol_type = protein
                    organism = synthetic construct
SEQUENCE: 21
SALIKKKKM AP                                                             12

SEQ ID NO: 22       moltype = AA  length = 5
FEATURE             Location/Qualifiers
REGION              1..5
                    note = nuclear localization sequence
source              1..5
                    mol_type = protein
                    organism = synthetic construct
SEQUENCE: 22
DRLRR                                                                    5

SEQ ID NO: 23       moltype = AA  length = 7
FEATURE             Location/Qualifiers
REGION              1..7
                    note = nuclear localization sequence
source              1..7
                    mol_type = protein
                    organism = synthetic construct
SEQUENCE: 23
PKQKKRK                                                                  7

SEQ ID NO: 24       moltype = AA  length = 10
FEATURE             Location/Qualifiers
REGION              1..10
                    note = nuclear localization sequence
source              1..10
                    mol_type = protein
                    organism = synthetic construct
SEQUENCE: 24
RKLKKKIKKL                                                               10

SEQ ID NO: 25       moltype = AA  length = 10
FEATURE             Location/Qualifiers
REGION              1..10
                    note = nuclear localization sequence
source              1..10
                    mol_type = protein
                    organism = synthetic construct
SEQUENCE: 25
REKKKFLKRR                                                               10

SEQ ID NO: 26       moltype = AA  length = 20
FEATURE             Location/Qualifiers
REGION              1..20
                    note = nuclear localization sequence
source              1..20
                    mol_type = protein
```

```
                        organism = synthetic construct
SEQUENCE: 26
KRKGDEVDGV DEVAKKKSKK                                           20

SEQ ID NO: 27          moltype = AA   length = 17
FEATURE                Location/Qualifiers
REGION                 1..17
                       note = nuclear localization sequence
source                 1..17
                       mol_type = protein
                       organism = synthetic construct
SEQUENCE: 27
RKCLQAGMNL EARKTKK                                              17

SEQ ID NO: 28          moltype = DNA   length = 20
FEATURE                Location/Qualifiers
source                 1..20
                       mol_type = other DNA
                       organism = Homo sapiens
SEQUENCE: 28
ctttctacct actgagtctg                                          20

SEQ ID NO: 29          moltype = DNA   length = 20
FEATURE                Location/Qualifiers
misc_feature           1..20
                       note = non-target sequence
source                 1..20
                       mol_type = other DNA
                       organism = synthetic construct
SEQUENCE: 29
ctttctacct accgagtctg                                          20

SEQ ID NO: 30          moltype = DNA   length = 20
FEATURE                Location/Qualifiers
source                 1..20
                       mol_type = other DNA
                       organism = Homo sapiens
SEQUENCE: 30
gagtccgagc agaagaagaa                                          20

SEQ ID NO: 31          moltype = DNA   length = 20
FEATURE                Location/Qualifiers
misc_feature           1..20
                       note = non-target sequence
source                 1..20
                       mol_type = other DNA
                       organism = synthetic construct
SEQUENCE: 31
gagttagagc agaagaagaa                                          20

SEQ ID NO: 32          moltype = DNA   length = 20
FEATURE                Location/Qualifiers
source                 1..20
                       mol_type = other DNA
                       organism = Homo sapiens
SEQUENCE: 32
ggtgagtgag tgtgtgcgtg                                          20

SEQ ID NO: 33          moltype = DNA   length = 20
FEATURE                Location/Qualifiers
misc_feature           1..20
                       note = non-target sequence
source                 1..20
                       mol_type = other DNA
                       organism = synthetic construct
SEQUENCE: 33
ggtgagtgag tgtgtgtgtg                                          20

SEQ ID NO: 34          moltype = DNA   length = 20
FEATURE                Location/Qualifiers
source                 1..20
                       mol_type = other DNA
                       organism = Homo sapiens
SEQUENCE: 34
cacgttcacc ttgccccaca                                          20

SEQ ID NO: 35          moltype = DNA   length = 20
FEATURE                Location/Qualifiers
misc_feature           1..20
```

-continued

```
                      note = non-target sequence
source                1..20
                      mol_type = other DNA
                      organism = synthetic construct
SEQUENCE: 35
cacgttcact ttgccccaca                                              20

SEQ ID NO: 36         moltype = DNA   length = 20
FEATURE               Location/Qualifiers
source                1..20
                      mol_type = other DNA
                      organism = Homo sapiens
SEQUENCE: 36
ccacgttcac cttgccccac                                              20

SEQ ID NO: 37         moltype = DNA   length = 20
FEATURE               Location/Qualifiers
misc_feature          1..20
                      note = non-target sequence
source                1..20
                      mol_type = other DNA
                      organism = synthetic construct
SEQUENCE: 37
ccacattcac cttgccccac                                              20
```